US008383816B2

(12) United States Patent
Niculescu-Duvaz et al.

(10) Patent No.: US 8,383,816 B2
(45) Date of Patent: Feb. 26, 2013

(54) ARYL-QUINOLYL COMPOUNDS AND THEIR USE

(75) Inventors: Ion Niculescu-Duvaz, Sutton (GB); Alfonso Zambon, Sutton (GB); Dan Niculescu-Duvaz, Sutton (GB); Steven Whittaker, London (GB); Richard Marais, London (GB); Caroline Joy Springer, Sutton (GB)

(73) Assignees: Cancer Research Technology Limited, London (GB); Institute of Cancer Research: Royal Cancer Hospital (The), London (GB)

( * ) Notice: Subject to any disclaimer, the term of this patent is extended or adjusted under 35 U.S.C. 154(b) by 162 days.

(21) Appl. No.: 12/988,619

(22) PCT Filed: Apr. 27, 2009

(86) PCT No.: PCT/GB2009/001077
§ 371 (c)(1),
(2), (4) Date: Oct. 19, 2010

(87) PCT Pub. No.: WO2009/130487
PCT Pub. Date: Oct. 29, 2009

(65) Prior Publication Data
US 2011/0053946 A1    Mar. 3, 2011

Related U.S. Application Data

(60) Provisional application No. 61/047,902, filed on Apr. 25, 2008.

(30) Foreign Application Priority Data

Apr. 25, 2008   (GB) ................................... 0807609.3

(51) Int. Cl.
C07D 513/02    (2006.01)
(52) U.S. Cl. ....................................................... 546/118
(58) Field of Classification Search ................... 546/118
See application file for complete search history.

(56) References Cited

U.S. PATENT DOCUMENTS

| 4,666,828 | A | 5/1987 | Gusella |
| 4,683,202 | A | 7/1987 | Mullis |
| 4,801,531 | A | 1/1989 | Frossard |
| 5,192,659 | A | 3/1993 | Simons |
| 5,272,057 | A | 12/1993 | Smulson |
| 5,521,073 | A | 5/1996 | Davis |
| 5,877,020 | A | 3/1999 | Alitalo |
| 5,879,672 | A | 3/1999 | Davis |
| 5,882,864 | A | 3/1999 | An |
| 6,030,831 | A | 2/2000 | Godowski |
| 6,218,529 | B1 | 4/2001 | An |
| 6,258,809 | B1 | 7/2001 | Rajagopalan |
| 6,492,529 | B1 | 12/2002 | Kapadia et al. |
| 7,625,922 | B2 | 12/2009 | Niculescu-Duvaz et al. |
| 7,951,819 | B2 | 5/2011 | Niculescu-Duvaz et al. |
| 8,198,279 | B2 | 6/2012 | Springer et al. |
| 2004/0082583 | A1 | 4/2004 | Cheung et al. |
| 2007/0287838 | A1 | 12/2007 | Niculescu-Duvaz et al. |
| 2009/0325945 | A1 | 12/2009 | Niculescu-Duvaz et al. |
| 2010/0298320 | A1 | 11/2010 | Springer et al. |
| 2012/0238568 | A1 | 9/2012 | Springer et al. |

FOREIGN PATENT DOCUMENTS

| EP | 1724268 A1 | 11/2006 |
| JP | 56-065863 | 6/1981 |
| JP | 57-038777 | 3/1982 |
| WO | WO 98/13350 A1 | 4/1998 |
| WO | WO 99/16438 A1 | 4/1999 |
| WO | WO 99/21859 A1 | 5/1999 |
| WO | WO 01/36383 A1 | 5/2001 |
| WO | WO 01/46196 A1 | 6/2001 |
| WO | WO 03/056036 A2 | 7/2003 |
| WO | WO 2004/014300 A2 | 2/2004 |
| WO | WO 2006/003378 A1 | 1/2006 |
| WO | WO 2006/024834 A1 | 3/2006 |
| WO | WO 2006/043090 A1 | 4/2006 |
| WO | WO 2006/067466 A2 | 6/2006 |
| WO | WO 2007/067444 A1 | 6/2007 |
| WO | WO 2007/076092 A2 | 7/2007 |
| WO | WO 2007/125330 | 11/2007 |
| WO | WO 2008/044688 A1 | 4/2008 |
| WO | WO 2009/077766 | 6/2009 |
| WO | WO 2009/130487 | 10/2009 |
| WO | WO 2011/092469 A1 | 8/2011 |

OTHER PUBLICATIONS

Golub et al. 1999, "Molecular Classification of Cancer: Class Discovery and Class Prediction by Gene Express Monitoring", Science 286:531-537.
Lala et al. 1998, "Role of nitric oxide in tumor preogression: Lessons from experimental tumors", Cancer and Metastasis Reviews 17(1):91-106.
Bos, Sep. 1, 1989, "ras Oncogenes in Human Cancer: A Review," Cancer Research, vol. 49, pp. 4682-4689.
Downward, Jan. 2003, "Targeting RAS Signalling Pathways in Cancer Therapy," Nature Reviews Cancer, vol. 3, pp. 11-22.
Garnett and Marais, Oct. 2004, "Guilty as charged: B-RAF is a human oncogene," Cancer Cell, vol. 6, pp. 313-319.
Gray-Schopfer et al., 2007, "Melanoma biology and new targeted therapy," Nature, vol. 445, pp. 851-857. Solit et al., 2006, "BRAF mutation predicts sensitivity to MEK inhibition," Nature, vol. 439, pp. 358-362.
Suijkerbuijk et al., Mar. 2010, "Development of Novel, Highly Potent Inhibitors of V-RAF Murine Sarcoma Viral Oncogene Homologue B1 (BRAF): Increasing Cellular Potency through Optimization of a Distal Heteroaromatic Group," J. Med. Chem., vol. 53, pp. 2741-2756.

(Continued)

*Primary Examiner* — Nizal Chandrakumar
(74) *Attorney, Agent, or Firm* — Swanson & Bratschun, L.L.C.

(57) ABSTRACT

The present invention pertains generally to the field of therapeutic compounds for treating proliferative disorders, cancer, etc., and more specifically to certain aryl-quinolyl compounds, as described herein, which, inter alia, inhibit RAF (e.g., B-RAF) activity. The present invention also pertains to pharmaceutical compositions comprising such compounds, and the use of such compounds and compositions, both in vitro and in vivo, to inhibit RAF (e.g., BRAF) activity, to inhibit receptor tyrosine kinase (RTK) activity, to inhibit cell proliferation, and in the treatment of diseases and disorders that are ameliorated by the inhibition of RAF, RTK, etc., proliferative disorders such as cancer (e.g., colorectal cancer, melanoma), etc.

29 Claims, No Drawings

OTHER PUBLICATIONS

Wellbrock et al., 2004, "The RAF proteins take centre stage," Nature Reviews Mollecular Cell Biology, vol. 5, pp. 875-885.

Young et al., 2009, "Ras signaling and therapies," Adv. Cancer Res., vol. 102, pp. 1-17.

Adams, R.H., et al., 1999, "Roles of ephrinB ligands and EphB receptors in cardiovascular development: demarcation of arterial/venous domains, vascular morphogenesis, and sprouting angiogenesis" Genes Dev, vol. 13, pp. 295-306.

Ananthanarayanan, C., et al., 1988, "Reaction of azides in presence of aluminium chloride", Indian Journal of Chemistry, Section B, vol. 27B, pp. 156-157.

Angerer, L.M., et al., 1987, "Demonstration of tissue-specific gene expression by in situ hybridization", Meth. Enzymol., vol. 152, pp. 649-661.

Auvray, P., et al., 1988, "Preparation and nucleophilic substitution of (E)-1-bromo-2-phenylsulfonyl-2-alkenes and 3-acetoxy-2-phenylsulfonyl-1-alkenes", Tetrahedron, vol. 44, No. 19, pp. 6095-6106.

Avenoza, A., et al., Jun. 1995, "New efficient synthesis of 4-amino-3-arylphenols", Synthesis, pp. 671-674.

Ballesteros, P., et al., 1987, "Study of the catalytic properties of tris (3,6-dioxaheptyl) amine (TDA-1) in heteroaromatic nucleophilic substitution of chloropyridines and their N-oxides", Tetrahedron, vol. 43, No. 11, pp. 2557-2564.

Berge et al., Jan. 1977, "Pharmaceutical Salts," J. Pharm. Sci., vol. 66, No. 1, pp. 1-19.

Bhatt, D.J., et al., May 1980, "Preparation of N'-2-phenyl-4-quinolinoyl-N3-aryl thioureas", J. Instit. Chem. (India), vol. 52, pp. 113-114.

Bianchi, M., et al., Jul.-Aug. 1981, "Compounds with antiulcer and antisecretory activity", Eur. J. Med. Chem., vol. 16, No. 4, pp. 321-326.

Borthakur, N., et al., 1995, "New direct synthesis of thioamides from carboxylic acids", Tetrahedron Letters, vol. 36, No. 37, pp. 6745-6746.

Broekhof, N., et al., 1981, "Novel applications of α-aminosubstituted diphenylphosphine oxides. The conversion of aldehydes into α-aminomethylketones", Tetrahedron Letters, vol. 22, No. 29, pp. 2799-2802.

Brooks et al., Dec. 30,1994, "Integrin $\alpha\beta_3$ antagonists promote tumor regression by inducing apoptosis of angiogenic blood vessels" Cell, vol. 79, pp. 1157-1164.

Brose, M., et al., Dec. 1, 2002, "BRAF and RAS mutations in human lung cancer and melanoma" Cancer Res., vol. 62, pp. 6997-7000.

Brückner et al., Mar. 14, 1997, "Tyrosine phosphorylation of transmembrane ligands for Eph receptors" Science, vol. 275, pp. 1640-1643.

Bruder, J.T., et al., 1992, "Serum-, TPA-, and Ras-induced expression from Ap-1/Ets-driven promotors requireds Raf-1 kinase" Genes and Development, vol. 6, pp. 545-556.

Cantrell, D.A., 2003, "GTPases and T cell activation" Immunol Rev., vol. 192, pp. 122-130.

Chan, A.C., 1995, "Regulation of antigen receptor signal transduction by protein tyrosine kinases" Curr. Opin.Immunol., vol. 8(3), pp. 394-401.

Clare, B.W., et al., 2001, "Protease inhibitors: synthesis of a series of bacterial collagenase inhibitors of the sulfonyl amino acyl hydroxamate type", J. Med. Chem., vol. 44, pp. 2253-2258.

Cohen, Y., et al., Jul. 2003, "Lack of BRAF mutation in primary uveal melanoma" Invest. Ophthalmol. Vis. Sci., vol. 44, No. 7, pp. 2876-2878.

Colville-Nash and Scott, 1992, "Angiogenesis and rheumatoid arthritis: pathogenic and therapeutic implications" Ann. Rhum. Dis., vol. 51, pp. 919-925.

Comins, D.L., et al., 1994, "Grignard addition to 1-acyl salts of chiral 4-alkoxypyridines. A new enantioselective preparation of 2-alkyl-2,3-dihydro-4- pyridones", Tetrahedron Letters, vol. 35, No. 40, pp. 7343-7346.

Cooper, J.A., 1994, "Membrane-associated tyrosine kinases as molecular switches" Semin. Cell Biol., vol. 5(6), pp. 377-387.

Correia, J., 1978, "Reaction of phenylglyoxal with aniline under acidic conditions", J. Org. Chem., vol. 43, No. 17, pp. 3394-3396.

Courtneidge, S.A., et al. 1993, "The Src family of protein tyrosine kinases: regulation and functions", Dev. Supp.l, pp. 57-64.

Cowely, S., et al., Jun. 17, 1994, "Activation of MAP kinase kinase is necessary and sufficient for PC12 differentiation and for transformation of NIH 3T3 cells" Cell, vol. 77, pp. 841-852.

Davies, H., et al., Jun. 27, 2002, "Mutations of the BRAF gene in human cancer", Nature, vol. 417, pp. 949-954.

Davis et al., Dec. 27, 1996, "Isolation of angiopoietin-1, a ligand for the TIE2 receptors, by secretion-trap expression cloning", Cell, vol. 87, pp. 1161-1169.

Denekamp, Mar. 1993, "Review article: Angiogenesis, neovascular proliferation and vascular pathophysiology as targets for cancer therapy" Br. J. Rad., vol. 66, No. 783, pp. 181-196.

Dickson, B., et al., Dec. 10, 1992, "Raf functions downstream of Ras1 in the sevenless signal transduction pathway" Nature, vol. 360, pp. 600-603.

DuBois, G.E., 1980, "Amination of aryl sufamate esters. A convenient general synthesis of aliphatic sulfamides", J. Org. Chem., vol. 45, pp. 5373-5375.

Fidler and Ellis, Oct. 21, 1994, "The Implications of angiogenesis for the biology and therapy of cancer metastasis" Cell, vol. 79, pp. 185-188.

Folkman, 1997, "Angiogenesis and angiogenesis inhibition: An overview", EXS, vol. 79, pp. 1-8.

Folkman, 1995, "Angiogenesis in cancer, vascular, rheumatoid and other disease" Nature Medicine, vol. 1, pp. 27-31.

Folkman and Shing, Jun. 5, 1992, "Angiogenesis", J. Biol. Chem., vol. 267, No. 16, pp. 10931-10934.

Folkman, 1992, "The role of angiogenesis in tumor growth", Cancer Biol., vol. 3, pp. 65-71.

Fourrey, J-L.,1987, "Preparation of stable 1,4-dihydropyrazines", J. Chem. Soc., Perkins Transactions 1: Org. & Bio. Chem., vol. 8, pp. 1841-1843.

Friedlander et al., Dec. 1,1995, "Definition of two angiogenic pathways by distinct $\alpha_v$ integrins", Science, vol. 270, pp. 1500-1502.

Gale and Yancopoulos, 1999, "Growth factors acting via endothelial cell-specific receptor tyrosine kinases: VEGFs, angiopoietins, and ephrins in vascular development", Genes Dev, vol. 13, pp. 1055-1066.

Galons, H., et al., May 1981, "Cyclisation indolique selon Bischler en presence d'acides de Lewis", J. Heterocyclic Chemistry, vol. 18, pp. 561-563 (in French, with partial English language translation).

Genot, E. and Cantrell, D.A., 2000, "Ras regulation and function in lymphocytes", Curr. Opin. Immunol., vol. 12(3), pp. 289-294.

Giannotti, D., et al., 1991, "New dibenzothiadiazepine derivatives with antidepressant activities", J. Med. Chem., vol. 34, pp. 1356-1362.

Giardina, G.A.M., et al., 1999, "Replacement of the quinoline system in 2-phenyl-4-quinolinecarboxamide NK-3 receptor antagonists", II Farmaco, vol. 54, pp. 364-374.

Glinka, R., et al., 1991, "Synthesis and structure of new hetercyclic systems containing the sulfamide group", Pol. J. Chem., vol. 65, pp. 2053-2055.

Gorden, A., et al., Jul. 15, 2003, "Analysis of BRAF and N-RAS mutations in metastatic malanoma tissues", Cancer Research, vol. 63, pp. 3955-3957.

Guarna, A., et al., 2002, "Synthesis of a new enantiopure bicyclic γ/δ-amino acid (BTKa) derived from tartaric acid and α-amino acetophenone", Tetrahedron, vol. 58, pp. 9865-9870.

Haesslein, J., et al., 2002, "Recent advances in cyclin-dependent kinase inhibition. Purine-based derivatives as anti-cancer agents. Roles and perspectives for the future", Curr. Top. Med. Chem., vol. 2, pp. 1037-1050.

Hammond, M., et al., 2003, "Structure-activity relationships in a series of NPY Y5 antagonists: 3-amido-9-ethylcarbazoles, core-modified analogues and amide isosteres", Bioorganic & Medicinal Chemistry Letters, vol. 13, pp. 1989-1992.

Helbling, P.M., et al., 2000, "The receptor tyrosine kinase EphB4 and ephrin-B ligands restrict angiogenic growth of embryonic veins in Xenopus laevis", Development, vol. 127, pp. 269-278.

Hirayama, F., et al., 2002, "Design, synthesis and biological activity of YM-60828 derivatives: potent and orally-bioavailable factor Xa inhibitors based on naphthaoanilide and naphthalensulfonanilide templates", Bioorganic & Medicinal Chemistry, vol. 10, pp. 2597-2610.

Holland, S.J., et al., Oct. 24, 1996, "Bidirectional signalling through the EPH-family receptor Nuk and its transmembrane ligands", Nature, vol. 383, pp. 722-725.

Ingber et al., Dec. 6, 1990, "Synthetic analogues of fumagillin that inhibit angiogenesis and suppress tumour growth", Nature, vol. 348, pp. 555-557.

Ishii, A., et al., 1997, "First synthesis and reactivities of isolable dithiiranes and their 1-oxides", Bull. Chem. Soc. Jpn., vol. 70, pp. 509-523.

Itaya, T., et al., 1998, "Syntheses of the marine ascidian purine aplidiamine and its 9-beta-d-ribofuranoside", Tetrahedron Letters, vol. 39, pp. 4695-4696.

Janvier, P., et al., 2002, "Ammonium chloride-promoted four-component synthesis of pyrrolo[3-4-b]pyridin-5-one", J. Am. Chem, Soc., vol. 124, No. 11, pp. 2560-2567.

Johnson, C.R., et al., Jun. 22, 1979, "Preparation and reactions of sulfonimidoyl chlorides", Journal of Organic Chemistry, vol. 44, No. 13, pp. 2055-2061.

Juršić, B., 1988, "Synthetic application of micellar catalysis. Williamson's synthesis of ethers", Tetrahedron, vol. 44, No. 21, pp. 6677-6680.

Kahlon et al., Jan./Feb. 1992, "Angiogenesis in atherosclerosis", Can. J. Cardiol., vol. 8, No. 1, pp. 60-64.

Kolch, W., et al., Jan. 1991, "Raf-1 protein kinase is required for growth of induced NIH/3T3 cells", Nature, vol. 349, No. 31, pp. 426-428.

Lemonnier et al., 2001, "Role of N-cadherin and protein kinase C in osteoblast gene activation induced by the S252W fibroblast growth factor receptor 2 mutation in apert craniosynostosis", J. Bone Miner. Res., vol. 16, No. 5, pp. 832-845.

Liu, W., et al., 2004, "Effects of overexpression of ephrin-B2 on tumour growth in human colorectal cancer", Brit. J. Canc., vol. 90, pp. 1620-1626.

Lozinskii, M.O., et al., 2002, "Alkylthio derivatives of the aminoketene S,N-acetals of heterocyclic β-dicarbonyl compounds: one stage synthesis and properties", Chemistry of Heterocyclic Compounds, vol. 38, No. 9, pp. 1077-1080.

Mansour, S.J., et al., Aug. 12, 1994, "Transformation of mammalian cells by constitutively active MAP kinase kinase", Science, vol. 265, pp. 966-970.

Marais R., et al., Feb. 14, 1997, "Differential regulation of Raf-1, A-Raf, and B-Raf by oncogenic Ras and tyrosine kinases", J. Biol. Chem., vol. 272, No. 7, pp. 4378-4383.

Mataloni, M., et al., 2003, "Synthesis of secondary amines by reduction of α-amidoalkylphenyl sulfones with sodium acetoxyborohydride", Synlett, vol. 8, pp. 1129-1132.

McMahon, G., 2000, "VEGF receptor signalling in tumor angiogenesis", The Oncologist, vol. 5(suppl I), pp. 3-10.

Messinger, P., et al., "Notiz zur synthese von α-amino- und α-amidosulfonen", Archive Der Pharmazie, 1974, vol. 307, pp. 653-655 (in German, with partial English language translation).

Meyers et al., 1996, "FGFR2 exon IIIa and IIIc mutations in Crouzon, Jackson-Weiss, and Pfeiffer syndromes: evidence for missense changes, insertions, and a deletion due to alternative RNA splicing", Am. J. Hum. Genet., vol. 58, pp. 491-498.

Mineo et al., 2004, "Prognostic impact of VEGF, CD31, CD34, and CD105 expression and tumour vessel invasion after radical surgery for IB-IIA non-small cell lung cancer", J. Clin. Pathol. , vol. 57(6), pp. 591-597.

Mohanta, P.K., et al., 2000, "1-(methyldithiocarbony)imidazole: a useful thiocarbonyl transfer reagent for synthesis of substituted thioureas", Tetrahedron, vol. 56, pp. 629-637.

Moore, J.D., et al., 2003, "ROMP-generated oligomeric sulfonyl chlorides as versatile soluble scavenging agents", Organic Letters, vol. 5, No. 2, pp. 105-107.

Mustonen, T., et al., 1995, "Endothelial receptor tyrosine kinases involved in angiogenesis", J. Cell Biol., vol. 129, pp. 895-898.

Nakamoto, M. and Bergemann, A.D., 2002, "Diverse roles for the Eph family of receptor tyrosine kinases in carcinogenesis", Microsc. Res Tech., vol. 59, pp. 58-67.

O'Reilly et al., Oct. 21, 1994, "Angiostatin: A novel angiogenesis inhibitor that mediates the suppression of metastases by a Lewis lung carcinoma", Cell, vol. 79, pp. 315-328.

Orre and Rogers, 1999, "VEGF, VEGFR-1, VEGFR-2, microvessel density and endothelial cell proliferation in tumours of the ovary", Int. J. Cancer, vol. 84(2), pp. 101-108.

Ozawa et al., 2001, "Growth factors and their receptors in pancreatic cancer", Teratog. Carcinog. Mutagen., vol. 21, pp. 27-44.

Pabst, B., et al., 1999, "Analysis of K-ras mutations in pancreatic tissue after fine needle aspirates", Anticancer Research, vol. 19, pp. 2481-2484.

Parlow, J.J., et al., 2003, "Synthesis and crystal structures of substituted benzenes and benzoquinones as tissue factor VIIa inhibitors", J. Med. Chem., vol. 46, pp. 4297-4312.

Partanen et al., Apr. 1992, "A novel endothelial cell surface receptor tyrosine kinase with extracellular epidermal growth factor homology domains", Mol. Cell Biol., vol. 12, No. 4, pp. 1698-1707.

Partanen et al., 1999, "Functions of Tie1 and Tie2 receptor tyrosine kinases in vascular development", Curr. Topics Microbiol. Immunol., vol. 237, pp. 159-172.

Paulson, R.F., 1995, "Receptor tyrosine kinases and the regulation of hematopoiesis", Semin. Immunol., vol. 7(4), pp. 267-277.

Peacock et al., Apr. 1992, "Angiogenesis inhibition suppresses collagen arthritis", J. Exp. Med., vol. 175, pp. 1135-1138.

Peacock et al., 1995, "A novel angiogenesis inhibitor suppresses rat adjuvant arthritis", Cell. Immun., vol. 160, pp. 178-184.

Peters, K. G., 1998, "Vascular endothelial growth factor and the angiopoietins working together to build a better blood vessel", Circ. Res., vol. 83(3), pp. 342-343.

Pinedo, H.M., et al., 2000, "Translational research: the role of VEGF in tumor angiogenesis", The Oncologist, vol. 5 (90001), pp. 1-2.

Plomp et al., 1998, "Pfeiffer syndrome type 2: further delineation and review of the literature", Am. J. Med. Genet., vol. 75, pp. 245-251.

Powers et al., 2000, "Fibroblast growth factors, their receptors and signalling", Endocr. Relat. Cancer, vol. 7, pp. 165-197.

Prakash, O., et al., 1992, "A convenient synthesis of α-anilinoacetophenones using hypervalent iodine", Indian Journal of Chemistry, Section B: Organic Chemistry Including Medicinal Chemistry, vol. 31B, pp. 349-350.

Prix, L., et al., 2002, "Diagnostic biochip array for fast and sensitive detection of K-ras mutations in stool", Clinical Chemistry, vol. 48, pp. 428-435.

Rajagopalan, H. et al., Aug. 28m 2002, "RAF/RAS oncogenes and mismatch-repairs status", Nature, vol. 418, p. 934.

Ramadas, K., et al., 1997, "LAC sulfur assisted synthesis of symmetrical thioureas", Synth. Comm., vol. 27(23), pp. 2255-2260.

Sarkis, G.Y., et al., Jan-Feb. 1985, "Synthesis and spectroscopic properties of some new N,N'-disubstituted thioureas of potential biological interest", J. Heterocyclic Chemistry, vol. 22, pp. 137-140.

Shaw, J.T., et al., Jan. 1980, "The preparation of 2,6-diaminopyrazine, 2,6-diazidopyrazine and some of their derivatives", J. Het. Chem., vol. 17(11), pp. 11-16.

Shiina, I., et al., 2003, "A new method for the synthesis of carboxamides and peptides using 1,1'-carbonyldioxydi[2(1H)-pyridone] (CDOP) in the absence of basic promoters", Tetrahedron Letters, vol. 44, pp. 1952-1955.

Shin, D., et al., 2001, "Expression of EphrinB2 identifies a stable genetic difference between arterial and venous vascular smooth muscle as well as endothelial cells, and marks subsets of microvessels at sites of adult neovascularisation", Dev Biol, vol. 230, pp. 139-150.

Singer, G., et al., Mar. 19, 2003, "Mutations in BRAF and KRAS characterize the development of low-grade ovarian serous carcinoma", J. Natl. Cancer Inst., vol. 95, No. 6, pp. 484-486.

Srinivas, K.V.N.S., et al., 2003, "A highly convenient, efficient, and selective process for preparation of esters and amides from carboxylic acids using Fe3+-L-1- montmorillonite clay", J. of Org. Chem., vol. 68, pp. 1165-1167.

Srivastava, P.K., et al., Apr. 5, 1981, "Synthesis and antithyroid activity of some benzimidazolyl and benzenesulphonyl thiocarbamides", Current Science, vol. 50, No. 7, pp. 305-307.

Suri et al., Dec. 27, 1996, "Requisite role of angiopoietin-1, a ligand for TIE2 receptor, during embryonic angiogenesis", Cell, vol. 87, pp. 1171-1180.

Tang, X.X., et al., Feb. 1999, "Coexpression of transcripts encoding EPHB receptor protein tyrosine kinases and their ephrin-B ligands in human small cell lung carcinoma", *Clin Cancer Res*, vol. 5, pp. 455-460.

Tang, X.X., et al., Jun. 1999, "High-level expression of *EPHB6*, *EFNB2*, and *EFNB3* is associated with low tumor stage and high *TrkA* expression in human neuroblastomas", *Clin Cancer Res*, vol. 5, pp. 1491-1496.

Tanga, M.J., et al., Jul.-Aug. 2003, "Synthesis of two potential food mutagens", *J. Heterocyclic Chemistry*, vol. 40, pp. 569-573.

Taraboletti et al., Feb. 15, 1995, "Inhibition of angiogenesis and murine hemangioma growth by batimastat, a synthetic inhibitor of matrix metalloproteinases", *J. Natl. Cancer Inst.*, vol. 87, No. 4, pp. 293-298.

Temple, C., et al., 1989, "New anticancer agents: alterations of the carbamate group of ethyl (5-amino-1,2-dihydro-3-phenylpyrido[3,4-b]pyrazin-7-yl) carbamates", *J. Med. Chem.*, vol. 32, pp. 2363-2367.

Terao, Y., et al., 1977, "Synthesis of α-thio, α-sulfinyl, and α-sulfonyl-substituted nitrosamines", *Chem. Pharm. Bull.*, vol. 25(11), pp. 2964-2968.

Thornber, C. W., 1979, "Isosterism and molecular modification in drug design", *Chemical Society Reviews*, vol. 8, No. 4, pp. 563-580.

Uchida, M., et al., 1985, "Studies on 2(1*H*)-quinolinone derivatives as gastric antiulcer active agents. 2-(4-chlorobenzoylamino)-3-[2(1*H*)-quinolinon-4-yl]propionic acid and related compounds", *Chem. Pharm. Bull.*, vol. 33(9), pp. 3775-3786.

Wan, P., et al., Mar. 19, 2004, "Mechanism of activation of the RAF-ERK signalling pathway by oncogenic mutations of B-RAF", *Cell*, vol. 116, pp. 855-867.

Wang, H.U., et al., May 29, 1998, "Molecular distinction and angiogenic interaction between embryonic arteries and veins revealed by ephrin-B2 and its receptor Eph-B4", *Cell*, vol. 93, pp. 741-753.

Wilks, A.F., 1990, "Structure and function of the protein tyrosine kinases", *Progress in Growth Factor Research*, vol. 2, pp. 97-111.

Yancopoulos et al., May 29, 1998, "Vasculogenesis, angiogenesis and growth factors: ephrins enter the fray at the border", *Cell*, vol. 93, pp. 661-664.

Yu et al., 2000, "Loss of fibroblast growth factor receptor 2 ligand-binding specificity in Apert syndrome", *Proc. Natl. Acad. Sci. U.S.A.*, vol. 97, pp. 14536-14541.

Zejc, A., et al., 1990, "Synthesis and anticonvulsant properties of some arylsuccinate methylpyridylimides", *Pol. J. Pharmaceol. Pharm.*, vol. 42, pp. 69-77.

Zhou, Z-L., et al., 2001, "Synthesis and SAR of 5-, 6-, 7- and 8-aza analogues of 3-aryl-4-hydroxyquinolin-2(1*H*)-one as NMDA/glycine site antagonists", Bioorganic & Medicinal Chemistry, vol. 9, pp. 2061-2071.

International Preliminary Report on Patentability (IPRP) for PCT/GB2005/004081 issued Apr. 24, 2007.

International Preliminary Report on Patentability (IPRP) for PCT/GB2007/001534 issued Oct. 28, 2008.

International Preliminary Report on Patentability (IPRP) for PCT/GB2008/004208 issued Jun. 22, 2010.

International Preliminary Report on Patentability (IPRP) for PCT/GB2009/001077 issued Oct. 26, 2010.

International Search Report (ISR) and Written Opinion of the International Searching Authority (WOISA) for PCT/GB2005/004081 mailed Feb. 2, 2006.

International Search Report (ISR) and Written Opinion of the International Searching Authority (WOISA) for PCT/GB2008/004208 mailed Mar. 5, 2009.

International Search Report (ISR) and Written Opinion of the International Searching Authority (WOISA) for PCT/GB2009/001077 Sep. 21, 2009.

International Search Report (ISR) for PCT/GB2007/001534 mailed Jun. 9, 2007.

UK Search Report for GB 0608268.9, dated Aug. 9, 2006.

UK Search Report for GB 0423554.5, dated Feb. 23, 2005.

US 8,383,816 B2

ARYL-QUINOLYL COMPOUNDS AND THEIR USE

RELATED APPLICATIONS

This application is a 35 U.S.C. §371 national phase application of PCT/GB2009/001077, filed Apr. 27, 2009 (WO 2009/130487) entitled "Aryl-Quinolyl Compounds and Their Use". PCT/GB2009/001077 is a non-provisional application of U.S. provisional patent application No. 61/047,902 filed Apr. 25, 2008 and United Kingdom patent application number 0807609.3 filed Apr. 25, 2008, the contents of both of which are incorporated herein by reference in their entirety.

TECHNICAL FIELD

The present invention pertains generally to the field of therapeutic compounds for treating proliferative disorders, cancer, etc., and more specifically to certain aryl-quinolyl compounds, as described herein, which, inter alia, inhibit RAF (e.g., B-RAF) activity. The present invention also pertains to pharmaceutical compositions comprising such compounds, and the use of such compounds and compositions, both in vitro and in vivo, to inhibit RAF (e.g., BRAF) activity, to inhibit receptor tyrosine kinase (RTK) activity, to inhibit cell proliferation, and in the treatment of diseases and disorders that are ameliorated by the inhibition of RAF, RTK, etc., proliferative disorders such as cancer (e.g., colorectal cancer, melanoma), etc.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

RAF, Proliferative Disorders, and Cancer

Mutations in genes that directly or indirectly control cell growth and differentiation are generally considered to be the main cause of cancer. Malignant tumors develop through a series of stepwise, progressive changes that lead to the loss of growth control characteristic of cancer cells, i.e., continuous unregulated proliferation, the ability to invade surrounding tissues, and the ability to metastasize to different organ sites. Carefully controlled in vitro studies have helped define the factors that characterize the growth of normal and neoplastic cells and have led to the identification of specific proteins that control cell growth and differentiation.

RAF is key downstream target for the ras GTPase and mediates the activation of the MAP kinase cascade consisting of raf-MEK-ERK. Activated ERK is a kinase that subsequently targets a number of proteins responsible for mediating, amongst other things, the growth, survival and transcriptional functions of the pathway. These include the transcription factors ELK1, C-JUN, the Ets family (including Ets 1, 2, and 7), and the FOS family. The ras-raf-MEK-ERK signal transduction pathway is activated in response to many cell stimuli including growth factors such as EGF, PDGF, KGF etc. Because the pathway is a major target for growth factor action, the activity of raf-MEK-ERK has been found to be upregulated in many factor dependent tumours. The observation that about 20% of all tumours have undergone an activating mutation in one of the ras proteins indicates that the pathway is more broadly important in tumorigenesis. There is growing evidence that activating mutations in other components of the pathway also occur in human tumours. This is true for RAF.

The RAF oncogene family includes three highly conserved genes termed A-RAF, B-RAF and C-RAF (also called Raf-1). RAF genes encode protein kinases that are thought to play important regulatory roles in signal transduction processes that regulate cell proliferation. RAF genes code for highly conserved serine-threonine-specific protein kinases, which are recruited to the plasma membrane following direct binding to the Ras small Guanine-nucleotide binding proteins and this is the initiating event in RAF activation. RAF proteins are part of a signal transduction pathway believed to consist of receptor tyrosine kinases, p21 Ras, RAF protein kinases, Mek1 (ERK activator or MAPKK) kinases and ERK (MAPK) kinases, which ultimately phosphorylate several cellular substrates, including transcription factors. Signaling through this pathway can mediate differentiation, proliferation or oncogenic transformation in different cellular contexts. Thus, RAF kinases are believed to play a fundamental role in the normal cellular signal transduction pathway, coupling a multitude of growth factors to their net effect, cellular proliferation. Because RAF proteins are direct downstream effectors of ras protein function, therapies directed against RAF kinases are believed to be useful in treatment of ras-dependent tumors.

The RAF kinases are differentially regulated and expressed; C-RAF is the most thoroughly characterized and is expressed in all organs and in all cell lines that have been examined. A-RAF and B-RAF also appear to be ubiquitous, but are most highly expressed in urogenital and brain tissues, respectively. Because B-RAF is highly expressed in neural tissues it was once thought to be limited to these tissues but it has since been found to be more widely expressed. Although all RAF proteins can bind to active Ras, B-raf is most strongly activated by oncogenic Ras, and may be the primary target of oncogenic Ras in transformed cells.

Recent evidence indicates that mutational activation of B-RAF is found in a number of different tumours including more than 65% of malignant melanomas, more than 10% of colorectal cancers (Davies, H., et al., 2002, *Nature*, Vol. 417, pp. 949-954; Rajagopalan, H. et al., 2002, *Nature*, Vol. 418, p.

934), ovarian cancers (Singer, G., et al., 2003, *J. Natl. Cancer Inst.*, Vol. 95, pp. 484-486) and papillary thyroid cancers (Brose, M., et al., 2002, *Cancer Res.*, Vol. 62, pp. 6997-7000; Cohen, Y., et al., 2003, *Invest. Ophthalmol. Vis. Sci.*, Vol. 44, pp. 2876-2878). A range of different B-RAF mutations have been identified in different tumours with the most common being a V600E mutation in the so-called activation loop of the kinase domain (Davies, H., et al., 2002, *Nature*, Vol. 417, pp. 949-954).

Other mutations of B-RAF found associated with human cancers may not necessarily activate B-RAF directly but do upregulate the activity of the ras-raf-MEK-ERK pathway by mechanisms which are not fully understood but may involve cross-talk with other RAF isoforms, such as A-RAF (Wan, P., et al., 2004, *Cell*, Vol. 116, pp. 855-867). In such cases, inhibition of RAF activity would remain a beneficial aim in cancer treatment.

In addition to link between B-RAF and certain cancers, there is a significant amount of evidence to indicate a more broad inhibition of RAF activity could be beneficial as an antitumour therapy. Blocking the pathway at the level of B-RAF would be effective at counteracting the upregulation of this pathway caused by tumourigenic ras mutations and also in tumours responding to growth factor action via this pathway. Genetic evidence in *Drosophila* and *C. elegans* indicates that RAF homologues are essential for ras dependent actions on differentiation (Dickson, B., et al., 1993, *Nature*, Vol. 360, pp. 600-603). Introduction of constitutively active MEK into NIH3T3 cells can have a transforming action whilst expression of dominant negative MEK proteins can suppress the tumourigenicity of ras transformed cell lines (Mansour, S. J., et al., 1994, *Science*, Vol. 265, pp. 966-970; Cowely, S., et al., 1994, *Cell*, Vol. 77, pp. 841-852). Expression of a dominant negative raf protein has also been found to inhibit ras dependent signalling as has suppression of raf expression using an antisense oligonucleotide construct (Koch, W., et al., 1991, *Nature*, Vol. 349, pp. 426-428; Bruder, T. T., et al., 1992, *Genes and Development*, Vol. 6, pp. 545-556).

This and other evidence suggests that inhibition of RAF (e.g., B-RAF) activity would be beneficial in the treatment of cancer, and that inhibition of RAF (e.g., B-RAF) activity could be particularly beneficial in those cancers containing a constitutively activated B-raf mutation.

The raf-MEK-ERK pathway functions downstream of many receptors and stimuli indicating a broad role in regulation of cell function. For this reason inhibitors of RAF may find utility in other disease conditions that are associated with upregulation of signalling via this pathway. The raf-MEK-ERK pathway is also an important component of the normal response of non-transformed cells to growth factor action. Therefore inhibitors of RAF may be of use in diseases where there is inappropriate or excessive proliferation of normal tissues. These include, but are not limited to glomerulonephritis and psoriasis. The cellular signalling pathway of which RAF is a part has also been implicated in inflammatory disorders characterized by T-cell proliferation (T-cell activation and growth), such as tissue graft rejection, endotoxin shock, and glomerular nephritis.

RAF (e.g., B-RAF) has been shown to be a valid therapeutic target in hyperproliferative disorders such as cancer. Activated versions of RAF (e.g., B-RAF) are able to transform mammalian cells, allowing them to take on the characteristics of cancer cells and the growth of these cells becomes dependent on the mutant RAF (e.g., B-RAF) protein. Inhibition of RAF (e.g., B-RAF) activity in human cancer cell lines that express the mutant forms of RAF (e.g., B-RAF) blocks their growth and ultimately induces their death.

Angiogenesis

Chronic proliferative diseases are often accompanied by profound angiogenesis, which can contribute to or maintain an inflammatory and/or proliferative state, or which leads to tissue destruction through the invasive proliferation of blood vessels. (Folkman, 1997, *EXS*, Vol. 79, pp. 1-81; Folkman, 1995, *Nature Medicine*, Vol. 1, pp. 27-31; Folkman and Shing, 1992, *J. Biol. Chem.*, Vol. 267, p. 10931.)

Angiogenesis is generally used to describe the development of new or replacement blood vessels, or neovascularisation. It is a necessary and physiological normal process by which the vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage (Colville-Nash and Scott, 1992, *Ann. Rhum. Dis.*, Vol. 51, p. 919). In diabetes (and in many different eye diseases), new vessels invade the macula or retina or other ocular structures, and may cause blindness (Brooks et al., 1994, *Cell*, Vol. 79, p. 1157). The process of atherosclerosis has been linked to angiogenesis (Kahlon et al., 1992, *Can. J. Cardiol.*, Vol. 8, p. 60). Tumor growth and metastasis have been found to be angiogenesis-dependent (Folkman, 1992, *Cancer Biol.*, Vol. 3, p. 65; Denekamp, 1993, *Br. J. Rad.*, Vol. 66, p. 181; Fidler and Ellis, 1994, *Cell*, Vol. 79, p. 185).

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis (O'Reilly et al., 1994, *Cell*, Vol. 79, p. 315; Ingber et al., 1990, Nature, Vol. 348, p. 555), ocular diseases (Friedlander et al., 1995, *Science*, Vol. 270, p. 1500), arthritis (Peacock et al., 1992, *J. Exp. Med.*, Vol. 175, p. 1135; Peacock et al., 1995, *Cell. Immun.*, Vol. 160, p. 178) and hemangioma (Taraboletti et al., 1995, *J. Natl. Cancer Inst.*, Vol. 87, p. 293).

RTKs

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified.

FGFR

The fibroblast growth factor (FGF) family of signaling polypeptides regulates a diverse array of physiologic functions including mitogenesis, wound healing, cell differentiation and angiogenesis, and development. Both normal and malignant cell growth as well as proliferation are affected by changes in local concentration of these extracellular signaling molecules, which act as autocrine as well as paracrine factors. Autocrine FGF signaling may be particularly important in the progression of steroid hormone-dependent cancers and to a hormone independent state (Powers et al., 2000, *Endocr. Relat. Cancer*, Vol. 7, pp. 165-197).

FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signaling in human pancreatic cancer (Ozawa et al., 2001, *Teratog. Carcinog. Mutagen.*, Vol. 21, pp. 27-44).

The two prototypic members are acidic fibroblast growth factor (aFGF or FGF1) and basic fibroblast growth factors (bFGF or FGF2), and to date, at least twenty distinct FGF family members have been identified. The cellular response to FGFs is transmitted via four types of high affinity transmembrane tyrosine-kinase fibroblast growth factor receptors numbered 1 to 4 (FGFR-1 to FGFR-4). Upon ligand binding, the receptors dimerize and auto- or trans-phosphorylate specific cytoplasmic tyrosine residues to transmit an intracellular signal that ultimately reaches nuclear transcription factor effectors.

Disruption of the FGFR-1 pathway should affect tumor cell proliferation since this kinase is activated in many tumor types in addition to proliferating endothelial cells. The overexpression and activation of FGFR-1 in tumor-associated vasculature has suggested a role for these molecules in tumor angiogenesis.

FGFR-2 has high affinity for the acidic and/or basic fibroblast growth factors, as well as the keratinocyte growth factor ligands. FGFR-2 also propagates the potent osteogenic effects of FGFs during osteoblast growth and differentiation. Mutations in FGFR-2, leading to complex functional alterations, were shown to induce abnormal ossification of cranial sutures (craniosynostosis), implying a major role of FGFR signaling in intramembraneous bone formation. For example, in Apert (AP) syndrome, characterized by premature cranial suture ossification, most cases are associated with point mutations engendering gain-of-function in FGFR-2 (Lemonnier et al., 2001, *J. Bone Miner. Res.*, Vol. 16, pp. 832-845).

Several severe abnormalities in human skeletal development, including Apert, Crouzon, Jackson-Weiss, Beare-Stevenson cutis gyrata, and Pfeiffer syndromes are associated with the occurrence of mutations in FGFR-2. Most, if not all, cases of Pfeiffer Syndrome (PS) are also caused by de novo mutation of the FGFR-2 gene (Meyers et al., 1996, *Am. J. Hum. Genet.*, Vol. 58, pp. 491-498; Plomp et al., 1998, *Am. J. Med. Genet.*, Vol. 75, 245-251), and it was recently shown that mutations in FGFR-2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signaling and suggests that the severe phenotypes of these disease syndromes result from ectopic ligand-dependent activation of FGFR-2 (Yu et al., 2000, *Proc. Natl. Acad. Sci. U.S.A.*, Vol. 97, pp. 14536-14541).

Activating mutations of the FGFR-3 receptor tyrosine kinase such as chromosomal translocations or point mutations produce deregulated, constitutively active, FGFR-3 receptors which have been involved in multiple myeloma and in bladder and cervix carcinomas (Powers, C. J., et al., 2000, *Endocr. Rel. Cancer*, Vol. 7, p. 165). Accordingly, FGFR-3 inhibition would be useful in the treatment of multiple myeloma, bladder and cervix carcinomas.

VEGFR

Vascular endothelial growth factor (VEGF), a polypeptide, is mitogenic for endothelial cells in vitro and stimulates angiogenic responses in vivo. VEGF has also been linked to inappropriate angiogenesis (Pinedo, H. M., et al., 2000, *The Oncologist*, Vol. 5 (90001), pp. 1-2). VEGFR(s) are protein tyrosine kinases (PTKs). PTKs catalyze the phosphorylation of specific tyrosyl residues in proteins involved in the regulation of cell growth and differentiation. (Wilks, A. F., 1990, *Progress in Growth Factor Research*, Vol. 2, pp. 97-111; Courtneidge, S. A., 1993, *Dev. Supp.I*, pp. 57-64; Cooper, J. A., 1994, *Semin. Cell Biol.*, Vol. 5(6), pp. 377-387; Paulson, R. F., 1995, *Semin. Immunol.*, Vol. 7(4), pp. 267-277; Chan, A. C., 1996, *Curr. Opin. Immunol.*, Vol. 8(3), pp. 394-401).

Three PTK receptors for VEGF have been identified: VEGFR-1 (Flt-1), VEGFR-2 (Flk-1 or KDR), and VEGFR-3 (Flt-4). These receptors are involved in angiogenesis and participate in signal transduction (Mustonen, T., et al., 1995, *J. Cell Biol.*, Vol. 129, pp. 895-898).

Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis (McMahon, G., 2000, *The Oncologist*, Vol. 5(90001), pp. 3-10).

Inhibition at the kinase domain binding site of VEGFR-2 would block phosphorylation of tyrosine residues and serve to disrupt initiation of angiogenesis.

TIE

Angiopoieten 1 (Ang1), a ligand for the endothelium-specific receptor tyrosine kinase TIE-2 is a novel angiogenic factor (Davis et al., 1996, *Cell*, Vol. 87, pp. 1161-1169; Partanen et al., 1992, *Mol. Cell. Biol.*, Vol. 12, pp. 1698-1707; U.S. Pat. Nos. 5,521,073; 5,879,672; 5,877,020; and 6,030,831). The acronym TIE represents "tyrosine kinase containing Ig and EGF homology domains". TIE is used to identify a class of receptor tyrosine kinases, which are exclusively expressed in vascular endothelial cells and early hemopoietic cells. Typically, TIE receptor kinases are characterized by the presence of an EGF-like domain and an immunoglobulin (IG) like domain, which consists of extracellular folding units, stabilized by intra-chain disulfide bonds (Partanen et al., 1999, *Curr. Topics Microbiol. Immunol.*, Vol. 237, pp. 159-172). Unlike VEGF, which functions during the early stages of vascular development, Ang1 and its receptor TIE-2 function in the later stages of vascular development, i.e., during vascular remodelling (remodelling refers to formation of a vascular lumen) and maturation (Yancopoulos et al., 1998, *Cell*, Vol. 93, pp. 661-664; Peters, K. G., 1998, *Circ. Res.*, Vol. 83(3), pp. 342-343; Suri et al., 1996, *Cell*, Vol. 87, pp. 1171-1180).

Consequently, inhibition of TIE-2 would be expected to serve to disrupt remodelling and maturation of new vasculature initiated by angiogenesis thereby disrupting the angiogenic process.

Eph

The largest subfamily of receptor tyrosine kinases (RTKs), the Eph family, and their ligands (ephrins), play important roles in physiologic and pathologic vascular processes. Both the Ephs (receptors) and ephrins (ligands) are divided into two groups, A and B subfamilies (Eph Nomenclature Committee, 1997). The binding of ephrin ligands to Eph receptors is dependent on cell-cell interactions. The interactions of ephrins and Ephs have recently been shown to function via bi-directional signalling. The ephrins binding to Eph receptors initiate phosphorylation at specific tyrosine residues in the cytoplasmic domain of the Eph receptors. In response to Eph receptor binding, the ephrin ligand also undergoes tyrosine phosphorylation, so-called 'reverse' signalling (Holland, S. J., et al., 1996, *Nature*, Vol. 383, pp. 722-725; Bruckner et al., 1997, *Science*, Vol. 275, pp. 1640-1643).

Eph RTKs and their ephrin ligands play important roles in embryonic vascular development. Disruption of specific Eph receptors and ligands (including ephrin-B2) leads to defective vessel remodelling, organisation, and sprouting resulting in embryonic death (Wang, H. U., at al., 1998, *Cell*, Vol. 93, pp. 741-753; Adams, R. H., et al., 1999, *Genes Dev*, Vol. 13, pp. 295-306; Gale and Yancopoulos, 1999, *Genes Dev*, Vol. 13, pp. 1055-1066; Helbling, P. M., et al., 2000, *Development*, Vol. 127, pp. 269-278). Coordinated expression of the Eph/ephrin system determines the phenotype of embryonic vascular structures: ephrin-B2 is present on arterial endothelial cells (ECs), whereas EphB4 is present on venous ECs (Gale and Yancopoulos, 1999, *Genes Dev*, Vol. 13, pp. 1055-1066; Shin, D., et al., 2001, *Dev Biol*, Vol. 230, pp. 139-150). Recently, specific Ephs and ephrins have been implicated in tumour growth and angiogenesis.

The Ephs and ephrins have been found to be overexpressed in many human tumours. In particular, the role of EphB2 has been identified in small cell lung carcinoma (Tang, X. X., at al., 1999, *Clin Cancer Res*, Vol. 5, pp. 455-460), human neuroblastomas (Tang, X. X., et al., 1999, *Clin Cancer Res*, Vol. 5, pp. 1491-1496) and colorectal cancers (Liu, W., at al., 2004, *Brit. J. Canc.*, Vol. 90, pp. 1620-1626), and higher expression levels of Ephs and ephrins, including EphB2, have been found to correlate with more aggressive and metastatic tumours (Nakamoto, M. and Bergemann, A. D., 2002, *Microsc. Res Tech*, Vol. 59, pp. 58-67).

Consequently, inhibition of EphB2 would be expected to serve to disrupt angiogenesis, and in particular in certain tumours where over-expression occurs.

The inventors have discovered compounds that, e.g., inhibit RAF (e.g., B-RAF) activity and/or are useful in the treatment of, e.g., proliferative disorders, cancer, etc.

SUMMARY OF THE INVENTION

One aspect of the invention pertains to certain arylquinolyl compounds (referred to herein as "AQ compounds"), as described herein.

Another aspect of the invention pertains to a composition (e.g., a pharmaceutical composition) comprising an AQ compound, as described herein, and a pharmaceutically acceptable carrier or diluent.

Another aspect of the invention pertains to method of preparing a composition (e.g., a pharmaceutical composition) comprising the step of admixing an AQ compound, as described herein, and a pharmaceutically acceptable carrier or diluent.

Another aspect of the present invention pertains to a method of inhibiting RAF (e.g., B-RAF) activity in a cell, in vitro or in vivo, comprising contacting the cell with an effective amount of an AQ compound, as described herein.

Another aspect of the present invention pertains to a method of inhibiting receptor tyrosine kinase (RTK) activity, such as FGFR, Tie, VEGFR and/or Eph activity, for example, FGFR-1, FGFR-2, FGFR-3, Tie2, VEGFR-2 and/or EphB2 activity, in a cell, in vitro or in vivo, comprising contacting the cell with an effective amount of an AQ compound, as described herein.

Another aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of an AQ compound, as described herein.

Another aspect of the present invention pertains to a method of treatment comprising administering to a subject in need of treatment a therapeutically-effective amount of an AQ compound, as described herein, preferably in the form of a pharmaceutical composition.

Another aspect of the present invention pertains to an AQ compound, as described herein, for use in a method of treatment of the human or animal body by therapy.

Another aspect of the present invention pertains to an AQ compound, as described herein, for the use in a method of treatment of the human or animal body by therapy wherein said compound is used in combination with other pharmaceutically active substances Another aspect of the present invention pertains to use of an AQ compound, as described herein, in the manufacture of a medicament for use in treatment.

In one embodiment, the treatment is treatment of a disease or disorder (e.g., cancer) that is characterised by the upregulation and/or activation of RAF (e.g., B-RAF), and/or is ameliorated by the inhibition of RAF (e.g., B-RAF).

In one embodiment, the treatment is treatment of a disease or disorder (e.g., cancer) that is characterised by the upregulation and/or activation of a receptor tyrosine kinase (RTK), and/or is ameliorated by the inhibition of a receptor tyrosine kinase (RTK). Examples of RTKs include FGFR, Tie, VEGFR and/or Eph, for example, FGFR-1, FGFR-2, FGFR-3, Tie2, VEGFR-2 and/or EphB2.

In one embodiment, the treatment is treatment of a disease or disorder that is characterised by inappropriate, excessive, and/or undesirable angiogenesis.

In one embodiment, the treatment is treatment of a proliferative disorder.

In one embodiment, the treatment is treatment of cancer.

Another aspect of the present invention pertains to a kit comprising (a) an AQ compound, as described herein, preferably provided as a pharmaceutical composition and in a suitable container and/or with suitable packaging; and (b) instructions for use, for example, written instructions on how to administer the compound.

Another aspect of the present invention pertains to an AQ compound obtainable by a method of synthesis as described herein, or a method comprising a method of synthesis as described herein.

Another aspect of the present invention pertains to an AQ compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

One aspect of the present invention pertains to compounds selected from compounds of the following formulae and pharmaceutically acceptable salts, hydrates, and solvates thereof (for convenience, collectively referred to herein as "aryl-quinolyl compounds" and "AQ compounds"):

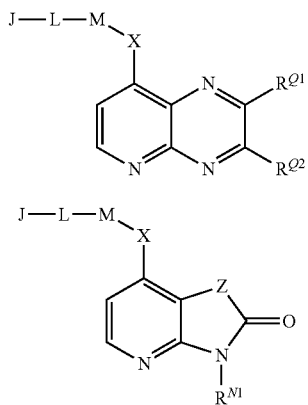

wherein:
—$R^{Q1}$ is independently —H or —$R^{Q1R}$;
wherein:
—$R^{Q1R}$ is independently:
—$R^1$, —$R^{1X}$, —Cl, —OH, —$OR^1$, —$OR^{1X}$, —SH, —$SR^1$, —$NH_2$, —$NHR^1$, —$NR^1_2$, or —$NR^{1NA}R^{1NB}$;
wherein:
each —$R^1$ is independently:
saturated aliphatic $C_{1-6}$alkyl, and is unsubstituted or substituted, for example, with one or more groups selected from —OH, —$OR^{11}$, —$NH_2$, —$NHR^{11}$, or —$NR^{11}_2$;
saturated $C_{3-6}$cycloalkyl, and is unsubstituted or substituted, for example, with one or more groups selected from —OH, —$OR^{11}$, —$NH_2$, —$NHR^{11}$, and —$NR^{11}_2$; or
azetidinyl, pyrrolidinyl, or piperidinyl, and is unsubstituted or substituted, for example, with one or more groups selected from —$R^{11}$;
and wherein:
each —$R^{1X}$, if present, is independently saturated aliphatic $C_{1-4}$alkyl substituted with one or more groups selected from —F, —Cl, —Br, and —I;
and wherein:
—$NR^{1NA}R^{1NB}$ is independently azetidino, pyrrolidino, piperidino, piperizino, morpholino, azepino, or diazepino, and is optionally substituted with one or more groups selected from —$R^{11}$, —$CF_3$, —F, —OH, —$OR^{11}$, —$NH_2$, —$NHR^{11}$, and —$NR^{11}_2$;

wherein:
each —$R^{11}$ is independently saturated aliphatic $C_{1-4}$alkyl;
and wherein:
—$R^{Q2}$ is independently —H or —$R^{Q2R}$;
wherein:
—$R^{Q2R}$ is independently:
—$R^2$, —$R^{2x}$, —Cl, —OH, —$OR^2$, —$OR^{2x}$, —SH, —$SR^2$, —$NH_2$, —$NHR^2$, —$NR^2_2$, or —$NR^{2NA}R^{2NB}$;
wherein:
each —$R^2$ is independently:
saturated aliphatic $C_{1-6}$alkyl, and is unsubstituted or substituted, for example, with one or more groups selected from —OH, —$OR^{22}$, —$NH_2$, —$NHR^{22}$, or —$NR^{22}_2$;
saturated $C_{3-6}$cycloalkyl, and is unsubstituted or substituted, for example, with one or more groups selected from —OH, —$OR^{22}$, —$NH_2$, —$NHR^{22}$, and —$NR^{22}_2$; or
azetidinyl, pyrrolidinyl, or piperidinyl, and is unsubstituted or substituted, for example, with one or more groups selected from —$R^{22}$;
and wherein:
each —$R^{2x}$, if present, is independently saturated aliphatic $C_{1-4}$alkyl substituted with one or more groups selected from —F, —Cl, —Br, and —I;
and wherein:
—$NR^{2NA}R^{2NB}$ is independently azetidino, pyrrolidino, piperidino, piperizino, morpholino, azepino, or diazepino, and is optionally substituted with one or more groups selected from —$R^{22}$, —$CF_3$, —F, —OH, —$OR^{22}$, —$NH_2$, —$NHR^{22}$, and —$NR^{22}_2$;
wherein:
each —$R^{22}$ is independently saturated aliphatic $C_{1-4}$alkyl;
and wherein:
—$R^{N1}$ is independently —H or saturated aliphatic $C_{1-4}$alkyl;
—Z— is independently —$NR^{N2}$— or —O—;
—$R^{N2}$ is independently —H or saturated aliphatic $C_{1-4}$alkyl optionally substituted with one or more groups selected from —$CF_3$, —F, —OH, —$OR^3$, —$NH_2$, —$NHR^3$, and —$NR^3_2$;
wherein each —$R^3$ is independently saturated aliphatic $C_{1-4}$alkyl;
and wherein:
—X— is independently —O— or —S—;
-M- is independently selected from:

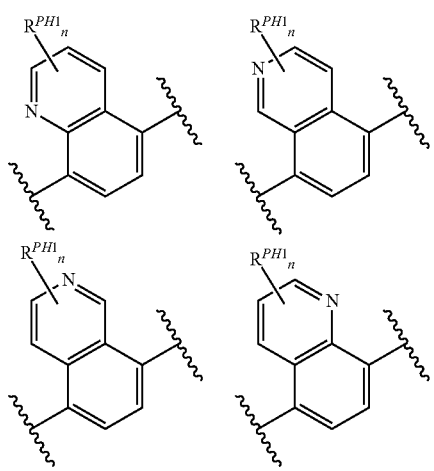

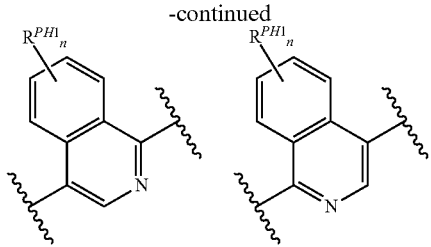

or -M- is independently selected from:

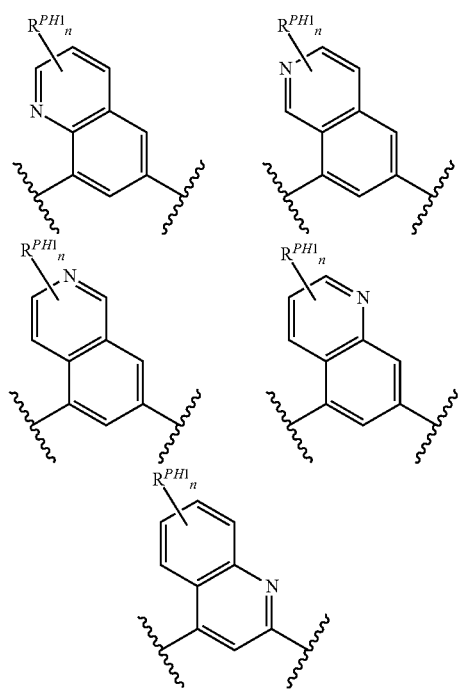

or -M- is independently selected from:

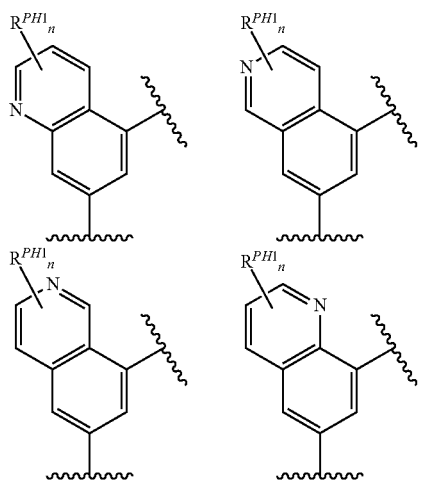

wherein:
each n is independently 0, 1 or 2; and
each $R^{PH1}$ is independently —F, —Cl, —Br, —I, —$R^4$, —OH, —SH, or —$SR^4$;

wherein each —$R^4$ is independently saturated aliphatic $C_{1-4}$alkyl;

J-L- is independently selected from:
J-$NR^{N3}$—C(=Y)—$NR^{N3}$—,
J-$CH_2$—$NR^{N3}$—C(=Y)—$NR^{N3}$—,
J-$NR^{N3}$—C(=Y)—$NR^{N3}$—$CH_2$—,
J-$NR^{N3}$—C(=Y)—,
J-$CH_2$—$NR^{N3}$—C(=Y)—,
J-$NR^{N3}$—C(=Y)—$CH_2$—,
J-$CH_2$—$NR^{N3}$—C(=Y)—$CH_2$—,
J-$CH_2$—$CH_2$—$NR^{N3}$—C(=Y)—,
J-$NR^{N3}$—C(=Y)—$CH_2$—$CH_2$—,
J-$NR^{N3}$—C(=Y)—$CH_2$—$NR^{N3}$—,
J-$NR^{N3}$—$CH_2$—$NR^{N3}$—C(=Y)—,
J-C(=Y)—N
J-$CH_2$—C(=Y)—N
J-C(=Y)—$NR^{N3}$—$CH_2$—,
J-$CH_2$—C(=Y)—$NR^{N3}$—$CH_2$—,
J-$CH_2$—$CH_2$—C(=Y)—$NR^{N3}$—,
J-C(=Y)—$NR^{N3}$—$CH_2$—$CH_2$—,
J-$NR^{N3}$—$CH_2$—C(=Y)—$NR^{N3}$—,
J-C(=Y)—$NR^{N3}$—$CH_2$—$NR^{N3}$—,
J-C(=Y)—$CH_2$—$NR^{N3}$—,
J-C(=Y)—$CH_2$—$NR^{N3}$—$CH_2$—,
J-C(=Y)—$CH_2$—$CH_2$—$NR^{N3}$—,
J-$CH_2$—C(=Y)—$CH_2$—$NR^{N3}$—,
J-$NR^{N3}$—$CH_2$—C(=Y)—,
J-$NR^{N3}$—$CH_2$—C(=Y)—$CH_2$—,
J-$NR^{N3}$—$CH_2$—$CH_2$—C(=Y)—,
J-$CH_2$—$NR^{N3}$—$CH_2$—C(=Y)—,
J-$NR^{N3}$—S(=O)$_2$—$NR^{N3}$—,
J-$NR^{N3}$—S(=O)$_2$—$NR^{N3}$—$CH_2$—,
J-$CH_2$—$NR^{N3}$—S(=O)$_2$—$NR^{N3}$—,
J-$NR^{N3}$—S(=O)$_2$—,
J-$NR^{N3}$—S(=O)$_2$—$CH_2$—,
J-$CH_2$—$NR^{N3}$—S(=O)$_2$—,
J-$CH_2$—$NR^{N3}$—S(=O)$_2$—$CH_2$—,
J-$CH_2$—$CH_2$—$NR^{N3}$—S(=O)$_2$—,
J-$NR^{N3}$—S(=O)$_2$—$CH_2$—$CH_2$—,
J-$NR^{N3}$—S(=O)$_2$—$CH_2$—$NR^{N3}$—,
J-$NR^{N3}$—$CH_2$—$NR^{N3}$—S(=O)$_2$—,
J-S(=O)$_2$—$NR^{N3}$—,
J-S(=O)$_2$—$NR^{N3}$—$CH_2$—,
J-$CH_2$—S(=O)$_2$—$NR^{N3}$—,
J-$CH_2$—S(=O)$_2$—$NR^{N3}$—$CH_2$—,
J-$CH_2$—$CH_2$—S(=O)$_2$—$NR^{N3}$—,
J-S(=O)$_2$—$NR^{N3}$—$CH_2$—$CH_2$—,
J-S(=O)$_2$—$NR^{N3}$—$CH_2$—$NR^{N3}$—, and
J-$NR^{N3}$—$CH_2$—S(=O)$_2$—$NR^{N3}$—;
wherein:
each —$R^{N3}$ is independently —H or saturated aliphatic $C_{1-4}$alkyl; and
each =Y is independently =O or =S; and
-J is independently phenyl or $C_{5-6}$heteroaryl, and is optionally substituted.

Pyrido[2,3-b]Pyrazines

In one embodiment, the compounds are related to pyrido[2,3-b]pyrazine:

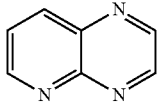

Pyrido[2,3-b]pyrazine

In one embodiment, the compounds are compounds selected from compounds of the following formula and pharmaceutically acceptable salts, hydrates, and solvates thereof:

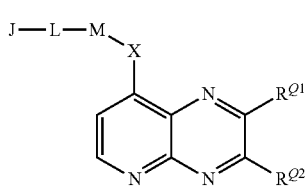

(1)

3H-Oxazole[4,5-b]pyridine-2-ones and 1H-imidazo[4,5-b]pyridine-2-ones

In one embodiment, the compounds are related to 3H-oxazole[4,5-b]pyridine-2-one and/or 1H-imidazo[4,5-b]pyridine-2-one:

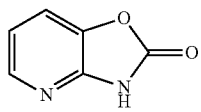 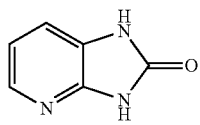

3H-Oxazolo[4,5-b]pyridin-2-one    1H-imidazo[4,5-b]pyridin-2-one

In one embodiment, the compounds are compounds selected from compounds of the following formula and pharmaceutically acceptable salts, hydrates, and solvates thereof:

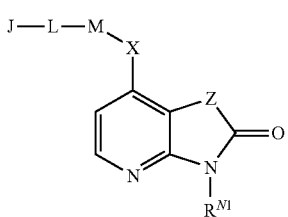

(2)

The Group —$R^{N1}$

In one embodiment, —$R^{N1}$, if present, is independently —H or saturated aliphatic $C_{1-4}$alkyl.

In one embodiment, —$R^{N1}$, if present, is independently —H or -Me.

In one embodiment, —$R^{N1}$, if present, is independently —H.

The Group —Z—

In one embodiment, —Z—, if present, is independently —$NR^{N2}$— or —O—.

In one embodiment, —Z—, if present, is independently —$NR^{N2}$—.

In one embodiment, —Z—, if present, is independently —O—.

The Group —$R^{N2}$

In one embodiment, —$R^{N2}$, if present, is independently —H or saturated aliphatic $C_{1-4}$alkyl optionally substituted with one or more groups selected from —$CF_3$, —F, —OH, —$OR^3$, —$NH_2$, —$NHR^3$, and —$NR^3_2$; wherein each —$R^3$ is independently saturated aliphatic $C_{1-4}$alkyl.

In one embodiment, each —$R^3$, if present, is independently saturated aliphatic $C_{1-4}$alkyl.

In one embodiment, each —$R^3$, if present, is independently saturated aliphatic $C_{1-3}$alkyl.

In one embodiment, each —$R^3$, if present, is independently -Me or -Et.

In one embodiment, —$R^{N2}$, if present, is independently —H or saturated aliphatic $C_{1-4}$alkyl.

In one embodiment, —$R^{N2}$, if present, is independently —H or -Me.

In one embodiment, —$R^{N2}$, if present, is independently —H.

The Group —$R^{Q1}$

In one embodiment, —$R^{Q1}$, if present, is independently —H or —$R^{Q1R}$.

In one embodiment, —$R^{Q1}$, if present, is independently —H.

In one embodiment, —$R^{Q1}$, if present, is independently —$R^{Q1R}$.

The Group —$R^{Q2}$

In one embodiment, —$R^{Q2}$, if present, is independently —H or —$R^{Q2R}$.

In one embodiment, —$R^{Q2}$, if present, is independently —H.

In one embodiment, —$R^{Q2}$, if present, is independently —$R^{Q2R}$.

The Group —$R^{Q1R}$

In one embodiment, —$R^{Q1R}$, if present, is independently: —$R^1$, —$R^{1X}$, —Cl, —OH, —$OR^1$, —$OR^{1X}$, —SH, —$SR^1$, —$NH_2$, —$NHR^1$, —$NR^1_2$, or —$NR^{1NA}R^{1NB}$.

In one embodiment, —$R^{Q1R}$, if present, is independently: —$R^1$, —Cl, —OH, —$OR^1$, —$OR^{1X}$, —SH, —$SR^1$, —$NH_2$, —$NHR^1$, —$NR^1_2$, or —$NR^{1NA}R^{1NB}$.

In one embodiment, —$R^{Q1R}$, if present, is independently: —$R^1$, —Cl, —OH, —SH, —$SR^1$, —$NH_2$, —$NHR^1$, —$NR^1_2$, or —$NR^{1NA}R^{1NB}$.

In one embodiment, —$R^{Q1R}$, if present, is independently: —$R^1$, —Cl, —SH, —$SR^1$, —$NH_2$, —$NHR^1$, —$NR^1_2$, or —$NR^{1NA}R^{1NB}$.

In one embodiment, —$R^{Q1R}$, if present, is independently: —OH, -Me, —$CF_3$, —$CH_2Br$, —$NH_2$, —NHMe, —$NMe_2$, morpholino, piperidino, or piperizino, or N-methyl-piperizino.

In one embodiment, —$R^{Q1R}$, if present, is independently: -Me, —$CF_3$, —$CH_2Br$, —$NH_2$, —NHMe, —$NMe_2$, morpholino, piperidino, or piperizino, or N-methyl-piperizino.

In one embodiment, —$R^{Q1R}$, if present, is independently: —OH, -Me, —$NH_2$, —NHMe, morpholino, piperidino, or piperizino, or N-methyl-piperizino.

In one embodiment, —$R^{Q1R}$, if present, is independently: -Me, —$NH_2$, —NHMe, morpholino, piperidino, piperizino, or N-methyl-piperizino.

In one embodiment, —$R^{Q1R}$, if present, is independently: —OH, -Me, or —$NH_2$.

In one embodiment, —R$^{Q1R}$, if present, is independently -Me or —NH$_2$.

In one embodiment, —R$^{Q1R}$, if present, is independently -Me.

In one embodiment, —R$^{Q1R}$, if present, is —OH. In this case, tautomerisation is possible, and the two equivalent tautomers are shown below.

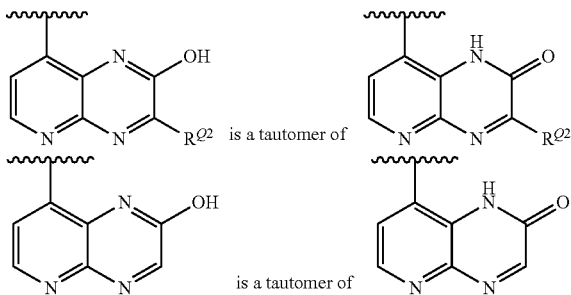

For the avoidance of doubt, unless otherwise specified, a reference to a particular tautomer is intended to encompass both that tautomer and corresponding equivalent tautomer(s).

The Group —R$^{Q2R}$

In one embodiment, —R$^{Q2R}$, if present, is independently: —R$^2$, —R$^{2x}$, —Cl, —OH, —OR$^2$, —OR$^{2x}$, —SH, —SR$^2$, —NH$_2$, —NHR$^2$, —NR$^2{}_2$, or —NR$^{2NA}$R$^{2NB}$.

In one embodiment, —R$^{Q2R}$, if present, is independently: —R$^2$, —R$^{2x}$, —Cl, —OR$^2$, —OR$^{2x}$, —SH, —SR$^2$, —NH$_2$, —NHR$^2$, —NR$^2{}_2$, or —NR$^{2NA}$R$^{2NB}$.

In one embodiment, —R$^{Q2R}$, if present, is independently: —R$^2$, —Cl, —OH, —OR$^2$, —SH, —SR$^2$, —NH$_2$, —NHR$^2$, —NR$^2{}_2$, or —NR$^{2NA}$R$^{2NB}$.

In one embodiment, —R$^{Q2R}$, if present, is independently: —R$^2$, —Cl, —OR$^2$, —SH, —SR$^2$, —NH$_2$, —NHR$^2$, —NR$^2{}_2$, or —NR$^{2NA}$R$^{2NB}$.

In one embodiment, —R$^{Q2R}$, if present, is independently: —OH, -Me, —CF$_3$, —CH$_2$Br, —NH$_2$, —NHMe, —NMe$_2$, morpholino, piperidino, or piperizino, or N-methyl-piperizino.

In one embodiment, —R$^{Q2R}$, if present, is independently: -Me, —CF$_3$, —CH$_2$Br, —NH$_2$, —NHMe, —NMe$_2$, morpholino, piperidino, or piperizino, or N-methyl-piperizino.

In one embodiment, —R$^{Q2R}$, if present, is independently: —OH, -Me, —NH$_2$, —NHMe, morpholino, piperidino, piperizino, or N-methyl-piperizino.

In one embodiment, —R$^{Q2R}$, if present, is independently: -Me, —NH$_2$, —NHMe, morpholino, piperidino, piperizino, or N-methyl-piperizino.

In one embodiment, —R$^{Q2R}$, if present, is independently —OH, -Me, or —NH$_2$.

In one embodiment, —R$^{Q2R}$, if present, is independently -Me or —NH$_2$.

In one embodiment, —R$^{Q2R}$, if present, is independently -Me.

In one embodiment, —R$^{Q2R}$, if present, is —OH. In this case, tautomerisation is possible, and the two equivalent tautomers are shown below.

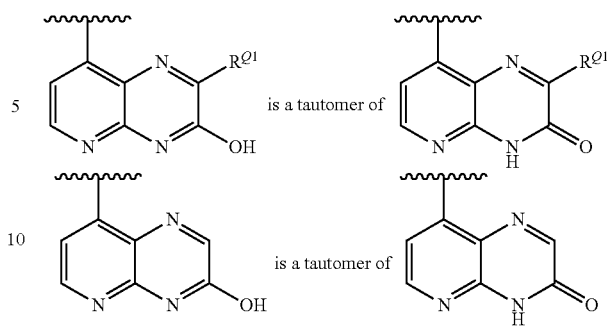

For the avoidance of doubt, unless otherwise specified, a reference to a particular tautomer is intended to encompass both that tautomer and corresponding equivalent tautomer(s).

Some Combinations of the Groups —R$^{Q1}$ and —R$^{Q2}$: Not both are —H

In one embodiment:
—R$^{Q1}$, if present, is independently —H or —R$^{Q1R}$; and
—R$^{Q2}$, if present, is independently —R$^{Q2R}$;
Or
—R$^{Q1}$, if present, is independently —R$^{Q1R}$; and
—R$^{Q2}$, if present, is independently —H or —R$^{Q2R}$.

Some Combinations of the Groups —R$^{Q1}$ and —R$^{Q2}$: At least one is —OH

In one embodiment:
—R$^{Q1}$, if present, is independently —R$^{Q1R}$;
—R$^{Q1R}$, if present, is independently —OH; and
—R$^{Q2}$, if present, is independently —H or —R$^{Q2R}$.

In one embodiment:
—R$^{Q1}$, if present, is independently —H or —R$^{Q1R}$;
—R$^{Q2}$, if present, is independently —R$^{Q2R}$; and
—R$^{Q2R}$, if present, is independently —OH.

Some Combinations of the Groups —R$^{Q1}$ and —R$^{Q2}$: Exactly one is —OH: —R$^{Q1}$ In one embodiment:
—R$^{Q1}$, if present, is independently —R$^{Q1R}$;
—R$^{Q1R}$, if present, is independently —OH;
—R$^{Q2}$, if present, is independently —H or —R$^{Q2R}$; and
—R$^{Q2R}$, if present, is independently:
—R$^2$, —R$^{2x}$, —Cl, —OR$^2$, —OR$^{2x}$, —SH, —SR$^2$, —NH$_2$, —NHR$^2$, —NR$^2{}_2$, or —NR$^{2NA}$R$^{2NB}$.

In one embodiment:
—R$^{Q1}$, if present, is independently —R$^{Q1R}$;
—R$^{Q1R}$, if present, is independently —OH;
—R$^{Q2}$, if present, is independently —H or —R$^{Q2R}$; and
—R$^{Q2R}$, if present, is independently:
—R$^2$, —Cl, —OR$^2$, —SH, —SR$^2$, —NH$_2$, —NHR$^2$, —NR$^2{}_2$, or —NR$^{2NA}$R$^{2NB}$.

In one embodiment:
—R$^{Q1}$, if present, is independently —R$^{Q1R}$;
—R$^{Q1R}$, if present, is independently —OH;
—R$^{Q2}$, if present, is independently —H or —R$^{Q2R}$; and
—R$^{Q2R}$, if present, is independently:
-Me, —CF$_3$, —CH$_2$Br, —NH$_2$, —NHMe, —NMe$_2$, morpholino, piperidino, or piperizino, or N-methyl-piperizino.

In one embodiment:
—R$^{Q1}$, if present, is independently —R$^{Q1R}$;
—R$^{Q1R}$, if present, is independently —OH;
—R$^{Q2}$, if present, is independently —H or —R$^{Q2R}$; and
—R$^{Q2R}$, if present, is independently:
-Me, —NH$_2$, —NHMe, morpholino, piperidino, piperizino, or N-methyl-piperizino.

In one embodiment:
- —$R^{Q1}$, if present, is independently —$R^{Q1R}$;
- —$R^{Q1R}$, if present, is independently —OH; and
- —$R^{Q2}$, if present, is independently —H.

In one embodiment:
- —$R^{Q1}$, if present, is independently —$R^{Q1R}$;
- —$R^{Q1R}$, if present, is independently —OH;
- —$R^{Q2}$, if present, is independently —$R^{Q2R}$; and
- —$R^{Q2R}$, if present, is independently:
  - —$R^2$, —$R^{2x}$, —Cl, —$OR^2$, —$OR^{2x}$, —SH, —$SR^2$, —$NH_2$, —$NHR^2$, —$NR^2_2$, or —$NR^{2NA}R^{2NB}$.

In one embodiment:
- —$R^{Q1}$, if present, is independently —$R^{Q1R}$;
- —$R^{Q1R}$, if present, is independently —OH;
- —$R^{Q2}$, if present, is independently —$R^{Q2R}$; and
- —$R^{Q2R}$, if present, is independently:
  - —$R^2$, —Cl, —$OR^2$, —SH, —$SR^2$, —$NH_2$, —$NHR^2$, —$NR^2_2$, or —$NR^{2NA}R^{2NB}$.

In one embodiment:
- —$R^{Q1}$, if present, is independently —$R^{Q1R}$;
- —$R^{Q1R}$, if present, is independently —OH;
- —$R^{Q2}$, if present, is independently —$R^{Q2R}$; and
- —$R^{Q2R}$, if present, is independently:
  - -Me, —$CF_3$, —$CH_2Br$, —$NH_2$, —NHMe, —$NMe_2$, morpholino, piperidino, or piperizino, or N-methyl-piperizino.

In one embodiment:
- —$R^{Q1}$, if present, is independently —$R^{Q1R}$;
- —$R^{Q1R}$, if present, is independently —OH;
- —$R^{Q2}$, if present, is independently —$R^{Q2R}$; and
- —$R^{Q2R}$, if present, is independently:
  - -Me, —$NH_2$, —NHMe, morpholino, piperidino, piperizino, or N-methyl-piperizino.

In one embodiment:
- —$R^{Q1}$, if present, is independently —$R^{Q1R}$;
- —$R^{Q1R}$, if present, is independently —OH;
- —$R^{Q2}$, if present, is independently —$R^{Q2R}$; and
- —$R^{Q2R}$, if present, is independently -Me or —$NH_2$.

In one embodiment:
- —$R^{Q1}$, if present, is independently —$R^{Q1R}$;
- —$R^{Q1R}$, if present, is independently —OH;
- —$R^{Q2}$, if present, is independently —$R^{Q2R}$; and
- —$R^{Q2R}$, if present, is independently -Me.

Some Combinations of the Groups —$R^{Q1}$ and —$R^{Q2}$: Exactly One is —OH: —$R^{Q2}$ In one embodiment:
- —$R^{Q1}$, if present, is independently —H or —$R^{Q1R}$;
- $R^{Q1R}$, if present, is independently:
  - —$R^1$, —$R^{1X}$, —Cl, —$OR^1$, —$OR^{1X}$, —SH, —$SR^1$, —$NH_2$, —$NHR^1$, —$NR^1_2$, or —$NR^{1NA}R^{1NB}$;
- —$R^{Q2}$, if present, is independently —$R^{Q2R}$; and
- —$R^{Q2R}$, if present, is independently —OH.

In one embodiment:
- —$R^{Q1}$, if present, is independently —H or —$R^{Q1R}$;
- $R^{Q1R}$, if present, is independently:
  - —$R^1$, —Cl, —SH, —$SR^1$, —$NH_2$, —$NHR^1$, —$NR^1_2$, or —$NR^{1NA}R^{1NB}$;
- —$R^{Q2}$, if present, is independently —$R^{Q2R}$; and
- —$R^{Q2R}$, if present, is independently —OH.

In one embodiment:
- —$R^{Q1}$, if present, is independently —H or —$R^{Q1R}$;
- —$R^{Q1R}$, if present, is independently:
  - -Me, —$CF_3$, —$CH_2Br$, —$NH_2$, —NHMe, —$NMe_2$, morpholino, piperidino, or piperizino, or N-methyl-piperizino;
- —$R^{Q2}$, if present, is independently —$R^{Q2R}$; and
- —$R^{Q2R}$, if present, is independently —OH.

In one embodiment:
- —$R^{Q1}$, if present, is independently —H or —$R^{Q1R}$;
- —$R^{Q1R}$, if present, is independently:
  - -Me, —$NH_2$, —NHMe, morpholino, piperidino, piperizino, or N-methyl-piperizino;
- —$R^{Q2}$, if present, is independently —$R^{Q2R}$; and
- —$R^{Q2R}$, if present, is independently —OH.

In one embodiment:
- —$R^{Q1}$, if present, is independently —H;
- —$R^{Q2}$, if present, is independently —$R^{Q2R}$; and
- —$R^{Q2R}$, if present, is independently —OH.

In one embodiment:
- —$R^{Q1}$, if present, is independently —$R^{Q1R}$;
- —$R^{Q1R}$, if present, is independently:
  - —$R^1$, —$R^{1X}$, —Cl, —$OR^1$, —$OR^{1X}$, —SH, —$SR^1$, —$NH_2$, —$NHR^1$, —$NR^1_2$, or —$NR^{1NA}R^{1NB}$;
- —$R^{Q2}$, if present, is independently —$R^{Q2R}$; and
- —$R^{Q2R}$, if present, is independently —OH.

In one embodiment:
- —$R^{Q1}$, if present, is independently —$R^{Q1R}$;
- —$R^{Q1R}$, if present, is independently:
  - —$R^1$, —Cl, —$OR^1$, —SH, —$SR^1$, —$NH_2$, —$NHR^1$, —$NR^1_2$, or —$NR^{1NA}R^{1NB}$;
- —$R^{Q2}$, if present, is independently —$R^{Q2R}$; and
- —$R^{Q2R}$, if present, is independently —OH.

In one embodiment:
- —$R^{Q1}$, if present, is independently —$R^{Q1R}$;
- —$R^{Q1R}$, if present, is independently:
  - -Me, —$CF_3$, —$CH_2Br$, —$NH_2$, —NHMe, —$NMe_2$, morpholino, piperidino, or piperizino, or N-methyl-piperizino;
- —$R^{Q2}$, if present, is independently —$R^{Q2R}$; and
- —$R^{Q2R}$, if present, is independently —OH.

In one embodiment:
- —$R^{Q1}$, if present, is independently —$R^{Q1R}$;
- —$R^{Q1R}$, if present, is independently:
  - -Me, —$NH_2$, —NHMe, morpholino, piperidino, piperizino, or N-methyl-piperizino;
- —$R^{Q2}$, if present, is independently —$R^{Q2R}$; and
- —$R^{Q2R}$, if present, is independently —OH.

In one embodiment:
- —$R^{Q1}$, if present, is independently —$R^{Q1R}$;
- —$R^{Q1R}$, if present, is independently -Me or —$NH_2$;
- —$R^{Q2}$, if present, is independently —$R^{Q2R}$; and
- —$R^{Q2R}$, if present, is independently —OH.

In one embodiment:
- —$R^{Q1}$, if present, is independently —$R^{Q1R}$;
- —$R^{Q1R}$, if present, is independently -Me;
- —$R^{Q2}$, if present, is independently —$R^{Q2R}$; and
- —$R^{Q2R}$, if present, is independently —OH.

Some Combinations of the Groups —$R^{Q1}$ and —$R^{Q2}$: Both are —OH

In one embodiment, —$R^{Q1}$, if present, is independently —$R^{Q1R}$; —$R^{Q1R}$, if present, is independently —OH; —$R^{Q2}$, if present, is independently —$R^{Q2R}$; and —$R^{Q2R}$, if present, is independently —OH. In this case, tautomerisation is possible, and the equivalent tautomers are shown below.

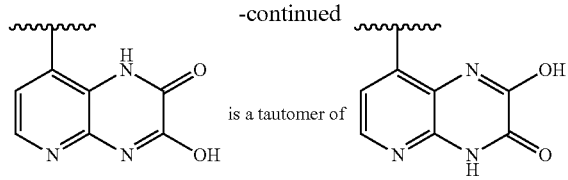

For the avoidance of doubt, unless otherwise specified, a reference to a particular tautomer is intended to encompass both that tautomer and corresponding equivalent tautomer(s).

The Group —$R^1$

In one embodiment, each —$R^1$, if present, is independently:
saturated aliphatic $C_{1-6}$alkyl, and is unsubstituted or substituted, for example, with one or more groups selected from —OH, —$OR^{11}$, —$NH_2$, —$NHR^{11}$, or —$NR^{11}_2$;
saturated $C_{3-6}$cycloalkyl, and is unsubstituted or substituted, for example, with one or more groups selected from —OH, —$OR^{11}$, —$NH_2$, —$NHR^{11}$, and —$NR^{11}_2$; or
azetidinyl, pyrrolidinyl, or piperidinyl, and is unsubstituted or substituted, for example, with one or more groups selected from —$R^{11}$.

In one embodiment, each —$R^1$, if present, is independently:
saturated aliphatic $C_{1-6}$alkyl, and is unsubstituted or substituted, for example, with one —$OR^{11}$, or more groups selected from —OH, —$OR^{11}$, —$NH_2$, or —$NR^{11}_2$; or
azetidinyl, pyrrolidinyl, or piperidinyl, and is unsubstituted or substituted, for example, with one or more groups selected from —$R^{11}$.

In one embodiment, each —$R^1$, if present, is independently:
saturated aliphatic $C_{1-6}$alkyl, and is unsubstituted or substituted, for example, with one or more groups selected from —OH, —$OR^{11}$, —$NH_2$, —$NHR^{11}$, or —$NR^{11}_2$.

In one embodiment, each —$R^1$, if present, is independently saturated aliphatic $C_{1-6}$alkyl.

In one embodiment, each —$R^1$, if present, is independently saturated aliphatic $C_{1-3}$alkyl.

The Group —$R^{1X}$

In one embodiment, each —$R^{1X}$, if present, is independently saturated aliphatic $C_{1-4}$alkyl substituted with one or more groups selected from —F, —Cl, —Br, and —I.

In one embodiment, each —$R^{1X}$, if present, is independently saturated aliphatic $C_{1-4}$alkyl substituted with one or more groups selected from —F or —Cl.

In one embodiment, each —$R^{1X}$, if present, is independently —$CF_3$ or —$CH_2Br$.

In one embodiment, each —$R^{1X}$, if present, is independently —$CF_3$.

The Group —$R^2$

In one embodiment, each —$R^2$, if present, is independently:
saturated aliphatic $C_{1-6}$alkyl, and is unsubstituted or substituted, for example, with one or more groups selected from —OH, —$OR^{22}$, —$NH_2$, —$NHR^{22}$, or —$NR^{22}_2$;
saturated $C_{3-6}$cycloalkyl, and is unsubstituted or substituted, for example, with one or more groups selected from —OH, —$OR^{22}$, —$NH_2$, —$NHR^{22}$, and —$NR^{22}_2$; or
azetidinyl, pyrrolidinyl, or piperidinyl, and is unsubstituted or substituted, for example, with one or more groups selected from —$R^{22}$.

In one embodiment, each —$R^2$, if present, is independently:
saturated aliphatic $C_{1-6}$alkyl, and is unsubstituted or substituted, for example, with one or more groups selected from —OH, —$OR^{22}$, —$NHR^{22}$, or —$NR^{22}_2$; or
azetidinyl, pyrrolidinyl, or piperidinyl, and is unsubstituted or substituted, for example, with one or more groups selected from —$R^{22}$.

In one embodiment, each —$R^2$, if present, is independently:
saturated aliphatic $C_{1-6}$alkyl, and is unsubstituted or substituted, for example, with one or more groups selected from —OH, —$OR^{22}$, —$NH_2$, —$NHR^{22}$, or —$NR^{22}_2$.

In one embodiment, each —$R^2$, if present, is independently saturated aliphatic $C_{1-6}$alkyl.

In one embodiment, each —$R^2$, if present, is independently saturated aliphatic $C_{1-3}$alkyl.

The Group —$R^{2X}$

In one embodiment, each —$R^{2x}$, if present, is independently saturated aliphatic $C_{1-4}$alkyl substituted with one or more groups selected from —F, —Cl, —Br, and —I.

In one embodiment, each —$R^{2x}$, if present, is independently saturated aliphatic $C_{1-4}$alkyl substituted with one or more groups selected from —F or —Cl.

In one embodiment, each —$R^{2x}$, if present, is independently —$CF_3$ or —$CH_2Br$.

In one embodiment, each —$R^{2x}$, if present, is independently —$CF_3$.

The Group —$NR^{1NA}R^{1NB}$

In one embodiment, —$NR^{1NA}R^{1NB}$, if present, is independently azetidino, pyrrolidino, piperidino, piperizino, morpholino, azepino, or diazepino, and is optionally substituted with one or more groups selected from —$R^{11}$, —$CF_3$, —F, —OH, —$OR^{11}$, —$NH_2$, —$NHR^{11}$, and —$NR^{11}_2$.

In one embodiment, —$NR^{1NA}R^{1NB}$, if present, is independently azetidino, pyrrolidino, piperidino, piperizino, morpholino, azepino, or diazepino, and is optionally substituted with one or more groups selected from —$R^{11}$.

In one embodiment, —$NR^{1NA}R^{1NB}$, if present, is independently pyrrolidino, piperidino, piperizino, or morpholino, and is optionally substituted with one or more groups selected from —$R^{11}$.

The Group —$NR^{2NA}R^{2NB}$

In one embodiment, —$NR^{2NA}R^{2NB}$, if present, is independently azetidino, pyrrolidino, piperidino, piperizino, morpholino, azepino, or diazepino, and is optionally substituted with one or more groups selected from —$R^{22}$, —$CF_3$, —F, —OH, —$OR^{22}$, —$NH_2$, —$NHR^{22}$, and —$NR^{22}_2$.

In one embodiment, —$NR^{2NA}R^{2NB}$, if present, is independently azetidino, pyrrolidino, piperidino, piperizino, morpholino, azepino, or diazepino, and is optionally substituted with one or more groups selected from —$R^{22}$.

In one embodiment, —$NR^{2NA}R^{2NB}$, if present, is independently pyrrolidino, piperidino, piperizino, or morpholino, and is optionally substituted with one or more groups selected from —$R^{22}$.

The Group —$R^{11}$

In one embodiment, each —$R^{11}$, if present, is independently saturated aliphatic $C_{1-4}$alkyl.

In one embodiment, each —$R^{11}$, if present, is independently saturated aliphatic $C_{1-3}$alkyl.

In one embodiment, each —$R^{11}$, if present, is independently -Me or -Et.

The Group —R²²

In one embodiment, each —R²², if present, is independently saturated aliphatic $C_{1-4}$alkyl.

In one embodiment, each —R²², if present, is independently saturated aliphatic $C_{1-3}$alkyl.

In one embodiment, each —R²², if present, is independently -Me or -Et.

The Group —X—

In one embodiment, —X— is independently —O— or —S—.

In one embodiment, —X— is independently —O—.

In one embodiment, —X— is independently —S—.

The Group -M-

The group -M- is related to quinoline or isoquinoline.

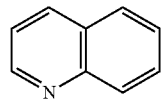
Quinoline

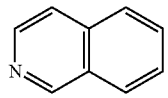
Isoquinoline

In one embodiment, -M- is independently selected from:

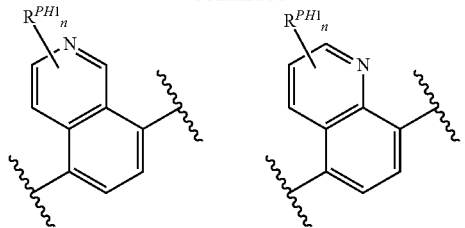

-continued

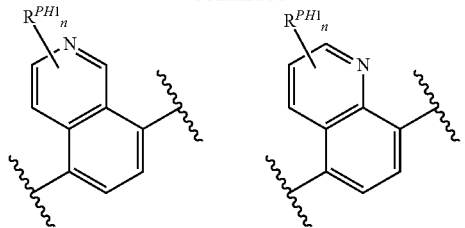

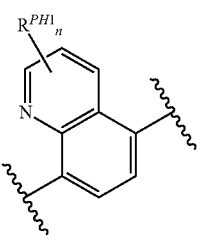

In one embodiment, -M- is independently selected from:

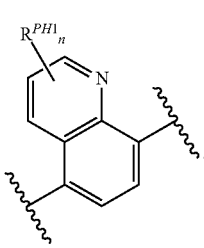

In one embodiment, -M- is independently:

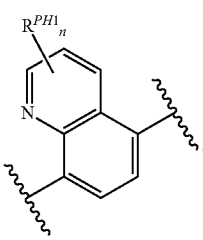

In one embodiment, -M- is independently selected from:

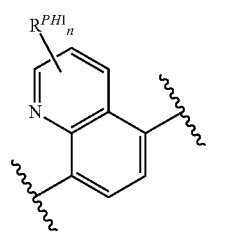 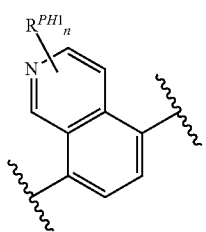

In one embodiment, -M- is independently:

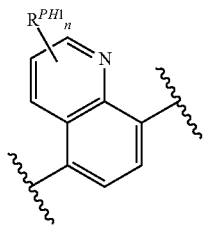

In one embodiment, -M- is independently selected from:

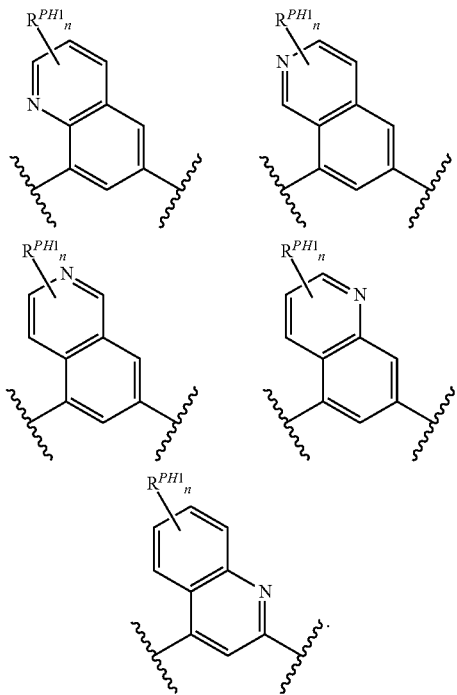

In one embodiment, -M- is independently:

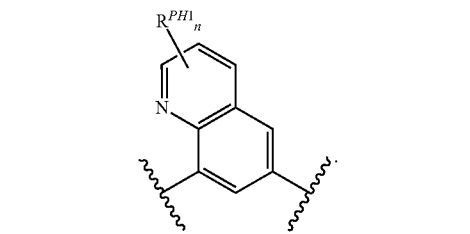

In one embodiment, -M- is independently selected from:

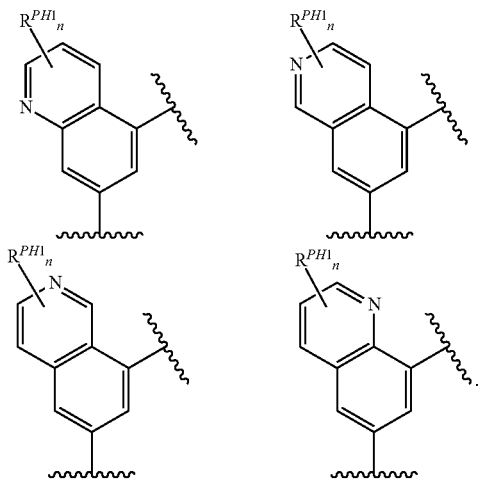

In one embodiment, -M- is independently:

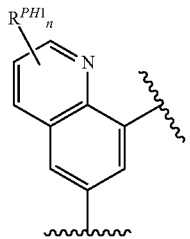

In one embodiment, each n is independently 0, 1 or 2.
In one embodiment, each n is independently 0 or 1.
In one embodiment, each n is independently 1 or 2.
In one embodiment, each n is independently 1.
In one embodiment, each n is independently 2.
In one embodiment, each n is independently 0, as in the following embodiments.

In one embodiment, -M- is independently selected from:

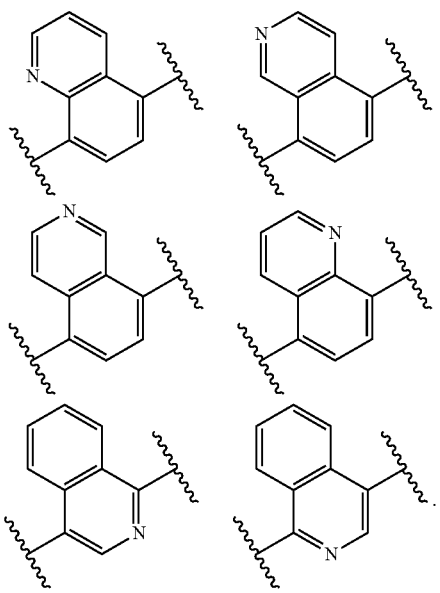

In one embodiment, -M- is independently selected from:

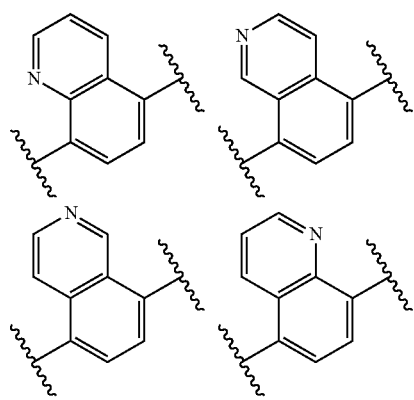

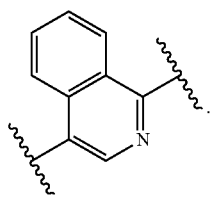

In one embodiment, -M- is independently selected from:

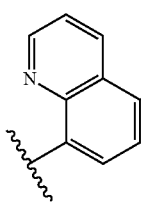 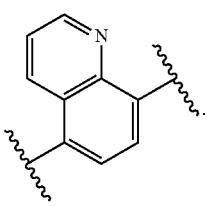

In one embodiment, -M- is independently selected from:

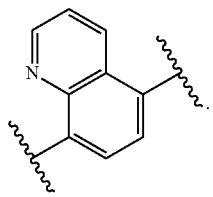 [SMILES: *c1ccc(*)c2ncccc12]

In one embodiment, -M- is independently selected from:

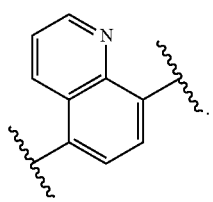 [SMILES: *c1ccc(*)c2ncccc12]

In one embodiment, -M- is independently selected from:

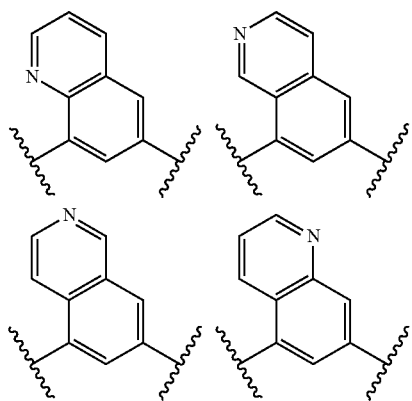

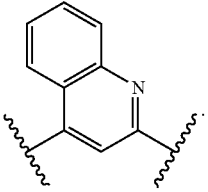

In one embodiment, -M- is independently selected from:

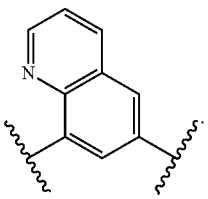 [SMILES: *c1cc(*)c2ncccc2c1]

In one embodiment, -M- is independently selected from:

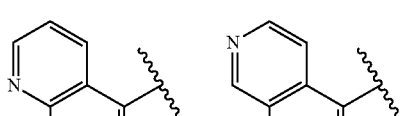
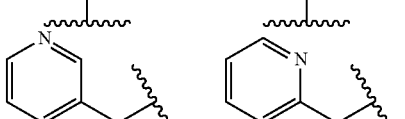

In one embodiment, -M- is independently selected from:

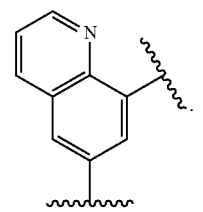 [SMILES: *c1cc(*)c2ncccc2c1]

The Groups —$R^{PH1}$

In one embodiment, each $R^{PH1}$, if present, is independently —F, —Cl, —Br, —I, —$R^4$, —OH, —$OR^4$, —SH, or —$SR^4$; wherein each —$R^4$ is independently saturated aliphatic $C_{1-4}$alkyl.

In one embodiment, each $R^{PH1}$, if present, is independently —F, —Cl, —Br, —I, —$R^4$, —OH, or —$OR^4$.

The Groups —$R^4$

In one embodiment, each —$R^4$, if present, is independently saturated aliphatic $C_{1-4}$alkyl.

In one embodiment, each —$R^4$, if present, is independently saturated aliphatic $C_{1-3}$alkyl.

In one embodiment, each —$R^4$, if present, is independently -Me.

The Group -L-

In one embodiment, J-L- is independently selected from:
J-NR$^{N3}$—C(=Y)—NR$^{N3}$—,
J-CH$_2$—NR$^{N3}$—C(=Y)—NR$^{N3}$—,
J-NR$^{N3}$—C(=Y)—NR$^{N3}$—CH$_2$—,
J-NR$^{N3}$—C(=Y)—,
J-CH$_2$—NR$^{N13}$—C(=Y)—,
J-NR$^{N3}$—C(=Y)—CH$_2$—,
J-CH$_2$—NR$^{N3}$—C(=Y)—CH$_2$—,
J-CH$_2$—CH$_2$—NR$^{N3}$—C(=Y)—,
J-NR$^{N3}$—C(=Y)—CH$_2$—CH$_2$—,
J-NR$^{N3}$—C(=Y)—CH$_2$—NR$^{N3}$—,
J-NR$^{N3}$—CH$_2$—NR$^{N3}$—C(=Y)—,
J-C(=Y)—NR$^{N3}$—,
J-CH$_2$—C(=Y)—NR$^{N3}$—,
J-C(=Y)—NR$^{N3}$—CH$_2$—,
J-CH$_2$—C(=Y)—NR$^{N3}$—CH$_2$—,
J-CH$_2$—CH$_2$—C(=Y)—NR$^{N3}$—,
J-C(=Y)—NR$^{N3}$—CH$_2$—CH$_2$—,
J-NR$^{N3}$—CH$_2$—C(=Y)—NR$^{N3}$—,
J-C(=Y)—NR$^{N3}$—CH$_2$—NR$^{N3}$—,
J-C(=Y)—CH$_2$—NR$^{N3}$—,
J-C(=Y)—CH$_2$—NR$^{N3}$—CH$_2$—,
J-C(=Y)—CH$_2$—CH$_2$—NR$^{N3}$—,
J-CH$_2$—C(=Y)—CH$_2$—NR$^{N3}$—,
J-NR$^{N3}$—CH$_2$—C(=Y)—,
J-NR$^{N3}$—CH$_2$—C(=Y)—CH$_2$—,
J-NR$^{N3}$—CH$_2$—CH$_2$—C(=Y)—,
J-CH$_2$—NR$^{N3}$—CH$_2$—C(=Y)—,
J-NR$^{N3}$—S(=O)$_2$—NR$^{N3}$—,
J-NR$^{N3}$—S(=O)$_2$—NR$^{N3}$—CH$_2$—,
J-CH$_2$—NR$^{N3}$—S(=O)$_2$—NR$^{N3}$—,
J-NR$^{N3}$—S(=O)$_2$—,
J-NR$^{N3}$—S(=O)$_2$—CH$_2$—,
J-CH$_2$—NR$^{N3}$—S(=O)$_2$—,
J-CH$_2$—NR$^{N3}$—S(=O)$_2$—CH$_2$—,
J-CH$_2$—CH$_2$—NR$^{N3}$—S(=O)$_2$—,
J-NR$^{N3}$—S(=O)$_2$—CH$_2$—CH$_2$—,
J-NR$^{N3}$—S(=O)$_2$—CH$_2$—NR$^{N3}$—,
J-NR$^{N3}$—CH$_2$—NR$^{N3}$—S(=O)$_2$—,
J-S(=O)$_2$—NR$^{N3}$—,
J-S(=O)$_2$—NR$^{N3}$—CH$_2$—,
J-CH$_2$—S(=O)$_2$—NR$^{N3}$—,
J-CH$_2$—S(=O)$_2$—NR$^{N3}$—CH$_2$—,
J-CH$_2$—CH$_2$—S(=O)$_2$—NR$^{N3}$—,
J-S(=O)$_2$—NR$^{N3}$—CH$_2$—CH$_2$—,
J-S(=O)$_2$—NR$^{N3}$—CH$_2$—NR$^{N3}$—, and
J-NR$^{N3}$—CH$_2$—S(=O)$_2$—NR$^{N3}$—;

wherein:
each —R$^{N3}$ is independently —H or saturated aliphatic C$_{1-4}$alkyl; and
each =Y is independently =O or =S.

In one embodiment, the group J-L- is independently selected from:
J-NR$^{N3}$—C(=Y)—NR$^{N3}$—,
J-CH$_2$—NR$^{N3}$—C(=Y)—NR$^{N3}$—,
J-NR$^{N3}$—C(=Y)—,
J-C(=Y)—NR$^{N3}$—,
J-NR$^{N3}$—CH$_2$—C(=Y)—NR$^{N3}$—,
J-CH$_2$—NR$^{N3}$—C(=Y)—; and
J-CH$_2$—C(=Y)—NR$^{N3}$—.

In one embodiment, the group J-L- is independently selected from:
J-NR$^{N3}$—C(=Y)—NR$^{N3}$—,
J-CH$_2$—NR$^{N3}$—C(=Y)—NR$^{N3}$—, and
J-NR$^{N3}$—C(=Y)—NR$^{N3}$—CH$_2$—.

In one embodiment, the group J-L- is independently selected from:
J-NR$^{N3}$—C(=Y)—NR$^{N3}$—, and
J-CH$_2$—C(=Y)—NR$^{N3}$—.

In one embodiment, the group J-L- is independently J-NR$^{N3}$—C(=Y)—NR$^{N3}$—.

In one embodiment, the group J-L- is independently J-CH$_2$—C(=Y)—NR$^{N3}$—.

In one embodiment, the group J-L- is independently J-NR$^{N3}$—C(=Y)— or J-C(=Y)—NR$^{N3}$—.

In one embodiment, the group J-L- is independently J-C(=Y)—NR$^{N3}$—.

In one embodiment, the group J-L- is independently J-NR$^{N3}$—C(=Y)—.

In one embodiment, the group J-L- is independently selected from:
J-NR$^{N13}$—C(=O)—NR$^{N3}$—, and
J-CH$_2$—C(=O)—NR$^{N3}$—.

In one embodiment, the group J-L- is independently J-NR$^{N3}$—C(=O)—NR$^{N3}$—.

In one embodiment, the group J-L- is independently J-NH—C(=O)—NH—.

In one embodiment, the group J-L- is independently J-CH$_2$—C(=O)—NR$^{N3}$—.

In one embodiment, the group J-L- is independently J-CH$_2$—C(=O)—NH—.

In one embodiment, the group J-L- is independently J-C(=O)—NR$^{N3}$—.

In one embodiment, the group J-L- is independently J-C(=O)—NH—.

In one embodiment, the group J-L- is independently J-NR$^{N3}$—C(=O)—.

In one embodiment, the group J-L- is independently J-NH—C(=O)—.

In one embodiment, the group J-L- is independently selected from:
A-NR$^{N3}$—S(=O)$_2$—NR$^{N3}$—,
A-NR$^{N3}$—S(=O)$_2$—,
A-S(=O)$_2$—NR$^{N3}$—,
A-CH$_2$—NR$^{N3}$—S(=O)$_2$—NR$^{N3}$—, and
A-CH$_2$—NR$^{N3}$—S(=O)$_2$—.

In one embodiment, the group J-L- is independently J-NR$^{N3}$—S(=O)$_2$— or J-S(=O)$_2$—NR$^{N3}$—.

In one embodiment, the group J-L- is independently J-S(=O)$_2$—NR$^{N3}$—.

In one embodiment, the group J-L- is independently J-S(=O)$_2$—NH—.

The Group —R$^{N3}$

In one embodiment, each —R$^{N3}$, if present, is independently —H or saturated aliphatic C$_{1-4}$alkyl.

In one embodiment, each —R$^{N3}$, if present, is independently —H or -Me.

In one embodiment, each —R$^{N3}$, if present, is independently —H.

The Group =Y

In one embodiment, each =Y, if present, is independently =O or =S.

In one embodiment, each =Y, if present, is independently =O ("ureas", "amides", etc.).

In one embodiment, each =Y, if present, is independently =S ("thioureas", "thioamides", etc.).

The Group -J

In one embodiment, -J is independently phenyl or C$_{5-6}$heteroaryl, and is optionally substituted.

In one embodiment, -J is independently phenyl, furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, and is optionally substituted.

In one embodiment, -J is independently phenyl, pyrazolyl, or pyridyl, and is optionally substituted.

In one embodiment, -J is independently phenyl or pyrazolyl, and is optionally substituted.

In one embodiment, -J is independently phenyl, and is optionally substituted.

In one embodiment, -J is independently pyrazolyl, and is optionally substituted.

In one embodiment, -J is independently 1H-pyrazolyl, and is optionally substituted.

In one embodiment, -J is independently 1H-pyrazol-5-yl, and is optionally substituted.

In one embodiment, -J is independently pyridyl, and is optionally substituted.

In one embodiment, -J is independently pyrid-3-yl, and is optionally substituted.

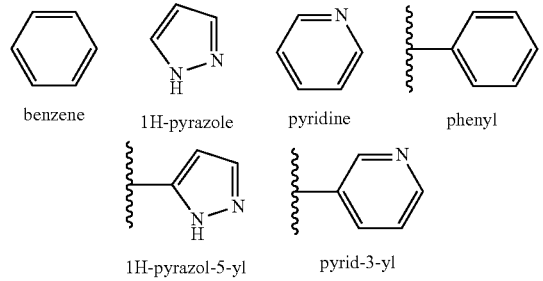

benzene   1H-pyrazole   pyridine   phenyl

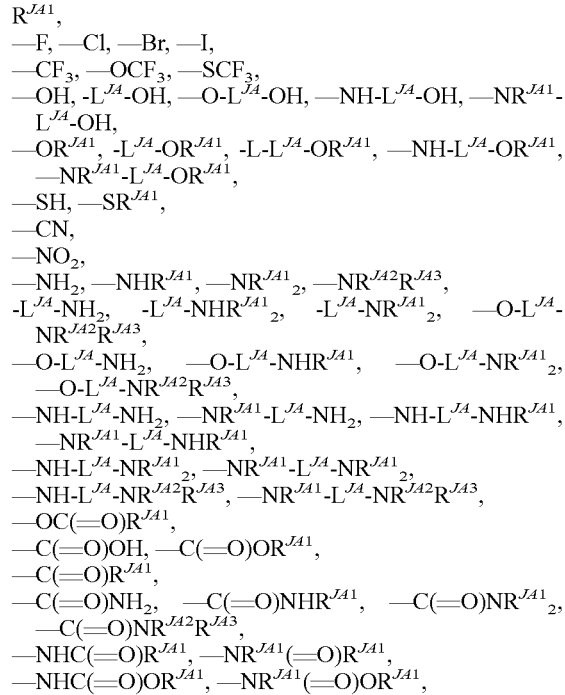

1H-pyrazol-5-yl   pyrid-3-yl

Optional Substituents on the Group -J

In one embodiment, -J is independently optionally substituted.

In one embodiment, -J is independently unsubstituted.

In one embodiment, -J is optionally substituted with one or more substituents, —$R^J$.

In one embodiment, each —$R^J$, if present, is independently selected from:
$R^{JA1}$,
—F, —Cl, —Br, —I,
—$CF_3$, —$OCF_3$, —$SCF_3$,
—OH, -$L^{JA}$-OH, —O-$L^{JA}$-OH, —NH-$L^{JA}$-OH, —$NR^{JA1}$-$L^{JA}$-OH,
—$OR^{JA1}$, -$L^{JA}$-$OR^{JA1}$, -L-$L^{JA}$-$OR^{JA1}$, —NH-$L^{JA}$-$OR^{JA1}$, —$NR^{JA1}$-$L^{JA}$-$OR^{JA1}$,
—SH, —$SR^{JA1}$,
—CN,
—$NO_2$,
—$NH_2$, —$NHR^{JA1}$, —$NR^{JA1}_2$, —$NR^{JA2}R^{JA3}$,
-$L^{JA}$-$NH_2$, -$L^{JA}$-$NHR^{JA1}$, -$L^{JA}$-$NR^{JA1}_2$, —O-$L^{JA}$-$NR^{JA2}R^{JA3}$,
—O-$L^{JA}$-$NH_2$, —O-$L^{JA}$-$NHR^{JA1}$, —O-$L^{JA}$-$NR^{JA1}_2$, —O-$L^{JA}$-$NR^{JA2}R^{JA3}$,
—NH-$L^{JA}$-$NH_2$, —$NR^{JA1}$-$L^{JA}$-$NH_2$, —NH-$L^{JA}$-$NHR^{JA1}$, —$NR^{JA1}$-$L^{JA}$-$NHR^{JA1}$,
—NH-$L^{JA}$-$NR^{JA1}_2$, —$NR^{JA1}$-$L^{JA}$-$NR^{JA1}_2$,
—NH-$L^{JA}$-$NR^{JA2}R^{JA3}$, —$NR^{JA1}$-$L^{JA}$-$NR^{JA2}R^{JA3}$,
—$OC(=O)R^{JA1}$,
—C(=O)OH, —$C(=O)OR^{JA1}$,
—$C(=O)R^{JA1}$,
—$C(=O)NH_2$, —$C(=O)NHR^{JA1}$, —$C(=O)NR^{JA1}_2$, —$C(=O)NR^{JA2}R^{JA3}$,
—$NHC(=O)R^{JA1}$, —$NR^{JA1}(=O)R^{JA1}$,
—$NHC(=O)OR^{JA1}$, —$NR^{JA1}(=O)OR^{JA1}$,
—$OC(=O)NH_2$, —$OC(=O)NHR^{JA1}$, —$OC(=O)NR^{JA1}_2$, —$OC(=O)NR^{JA2}R^{JA3}$,
—$NHC(=O)NH_2$, —$NHC(=O)NHR^{JA1}$,
—$NHC(=O)NR^{JA1}_2$, —$NHC(=O)NR^{JA2}R^{JA3}$,
—$NR^{JA1}(=O)NH_2$, —$NR^{JA1}(=O)NHR^{JA1}$,
—$NR^{JA1}(=O)NR^{JA1}_2$, —$NR^{JA1}(=O)NR^{JA2}R^{JA3}$,
—$NHS(=O)_2R^{JA1}$, —$NR^{JA1}S(=O)_2R^{JA1}$,
—$S(=O)_2NH_2$, —$S(=O)_2NHR^{JA1}$, —$S(=O)_2NR^{JA1}_2$,
—$S(=O)_2NR^{JA2}R^{JA3}$,
—$S(=O)R^{JA1}$, —$S(=O)_2R^{JA1}$, —$OS(=O)_2R^{JA1}$,
—$S(=O)_2OH$, and —$S(=O)_2OR^{JA1}$;
wherein:
each -$L^{JA}$- is independently saturated aliphatic $C_{1-5}$alkylene;
in each group —$NR^{JA2}R^{JA3}$, $R^{JA2}$ and $R^{JA3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
each —$R^{JA1}$ is independently:
—$R^{JB1}$, —$R^{JB2}$, —$R^{JB3}$, —$R^{JB4}$, —$R^{JB5}$, —$R^{JB6}$, —$R^{JB7}$, —$R^{JB8}$,
-$L^{JB}$-$R^{JB4}$, -$L^{JB}$-$R^{JB5}$, -$L^{JB}$-$R^{JB6}$, -$L^{JB}$-$R^{JB7}$, or -$L^{JB}$-$R^{JB8}$;
each —$R^{JB1}$ is independently saturated aliphatic $C_{1-6}$alkyl;
each —$R^{JB2}$ is independently aliphatic $C_{2-6}$alkenyl;
each —$R^{JB3}$ is independently aliphatic $C_{2-6}$alkynyl;
each —$R^{JB4}$ is independently saturated $C_{3-6}$cycloalkyl;
each —$R^{JB5}$ is independently $C_{3-6}$cycloalkenyl;
each —$R^{JB6}$ is independently non-aromatic $C_{3-8}$heterocyclyl;
each —$R^{JB7}$ is independently $C_{6-10}$carboaryl;
each —$R^{JB8}$ is independently $C_{6-10}$heteroaryl;
each -$L^{JB}$- is independently saturated aliphatic $C_{1-3}$alkylene;
wherein:
each —$R^{JB4}$, —$R^{JB5}$, —$R^{JB6}$, $R^{JB7}$, and —$R^{JB8}$ is optionally substituted, for example, with one or more substituents —$R^{JC1}$ and/or one or more substituents —$R^{JC2}$,
each —$R^{JB1}$, —$R^{JB2}$, —$R^{JB3}$, and -$L^{JB}$- is optionally substituted, for example, with one or more substituents —$R^{JC2}$, and
wherein:
each —$R^{JC1}$ is independently saturated aliphatic $C_{1-4}$alkyl, phenyl, or benzyl;
each —$R^{JC2}$ is independently:
—F, —Cl, —Br, —I,
—$CF_3$, —$OCF_3$, —$SCF_3$,
—OH, -$L^{JD}$-OH, —O-$L^{JD}$-OH,
—$OR^{JD1}$, -$L^{JD}$-$OR^{JD1}$, —O-$L^{JD}$-$OR^{JD1}$,
—SH,
—CN,
—$NO_2$,
—$NH_2$, —$NHR^{JD1}$, —$NR^{JD1}_2$, —$NR^{JD2}R^{JD3}$,
-$L^{JD}$-$NH_2$, -$L^{JD}$-$NHR^{JD1}$, -$L^{JD}$-$NR^{JD1}_2$, -$L^{JD}$-$NR^{JD2}R^{JD3}$,
—C(=O)OH, —$C(=O)OR^{JD1}$,
—$C(=O)NH_2$, —$C(=O)NHR^{JD1}$, —$C(=O)NR^{JD1}_2$, or —$C(=O)NR^{JD2}R^{JD3}$;
wherein:
each —$R^{JD1}$ is independently saturated aliphatic $C_{1-4}$alkyl, phenyl, or benzyl;
each -$L^{JD}$- is independently saturated aliphatic $C_{1-6}$alkylene; and in each group —NR$^{JD2}$R$^{JD3}$, R$^{JD2}$ and R$^{JD3}$, taken together with the nitrogen atom to which they are attached, form a 4-, 5-, 6-, or 7-membered non-aromatic ring heteroatom having exactly 1 ring heteroatom or exactly 2 ring heteroatoms, wherein one of said exactly 2 ring heteroatoms is N, and the other of said exactly 2 ring heteroatoms is independently N or O.

In one embodiment, each —R$^J$, if present, is independently selected from:
—R$^{JA1}$,
—F, —Cl, —Br, —I,
—CF$_3$, —OCF$_3$, —SCF$_3$,
—OH, -L$^{JA}$-OH, —O-L$^{JA}$-OH, —NH-L$^{JA}$-OH, —NR$^{JA1}$-L$^{JA}$-OH,
—OR$^{JA1}$, -L$^{JA}$-OR$^{JA1}$, —O-L$^{JA}$-OR$^{JA1}$, —NH-L$^{JA}$-OR$^{JA1}$, —NR$^{JA1}$-L$^{JA}$-OR$^{JA1}$,
—SH, —SR$^{JA1}$,
—CN,
—NO$_2$,
—NH$_2$, —NHR$^{JA1}$, —NR$^{JA1}{}_2$, —NR$^{JA2}$R$^{JA3}$,
-L$^{JA}$-NH$_2$, -L$^{JA}$-NHR$^{JA1}$, -L$^{JA}$-NR$^{JA1}{}_2$, -L$^{JA}$-NR$^{JA2}$R$^{JA3}$,
—O-L$^{JA}$-NH$_2$, —O-L$^{JA}$-NHR$^{JA1}$, —O-L$^{JA}$-NR$^{JA2}$R$^{JA3}$,
—NH-L$^{JA}$-NH$_2$, —NR$^{JA1}$-L$^{JA}$-NH$_2$, —NH-L$^{JA}$-NHR$^{JA1}$, —NR$^{JA1}$-L$^{JA}$-NHR$^{JA1}$,
—NH-L$^{JA}$-NR$^{JA1}{}_2$, —NR$^{JA1}$-L$^{JA}$-NR$^{JA1}{}_2$,
—NH-L$^{JA}$-NR$^{JA2}$R$^{JA3}$, —NR$^{JA1}$-L$^{JA}$-NR$^{JA2}$R$^{JA3}$,
—OC(=O)R$^{JA1}$,
—C(=O)OH, —C(=O)OR$^{JA1}$,
—C(=O)R$^{JA1}$,
—C(=O)NH$_2$, —C(=O)NHR$^{JA1}$, —C(=O)NR$^{JA1}{}_2$, —C(=O)NR$^{JA2}$R$^{JA3}$,
—NHC(=O)R$^{JA1}$, —NR$^{JA1}$(=O)R$^{JA1}$,
—NHC(=O)OR$^{JA1}$, —NR$^{JA1}$(=O)OR$^{JA1}$,
—OC(=O)NH$_2$, —OC(=O)NHR$^{JA1}$, —OC(=O)NR$^{JA1}{}_2$, —OC(=O)NR$^{JA2}$R$^{JA3}$,
—NHC(=O)NH$_2$, —NHC(=O)NHR$^{JA1}$,
—NHC(=O)NR$^{JA1}{}_2$, —NHC(=O)NR$^{JA2}$R$^{JA3}$,
—NR$^{JA1}$(=O)NH$_2$, —NR$^{JA1}$(=O)NHR$^{JA1}$,
—NR$^{JA1}$(=O)NR$^{JA1}{}_2$, —NR$^{JA1}$(=O)NR$^{JA2}$R$^{JA3}$,
—NHS(=O)$_2$R$^{JA1}$, —NR$^{JA1}$S(=O)$_2$R$^{JA1}$,
—S(=O)$_2$NH$_2$, —S(=O)$_2$NHR$^{JA1}$, —S(=O)$_2$NR$^{JA1}{}_2$, —S(=O)$_2$NR$^{JA2}$R$^{JA3}$,
—S(=O)R$^{JA1}$, and —S(=O)$_2$R$^{JA1}$.

In one embodiment, each —R$^J$, if present, is independently selected from:
—R$^{JA1}$,
—F, —Cl, —Br, —I,
—CF$_3$, —OCF$_3$, —SCF$_3$,
—OH, -L$^{JA}$-OH, —O-L$^{JA}$-OH, —NH-L$^{JA}$-OH, —NR$^{JA1}$-L$^{JA}$-OH,
—OR$^{JA1}$, -L$^{JA}$-OR$^{JA1}$, —O-L$^{JA}$-OR$^{JA1}$, —NH-L$^{JA}$-OR$^{JA1}$, —NR$^{JA1}$-L$^{JA}$-OR$^{JA1}$,
—CN,
—NH$_2$, —NHR$^{JA1}$, —NR$^{JA1}{}_2$, —NR$^{JA2}$R$^{JA3}$,
-L$^{JA}$-NH$_2$, -L$^{JA}$-NHR$^{JA1}$, -L$^{JA}$-NR$^{JA1}{}_2$, -L$^{JA}$-NR$^{JA2}$R$^{JA3}$,
—O-L$^{JA}$-NH$_2$, —O-L$^{JA}$-NHR$^{JA1}$, —O-L$^{JA}$-NR$^{JA1}{}_2$,
—O-L$^{JA}$-NR$^{JA2}$R$^{JA3}$,
—NH-L$^{JA}$-NH$_2$, —NR$^{JA1}$-L$^{JA}$-NH$_2$, —NH-L$^{JA}$-NHR$^{JA1}$, —NR$^{JA1}$-L$^{JA}$-NHR$^{JA1}$,
—NH-L$^{JA}$-NR$^{JA1}{}_2$, —NR$^{JA1}$-L$^{JA}$-NR$^{JA1}{}_2$,
—NH-L$^{JA}$-NR$^{JA2}$R$^{JA3}$, —NR$^{JA1}$-L$^{JA}$-NR$^{JA2}$R$^{JA3}$,
—C(=O)NH$_2$, —C(=O)NHR$^{JA1}$, —C(=O)NR$^{JA1}{}_2$, —C(=O)NR$^{JA2}$R$^{JA3}$,
—NHS(=O)$_2$R$^{JA1}$, —NR$^{JA1}$S(=O)$_2$R$^{JA1}$,
—S(=O)$_2$NH$_2$, —S(=O)$_2$NHR$^{JA1}$, —S(=O)$_2$NR$^{JA1}{}_2$,
—S(=O)$_2$NR$^{JA2}$R$^{JA3}$,
—S(=O)R$^{JA1}$, and —S(=O)$_2$R$^{JA1}$.

In one embodiment, each —R$^J$, if present, is independently selected from:
—R$^{JA1}$,
—F, —Cl, —Br, —I,
—CF$_3$, —OCF$_3$, —SCF$_3$,
—OH, -L$^{JA}$-OH, —O-L$^{JA}$-OH, —NH-L$^{JA}$-OH, —NR$^{JA1}$-L$^{JA}$-OH,
—OR$^{JA1}$, -L$^{JA}$-OR$^{JA1}$, —O-L$^{JA}$-OR$^{JA1}$, —NH-L$^{JA}$-OR$^{JA1}$, —NR$^{JA1}$-L$^{JA}$-OR$^{JA1}$,
—CN,
—NH$_2$, —NHR$^{JA1}$, —NR$^{JA1}{}_2$, —NR$^{JA2}$R$^{JA3}$,
—C(=O)NH$_2$, —C(=O)NHR$^{JA1}$, —C(=O)NR$^{JA1}{}_2$, —C(=O)NR$^{JA2}$R$^{JA3}$,
—S(=O)$_2$NH$_2$, —S(=O)$_2$NHR$^{JA1}$, —S(=O)$_2$NR$^{JA1}{}_2$, —S(=O)$_2$NR$^{JA2}$R$^{JA3}$.

In one embodiment, each -L$^{JA}$-, if present, is independently —(CH$_2$)$_{n2}$—, wherein n2 is independently 1 to 4.

In one embodiment, each -L$^{JA}$-, if present, is independently —CH$_2$— or —CH$_2$CH$_2$—.

In one embodiment, each —NR$^{JA2}$R$^{JA3}$, if present, is independently azetidino, pyrrolidino, imidazolidino, pyrazolidino, piperidino, piperazino, morpholino, azepino, or diazepino, and is optionally substituted, for example, with one or more groups selected from —R$^{JA4}$, —CF$_3$, —F, —OH, —OR$^{JA4}$, —NH$_2$, —NHR$^{JA4}$, and —NR$^{JA4}{}_2$; wherein each —R$^{JA4}$ is independently saturated aliphatic C$_{1-4}$alkyl.

In one embodiment, each —NR$^{JA2}$R$^{JA3}$, if present, is independently pyrrolidino, piperidino, piperazino, or morpholino, and is optionally substituted, for example, with one or more groups selected from —R$^{JA4}$, —CF$_3$, —F, —OH, —OR$^{JA4}$, —NH$_2$, —NHR$^{JA4}$, and —NR$^{JA4}{}_2$; wherein each —R$^{JA4}$ is independently saturated aliphatic C$_{1-4}$alkyl.

In one embodiment, each —NR$^{JA2}$R$^{JA3}$, if present, is independently pyrrolidino, piperidino, piperazino, or morpholino, and is optionally substituted, for example, with one or more groups selected from —R$^{JA4}$; wherein each —R$^{JA4}$ is independently saturated aliphatic C$_{1-4}$alkyl.

In one embodiment, each —R$^{JA1}$, if present, is independently:
—R$^{JB1}$, —R$^{JB4}$, —R$^{JB6}$, —R$^{JB7}$, —R$^{JB8}$,
-L$^{JB}$-R$^{JB4}$, -L$^{JB}$-R$^{JB6}$, -L$^{JB}$-R$^{JB7}$, or -L$^{JB}$-R$^{JB8}$.

In one embodiment, each —R$^{JA1}$, if present, is independently:
—R$^{JB1}$, —R$^{JB7}$, —R$^{JB8}$,
-L$^{JB}$-R$^{JB7}$, or -L$^{JB}$-R$^{JB8}$.

In one embodiment, each —R$^{JA1}$, if present, is independently:
—R$^{JB1}$, —R$^{JB7}$, or -L$^{JB}$-R$^{JB7}$.

In one embodiment, each —R$^{JB2}$, if present, is independently allyl.

In one embodiment, each —R$^{JB3}$, if present, is independently propargyl.

In one embodiment, each —R$^{JB4}$, if present, is independently cyclopropyl, cyclobutyl, cyclopentyl, or cyclohexyl.

In one embodiment, each —R$^{JB4}$, if present, is independently cyclopropyl.

In one embodiment, each —R$^{JB6}$, if present, is independently azetidinyl, pyrrolidinyl, imidazolidinyl, pyrazolidinyl, piperidinyl, piperazinyl, morpholinyl, azepinyl, diazepinyl, tetrahydrofuranyl, tetrahydropyranyl, dioxanyl, and is optionally substituted.

In one embodiment, each —R$^{JB6}$, if present, is independently pyrrolidinyl, piperidinyl, piperazinyl, morpholinyl, tetrahydrofuranyl, or tetrahydropyranyl, and is optionally substituted.

In one embodiment, each —R$^{JB7}$, if present, is independently phenyl, and is optionally substituted.

In one embodiment, each —$R^{JB8}$, if present, is independently $C_{5-6}$heteroaryl, and is optionally substituted.

In one embodiment, each —$R^{JB8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —$R^{JB8}$, if present, is independently $C_{9-10}$heteroaryl, and is optionally substituted.

In one embodiment, each —$R^{JB8}$, if present, is independently benzofuranyl, benzothienyl, benzopyrrolyl, benzoimidazolyl, benzopyrazolyl, benzotriazolyl, benzoxazolyl, benzoisoxazolyl, benzothiazolyl, benzoisothiazolyl, benzopyridyl, benzopyrimidinyl, or benzopyridazinyl, and is optionally substituted.

In one embodiment, each -$L^{JB}$-, if present, is independently —$CH_2$— or —$CH_2CH_2$—.

In one embodiment, each -$L^{JB}$-, if present, is independently —$CH_2$—.

In one embodiment, each —$R^{JC1}$, if present, is independently saturated aliphatic $C_{1-4}$alkyl.

In one embodiment, each —$R^{JC2}$ is independently:
- —F, —Cl, —Br, —I,
- —OH,
- —$OR^{JD1}$,
- —CN,
- —$NO_2$,
- —$NH_2$, —$NHR^{JD1}$, —$NR^{JD1}{}_2$, or —$NR^{JD2}R^{JD3}$.

In one embodiment, each —$R^{JD1}$, if present, is independently saturated aliphatic $C_{1-4}$alkyl.

In one embodiment, each -$L^{JD}$-, if present, is independently —$(CH_2)_{m2}$—, wherein m2 is independently 1 to 4.

In one embodiment, each -$L^{JD}$-, if present, is independently —$CH_2$— or —$CH_2CH_2$—.

In one embodiment, each —$NR^{JD2}R^{JD3}$, if present, is independently azetidino, pyrrolidino, imidazolidino, pyrazolidino, piperidino, piperazino, morpholino, azepino, or diazepino, and is optionally substituted, for example, with one or more groups selected from —$R^{J55}$, —$CF_3$, —F, —OH, —$OR^{J55}$, —$NH_2$, —$NHR^{J55}$, and —$NR^{J55}{}_2$; wherein each —$R^{J55}$ is independently saturated aliphatic $C_{1-4}$alkyl.

In one embodiment, each —$NR^{JD2}R^{JD3}$, if present, is independently pyrrolidino, piperidino, piperazino, or morpholino, and is optionally substituted, for example, with one or more groups selected from —$R^{J55}$, —$CF_3$, —F, —OH, —$OR^{J55}$, —$NH_2$, —$NHR^{J55}$, and —$NR^{J55}{}_2$; wherein each —$R^{J55}$ is independently saturated aliphatic $C_{1-4}$alkyl.

In one embodiment, each —$NR^{JD2}R^{JD3}$, if present, is independently pyrrolidino, piperidino, piperazino, or morpholino, and is optionally substituted, for example, with one or more groups selected from —$R^{J55}$; wherein each —$R^{J55}$ is independently saturated aliphatic $C_{1-4}$alkyl.

Some Preferred Optional Substituents on the Group -J

In one embodiment, each —$R^J$, if present, is independently selected from:
- —$R^6$,
- —F, —Cl, —Br, —I,
- —$CF_3$, —$OCF_3$, —$SCF_3$,
- —OH,
- —$OR^6$,
- —CN,
- —$NH_2$, —$NHR^6$, —$NR^6{}_2$, —$NR^{6NA}R^{6NB}$,
- —C(=O)$NH_2$, —C(=O)$NHR^6$, —C(=O)$NR^6{}_2$,
- —C(=O)$NR^{6NA}R^{6NB}$,
- —S(=O)$_2NH_2$, —S(=O)$_2NHR^6$, —S(=O)$_2NR^6{}_2$, and —S(=O)$_2NR^{6NA}R^{6NB}$;

wherein:

each —$R^6$ is independently:

saturated aliphatic $C_{1-6}$alkyl, and is unsubstituted or substituted, for example, with one or more groups selected from —OH, —$OR^{66}$, —$NH_2$, —$NHR^{66}$, —$NR^{66}{}_2$, or —$NR^{6NA}R^{6NB}$;

saturated $C_{3-6}$cycloalkyl, and is unsubstituted or substituted, for example, with one or more groups selected from —OH, —$OR^{66}$, —$NH_2$, —$NHR^{66}$, and —$NR^{66}{}_2$;

azetidinyl, pyrrolidinyl, or piperidinyl, and is unsubstituted or substituted, for example, with one or more groups selected from —$R^{66}$; or phenyl or $C_{5-6}$heteroaryl, and is optionally substituted, for example, optionally substituted with one or more substituents independently selected from —F, —Cl, —Br, —I, —$R^{66}$, —OH, —$OR^{66}$, —$CF_3$, —$OCF_3$;

and wherein:

each —$NR^{6NA}R^{6NB}$ is independently azetidino, pyrrolidino, piperidino, piperizino, morpholino, azepino, or diazepino, and is optionally substituted with one or more groups selected from —$R^{66}$, —$CF_3$, —F, —OH, —$NH_2$, —$NHR^{66}$, and —$NR^{66}{}_2$;

wherein:

each —$R^{66}$ is independently saturated aliphatic $C_{1-4}$alkyl.

In one embodiment, each —$R^6$, if present, is independently:

saturated aliphatic $C_{1-6}$alkyl, and is unsubstituted or substituted, for example, with one or more groups selected from —OH, —$OR^{66}$, —$NH_2$, —$NHR^{66}$, —$NR^{66}{}_2$, or —$NR^{6NA}R^{6NB}$;

azetidinyl, pyrrolidinyl, or piperidinyl, and is unsubstituted or substituted, for example, with one or more groups selected from —$R^{66}$; or phenyl or $C_{5-6}$heteroaryl, and is optionally substituted, for example, optionally substituted with one or more substituents independently selected from —F, —Cl, —Br, —I, —$R^{66}$, —OH, —$OR^{66}$, —$CF_3$, —$OCF_3$.

In one embodiment, each —$R^6$, if present, is independently:

saturated aliphatic $C_{1-6}$alkyl, and is unsubstituted or substituted, for example, with one or more groups selected from —OH, —$OR^{66}$, —$NH_2$, —$NHR^{66}$, —$NR^{66}{}_2$, or —$NR^{6NA}R^{6NB}$; or azetidinyl, pyrrolidinyl, or piperidinyl, and is unsubstituted or substituted, for example, with one or more groups selected from —$R^{66}$.

In one embodiment, each —$R^6$, if present, is independently:

saturated aliphatic $C_{1-6}$alkyl, and is unsubstituted or substituted, for example, with one or more groups selected from —OH, —$OR^{66}$, —$NH_2$, —$NHR^{66}$, —$NR^{66}{}_2$, or —$NR^{6NA}R^{6NB}$.

In one embodiment, each —$R^6$, if present, is independently saturated aliphatic $C_{1-6}$alkyl.

In one embodiment, each —$NR^{6NA}R^{6NB}$, if present, is independently pyrrolidino, piperidino, piperizino, or morpholino, and is optionally substituted with one or more groups selected from —$R^{66}$.

In one embodiment, each —$R^{66}$, if present, is independently saturated -Me or -Et.

Some Preferred Examples of the Group -J: Pyrazolyl

In one embodiment, -J is independently the following group, wherein each of $R^{PY1}$ and $R^{PY2}$ is independently a substituent as defined herein for —$R^J$:

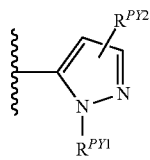

In one embodiment, -J is independently the following group, wherein each of $R^{PY1}$ and $R^{PY2}$ is independently a substituent as defined herein for —$R^J$:

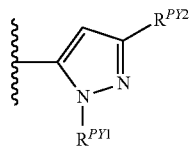

Some Preferred Examples of the Group -J: Pyrazolyl: The Group —$R^{PY1}$

In one embodiment:
— $R^{PY1}$ is independently phenyl or $C_{5-6}$heteroaryl, and is optionally substituted, for example, with one or more substituents —$R^{PZ1}$; or
— $R^{PY1}$ is independently saturated aliphatic $C_{1-6}$alkyl, aliphatic $C_{2-6}$alkenyl, aliphatic $C_{2-6}$alkynyl, saturated $C_{3-7}$cycloalkyl, or saturated $C_{3-7}$cycloalkyl-saturated aliphatic $C_{1-6}$alkyl, and is optionally substituted, for example, with one or more substituents —$R^{PZ2}$.

Some Preferred Examples of the Group -J: Pyrazolyl: The Group —$R^{PY1}$: Aryl

In one embodiment, —$R^{PY1}$ is independently phenyl or $C_{5-6}$heteroaryl, and is optionally substituted, for example, with one or more substituents —$R^{PZ1}$.

In one embodiment, —$R^{PY1}$ is independently phenyl, furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted, for example, with one or more substituents —$R^{PZ1}$.

In one embodiment, —$R^{PY1}$ is independently phenyl, thienyl, pyridyl, and is optionally substituted, for example, with one or more substituents —$R^{PZ1}$.

In one embodiment, —$R^{PY1}$ is independently phenyl or pyridyl, and is optionally substituted, for example, with one or more substituents —$R^{PZ1}$.

In one embodiment, —$R^{PY1}$ is independently phenyl, and is optionally substituted, for example, with one or more substituents —$R^{PZ1}$.

In one embodiment, —$R^{PY1}$ is independently pyridyl, and is optionally substituted, for example, with one or more substituents —$R^{PZ1}$.

In one embodiment, —$R^{PY1}$ is independently thienyl, and is optionally substituted, for example, with one or more substituents —$R^{PZ1}$.

In one embodiment, each —$R^{PZ1}$, if present, is independently selected from:
—F, —Cl, —Br, —I, —$R^{7A}$, —OH, —$OR^{7A}$, and —$S(=O)_2R^{7A}$.

In one embodiment, each —$R^{PZ1}$, if present, is independently selected from:
—F, —Cl, —Br, —I, —$R^{7A}$, —OH, and —$OR^{7A}$.

In one embodiment, each —$R^{PZ1}$, if present, is independently selected from:
—$R^{7A}$, —OH, and —$OR^{7A}$.

In one embodiment, each —$R^{7A}$, if present, is independently saturated aliphatic $C_{1-6}$alkyl.

In one embodiment, each —$R^{7A}$, if present, is independently saturated aliphatic $C_{1-4}$alkyl.

In one embodiment, each —$R^{7A}$, if present, is independently -Me.

Some Preferred Examples of the Group -J: Pyrazolyl: The Group —$R^{PY1}$: Other

In one embodiment, —$R^{PY1}$ is independently saturated aliphatic $C_{1-6}$alkyl, aliphatic $C_{2-6}$alkenyl, aliphatic $C_{2-6}$alkynyl, saturated $C_{3-7}$cycloalkyl, or saturated $C_{3-7}$cycloalkyl-saturated aliphatic $C_{1-6}$alkyl, and is optionally substituted, for example, with one or more substituents —$R^{PZ2}$.

In one embodiment, —$R^{PY1}$ is independently saturated aliphatic $C_{1-6}$alkyl, and is optionally substituted, for example, with one or more substituents —$R^{PZ2}$.

In one embodiment, —$R^{PY1}$ is independently aliphatic $C_{2-6}$alkenyl, and is optionally substituted, for example, with one or more substituents —$R^{PZ2}$.

In one embodiment, —$R^{PY1}$ is independently aliphatic $C_{2-6}$alkynyl, and is optionally substituted, for example, with one or more substituents —$R^{PZ2}$.

In one embodiment, —$R^{PY1}$ is independently saturated $C_{3-7}$cycloalkyl, and is optionally substituted, for example, with one or more substituents —$R^{PZ2}$.

In one embodiment, —$R^{PY1}$ is independently saturated $C_{3-7}$cycloalkyl-saturated aliphatic $C_{1-6}$alkyl, and is optionally substituted, for example, with one or more substituents —$R^{PZ2}$.

In one embodiment, each —$R^{PZ2}$, if present, is independently selected from:
—F, —Cl, —Br, —I, —OH, —$OR^{7B}$, —$NH_2$, —$NHR^{7B}$, and —$NR^{7B}_2$.

In one embodiment, each —$R^{PZ2}$, if present, is independently selected from:
—OH, —$OR^{7B}$, —$NH_2$, —$NHR^{7B}$, and —$NR^{7B}_2$.

In one embodiment, each —$R^{7B}$, if present, is independently saturated aliphatic $C_{1-6}$alkyl.

In one embodiment, each —$R^{7B}$, if present, is independently saturated aliphatic $C_{1-4}$alkyl.

In one embodiment, each —$R^{7B}$, if present, is independently -Me.

In one embodiment, —$R^{PY1}$ is independently saturated aliphatic $C_{1-6}$alkyl.

In one embodiment, —$R^{PY1}$ is -Me, -Et, -nPr, -iPr, -nBu, -iBu, -sBu, or -tBu.

In one embodiment, —$R^{PY1}$ is -Me.

In one embodiment, —$R^{PY1}$ is independently aliphatic $C_{2-6}$alkenyl.

In one embodiment, —$R^{PY1}$ is allyl.

In one embodiment, —$R^{PY1}$ is independently aliphatic $C_{2-6}$alkynyl.

In one embodiment, —$R^{PY1}$ is propargyl.

In one embodiment, —$R^{PY1}$ is independently saturated $C_{3-7}$cycloalkyl.

In one embodiment, —$R^{PY1}$ is independently cyclopropyl or cyclobutyl.

In one embodiment, —$R^{PY1}$ is independently cyclopropyl.

In one embodiment, —$R^{PY1}$ is independently saturated $C_{3-7}$cycloalkyl-saturated aliphatic $C_{1-6}$alkyl.

In one embodiment, —R$^{PY1}$ is independently cyclobutyl-methyl, cyclobutyl-ethyl, cyclopropyl-methyl, or cyclopropyl-ethyl.

Some Preferred Examples of the Group -J: Pyrazolyl: The Group —R$^{PY2}$

In one embodiment:

—R$^{PY2}$ is independently —F, —Cl, —Br, —I, —R$^8$, —OH, —OR$^8$, —CF$_3$, —OCF$_3$, —SCF$_3$, or optionally substituted phenyl, for example, phenyl optionally substituted with one or more substituents —R$^{PZ3}$;

wherein:

each —R$^8$ is independently saturated aliphatic C$_{1-6}$alkyl or saturated C$_{3-6}$cycloalkyl;

each —R$^{PZ3}$ is independently: —F, —Cl, —Br, —I, —R$^V$, —OH, —OR$^V$, —NH$_2$, —NHR$^V$, —NR$^V_2$, —NR$^{VNA}$R$^{VNB}$, —CN, —S(=O)$_2$NH$_2$, —S(=O)$_2$NHR$^V$, —S(=O)$_2$NR$^V_2$, —S(=O)$_2$NR$^{VNA}$R$^{VNB}$, or —C(=O)NR$^{VNA}$R$^{VNB}$;

wherein:

each —R$^V$ is independently:

saturated aliphatic C$_{1-6}$alkyl, and is unsubstituted or substituted, for example, with one or more groups selected from —OH, —OR$^W$, —NH$_2$, —NHR$^W$, and —NR$^W_2$;

saturated C$_{3-6}$cycloalkyl, and is unsubstituted or substituted, for example, with one or more groups selected from —OH, —OR$^W$, —NH$_2$, —NHR$^W$, and —NR$^W_2$; or azetidinyl, pyrrolidinyl, or piperidinyl, and is unsubstituted or substituted, for example, with one or more groups selected from —R$^W$;

and wherein:

—NR$^{VNA}$R$^{VNB}$ is independently azetidino, pyrrolidino, piperidino, piperizino, morpholino, azepino, or diazepino, and is optionally substituted with one or more groups selected from —R$^W$, —CF$_3$, —F, —OH, —OR$^W$, —NH$_2$, —NHR$^W$, and —NR$^W_2$;

wherein:

each —R$^W$ is independently saturated aliphatic C$_{1-4}$alkyl.

In one embodiment, R$^{PY2}$ is independently —F, —Cl, —Br, —I, —R$^8$, —OH, —OR$^8$, —CF$_3$, —OCF$_3$, —SCF$_3$.

In one embodiment, —R$^{PY2}$ is independently —R$^8$ or —CF$_3$.

In one embodiment, —R$^{PY2}$ is independently —R$^8$.

In one embodiment, each —R$^8$ is independently saturated aliphatic C$_{1-6}$alkyl.

In one embodiment, each —R$^8$ is independently saturated aliphatic C$_{1-4}$alkyl.

In one embodiment, each —R$^8$ is independently -tBu.

In one embodiment, —R$^{PY2}$ is independently saturated aliphatic C$_{1-6}$alkyl.

In one embodiment, —R$^{PY2}$ is independently saturated aliphatic C$_{1-4}$alkyl.

In one embodiment, —R$^{PY2}$ is independently -tBu.

Some Preferred Examples of the Group -J: Pyrazolyl: Specific Examples

In one embodiment, -J is independently selected from:

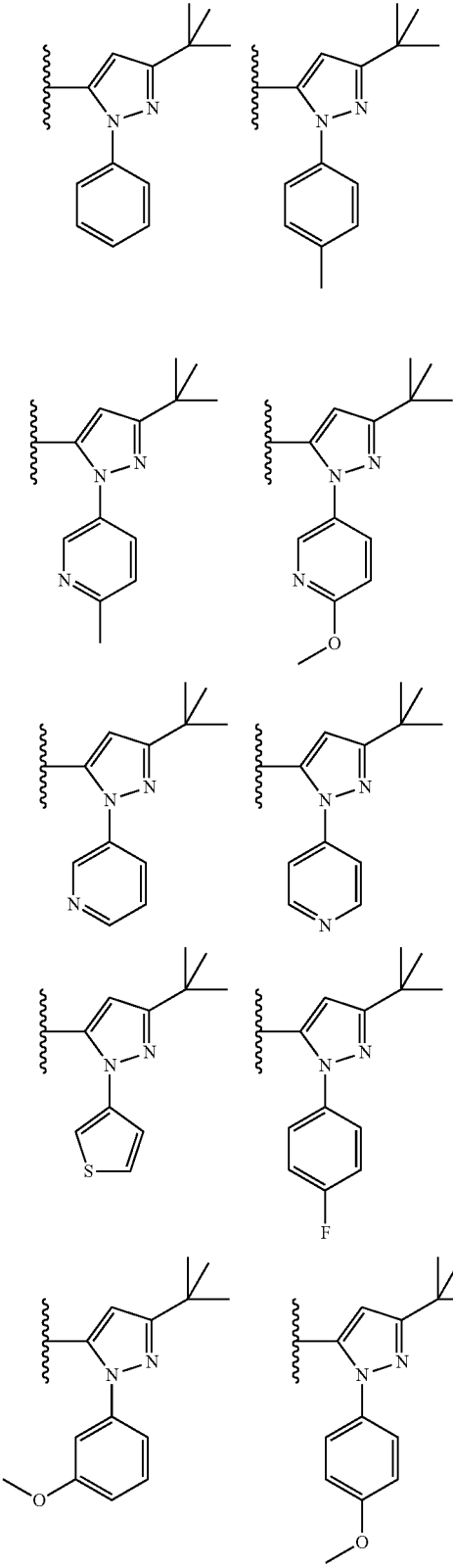

-continued

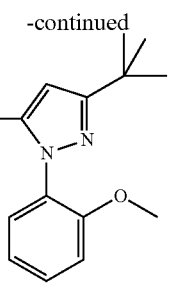

In one embodiment, -J is independently selected from:

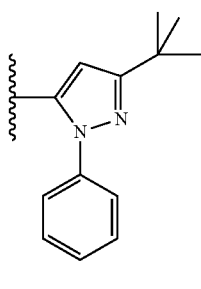 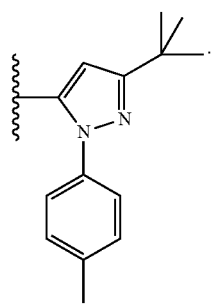

In one embodiment, -J is independently selected from:

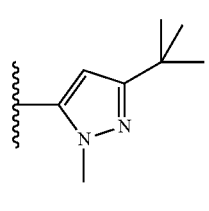 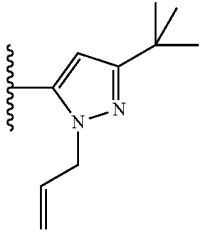

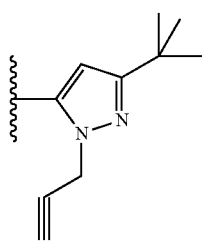 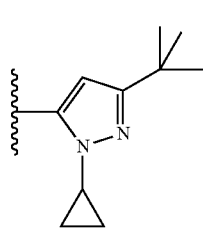

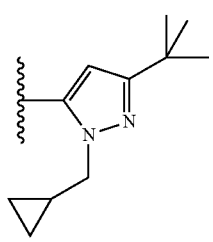 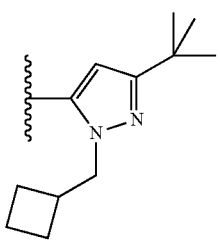

-continued

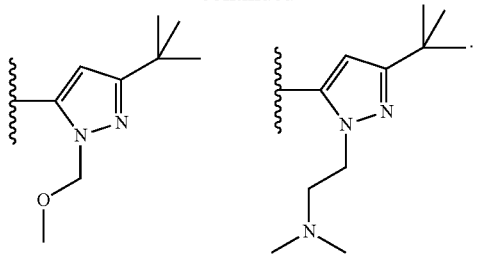

Some Preferred Examples of the Group -J: Phenyl

In one embodiment, -J is independently the following group, wherein m is independently 0, 1, 2, or 3; and each —$R^{PH2}$ is independently a substituent as defined herein for —$R^J$:

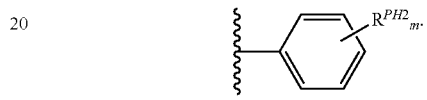

In one embodiment, m is independently 0, 1, or 2.
In one embodiment, m is independently 1 or 2.
In one embodiment, m is independently 0.
In one embodiment, m is independently 1.
In one embodiment, m is independently 2.
In one embodiment, each —$R^{PH2}$ is independently:
—F, —Cl, —Br, —I, —$R^9$, —OH, —$OR^9$, —$NH_2$, —$NHR^9$, —$NR^9{}_2$, —$NR^{9NA}R^{9NB}$, —$CF_3$, —$OCF_3$, or —$SCF_3$;
wherein:
each —$R^9$ is independently:
saturated aliphatic $C_{1-6}$alkyl, and is unsubstituted or substituted, for example, with one or more groups selected from —OH, —$OR^{99}$, —$NH_2$, —$NHR^{99}$, —$NR^{99}{}_2$, and —$NR^{9NA}R^{9NB}$;
saturated $C_{3-6}$cycloalkyl, and is unsubstituted or substituted, for example, with one or more groups selected from —OH, —$OR^{99}$, —$NH_2$, —$NHR^{99}$, and —$NR^{99}{}_2$;
azetidinyl, pyrrolidinyl, or piperidinyl, and is unsubstituted or substituted, for example, with one or more groups selected from —$R^{99}$; or
phenyl or $C_{5-6}$heteroaryl, and is unsubstituted or substituted, for example, with one or more groups selected from —F, —Cl, —Br, —I, —$R^{99}$, —$CF_3$, —OH, —$OR^{99}$, —$OCF_3$, —$NH_2$, —$NHR^{99}$, —$NR^{99}{}_2$, and —$NR^{9NA}R^{9NB}$;
and wherein:
—$NR^{9NA}R^{9NB}$ is independently azetidino, pyrrolidino, piperidino, piperizino, morpholino, azepino, or diazepino, and is optionally substituted with one or more groups selected from —$R^{99}$, —$CF_3$, —F, —OH, —$OR^{99}$, —$NH_2$, —$NHR^{99}$, and —$NR^{99}{}_2$;
wherein:
each —$R^{99}$ is independently saturated aliphatic $C_{1-4}$alkyl.
In one embodiment, each —$R^9$, if present, is independently:
saturated aliphatic $C_{1-6}$alkyl, and is unsubstituted or substituted, for example, with one or more groups selected from —OH, —$OR^{99}$, —$NH_2$, —$NHR^{99}$, —$NR^{99}{}_2$, and —$NR^{9NA}R^{9NB}$;
saturated $C_{3-6}$cycloalkyl, and is unsubstituted or substituted, for example, with one or more groups selected from —OH, —$OR^{99}$, —$NH_2$, —$NHR^{99}$, and —$NR^{99}{}_2$; or azetidinyl, pyrrolidinyl, or piperidinyl, and is unsubstituted or substituted, for example, with one or more groups selected from —$R^{99}$.

In one embodiment, each —$R^9$, if present, is independently:

saturated aliphatic $C_{1-6}$alkyl, and is unsubstituted or substituted, for example, with one or more groups selected from —OH, —$OR^{99}$, —$NH_2$, —$NHR^{99}$, —$NR^{99}_2$, and —$NR^{9NA}R^{9NB}$; or azetidinyl, pyrrolidinyl, or piperidinyl, and is unsubstituted or substituted, for example, with one or more groups selected from —$R^{99}$.

In one embodiment, each —$R^9$, if present, is independently:

saturated aliphatic $C_{1-6}$alkyl, and is unsubstituted or substituted, for example, with one or more groups selected from —OH, —$OR^{99}$, —$NH_2$, —$NHR^{99}$, —$NR^{99}_2$, and —$NR^{9NA}R^{9NB}$.

In one embodiment, each —$R^9$, if present, is independently saturated aliphatic $C_{1-6}$alkyl.

In one embodiment, —$NR^{9NB}R^{9NB}$, if present, is independently pyrrolidine, piperidine, piperizino, or morpholino, and is optionally substituted with one or more groups selected from —$R^{99}$.

In one embodiment, each —$R^{PH2}$ is independently —F, —Cl, —Br, —I, —$R^9$, —OH, —$OR^9$, —$CF_3$, —$OCF_3$, or —$SCF_3$.

In one embodiment, each —$R^{PH2}$ is independently —F, —Cl, -tBu, —$CF_3$, —$OCF_3$, or —$SCF_3$.

Combinations

Each and every compatible combination of the embodiments described above is explicitly disclosed herein, as if each and every combination was individually and explicitly recited.

Examples of Specific Embodiments

In one embodiment, the compounds are selected from compounds of the following formulae and pharmaceutically acceptable salts, hydrates, and solvates thereof:

| Compound | Synthesis | Structure |
|---|---|---|
| AA-001 | 14 | 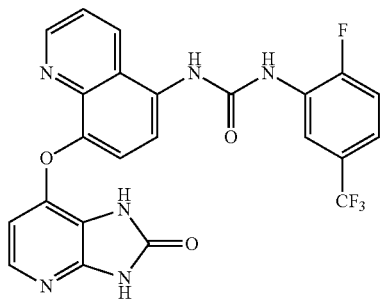 [SMILES: O=C(Nc1cc(C(F)(F)F)ccc1F)Nc1ccc(Oc2ccnc3[nH]c(=O)[nH]c23)c2ncccc12] |
| AA-002 | 15 | 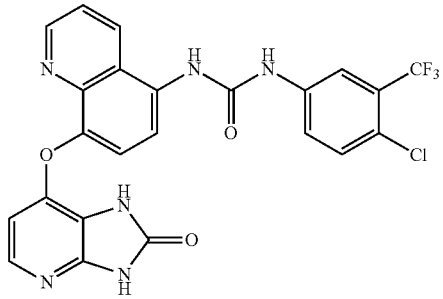 [SMILES: O=C(Nc1ccc(Cl)c(C(F)(F)F)c1)Nc1ccc(Oc2ccnc3[nH]c(=O)[nH]c23)c2ncccc12] |
| AA-003 | 16 | 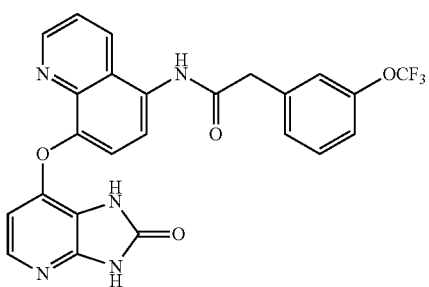 [SMILES: O=C(Cc1cccc(OC(F)(F)F)c1)Nc1ccc(Oc2ccnc3[nH]c(=O)[nH]c23)c2ncccc12] |
| AA-004 | 17 | 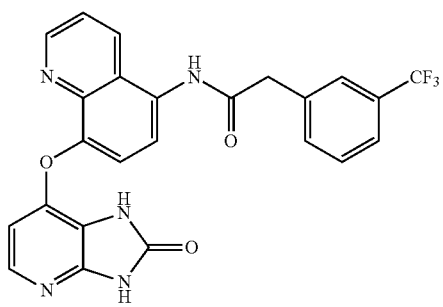 [SMILES: O=C(Cc1cccc(C(F)(F)F)c1)Nc1ccc(Oc2ccnc3[nH]c(=O)[nH]c23)c2ncccc12] |
| AA-005 | 18 | 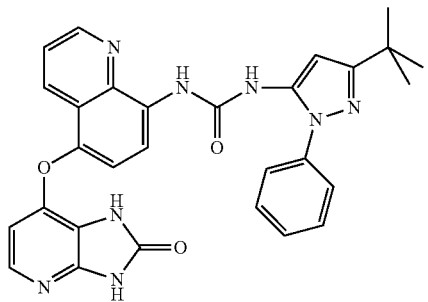 [SMILES: CC(C)(C)c1cc(NC(=O)Nc2ccc(Oc3ccnc4[nH]c(=O)[nH]c34)c3cccnc23)n(-c2ccccc2)n1] |
| AA-006 | 19 | 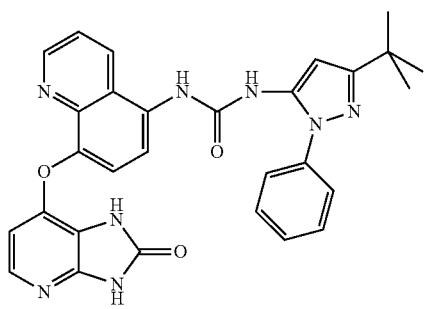 [SMILES: CC(C)(C)c1cc(NC(=O)Nc2ccc(Oc3ccnc4[nH]c(=O)[nH]c34)c3ncccc23)n(-c2ccccc2)n1] |

| Compound | Synthesis | Structure |
|---|---|---|
| AA-007 | 20 | 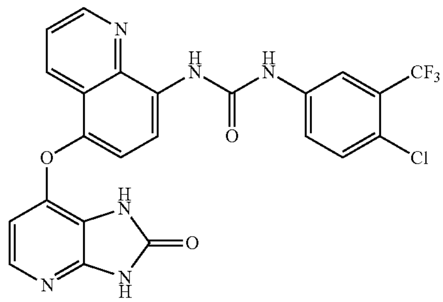 [SMILES: O=C(Nc1ccc(Cl)c(C(F)(F)F)c1)Nc1ccc(Oc2ccnc3[nH]c(=O)[nH]c23)c2cccnc12] |
| AA-008 | 21 | 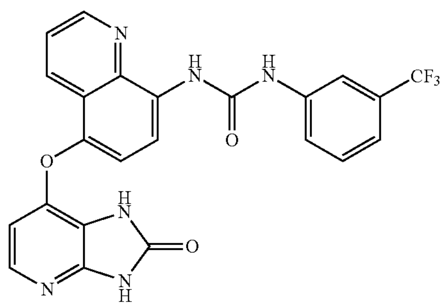 [SMILES: O=C(Nc1cccc(C(F)(F)F)c1)Nc1ccc(Oc2ccnc3[nH]c(=O)[nH]c23)c2cccnc12] |
| AA-009 | 22 | 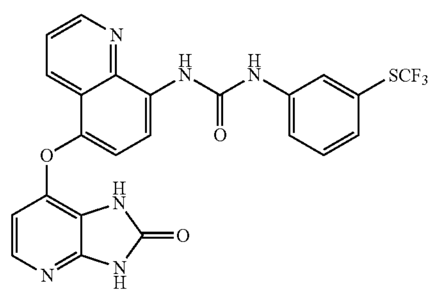 |
| AA-010 | 23 | 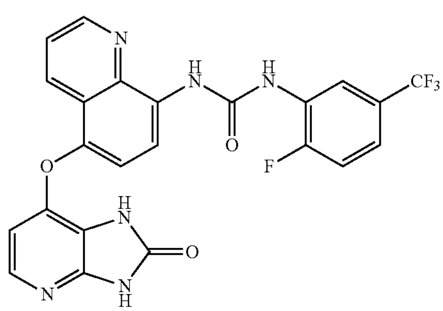 [SMILES: O=C(Nc1cc(C(F)(F)F)ccc1F)Nc1ccc(Oc2ccnc3[nH]c(=O)[nH]c23)c2cccnc12] |
| AA-011 | 24 | 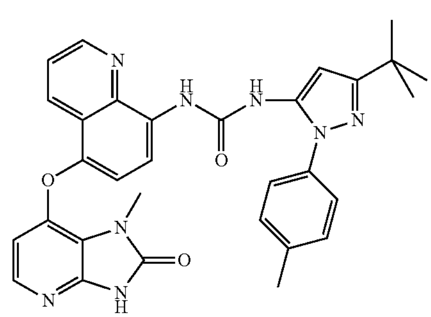 [SMILES: Cc1ccc(-n2nc(C(C)(C)C)cc2NC(=O)Nc2ccc(Oc3ccnc4[nH]c(=O)n(C)c34)c3cccnc23)cc1] |
| AA-012 | 25 | |
| AA-013 | 26 | |
| AA-014 | 27 | |
| AA-015 | 29 | |

| Compound | Synthesis | Structure |
|---|---|---|
| AA-016 | 36 | 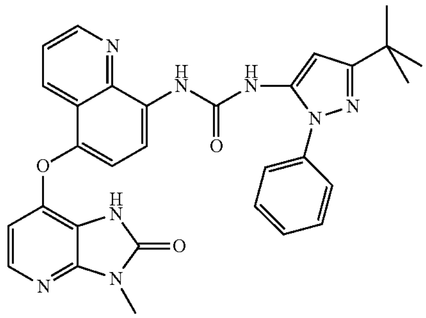 [SMILES: Cn1c(=O)[nH]c2c(Oc3ccc(NC(=O)Nc4cc(C(C)(C)C)nn4-c4ccccc4)c4ncccc34)ccnc21] |
| AA-017 | 40 | 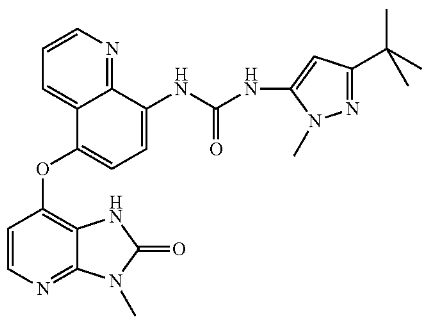 [SMILES: Cn1nc(C(C)(C)C)cc1NC(=O)Nc1ccc(Oc2ccnc3c2[nH]c(=O)n3C)c2cccnc12] |
| AA-018 | 37 | 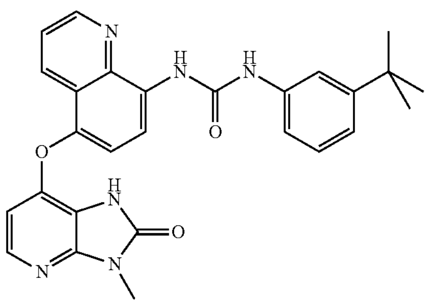 [SMILES: Cn1c(=O)[nH]c2c(Oc3ccc(NC(=O)Nc4cccc(C(C)(C)C)c4)c4ncccc34)ccnc21] |

In one embodiment, the compounds are selected from compounds of the following formulae and pharmaceutically acceptable salts, hydrates, and solvates thereof:

| Compound | Synthesis | Structure |
|---|---|---|
| BB-001 | 28 | |
| BB-002 | 32 | 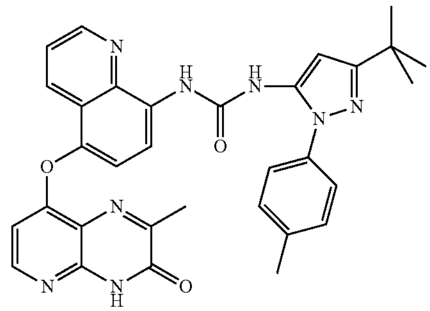 [SMILES: Cc1ccc(-n2nc(C(C)(C)C)cc2NC(=O)Nc2ccc(Oc3ccnc4[nH]c(=O)c(C)nc34)c3cccnc23)cc1] |
| BB-003 | 33 | 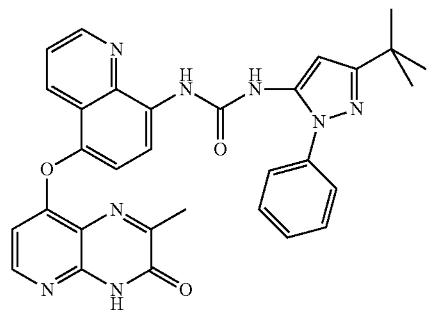 [SMILES: Cc1nc2c(Oc3ccc(NC(=O)Nc4cc(C(C)(C)C)nn4-c4ccccc4)c4ncccc34)ccnc2[nH]c1=O] |
| BB-004 | 30 | 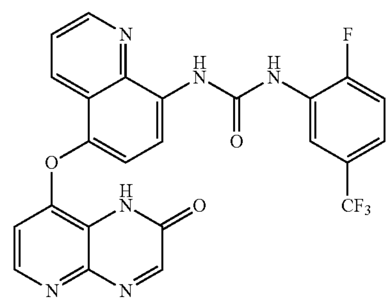 [SMILES: O=C(Nc1cc(C(F)(F)F)ccc1F)Nc1ccc(Oc2ccnc3ncc(=O)[nH]c23)c2cccnc12] |
| BB-005 | 31 | 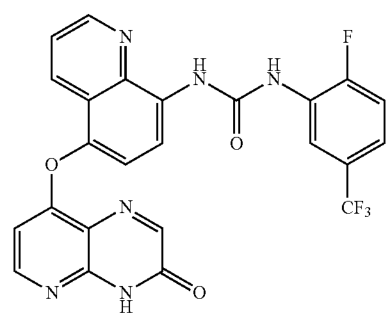 [SMILES: O=C(Nc1cc(C(F)(F)F)ccc1F)Nc1ccc(Oc2ccnc3[nH]c(=O)cnc23)c2cccnc12] |
| BB-006 | 39 | 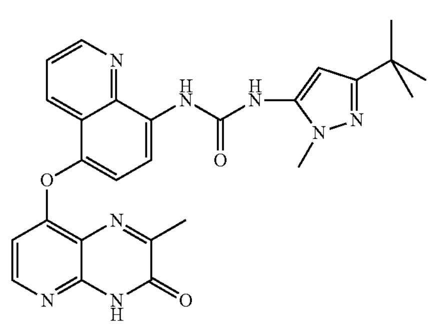 [SMILES: Cc1nc2c(Oc3ccc(NC(=O)Nc4cc(C(C)(C)C)nn4C)c4ncccc34)ccnc2[nH]c1=O] |

-continued

| Compound | Synthesis | Structure |
|---|---|---|
| BB-007 | 34 | 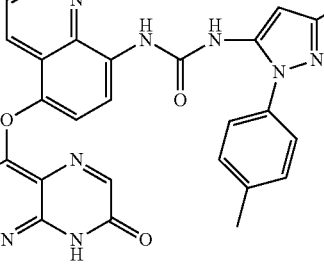 |
| BB-008 | 35 | 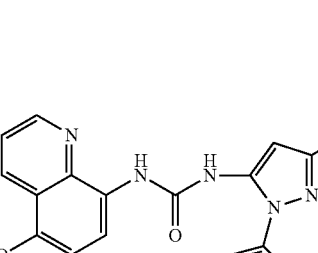 |
| BB-009 | 41 | 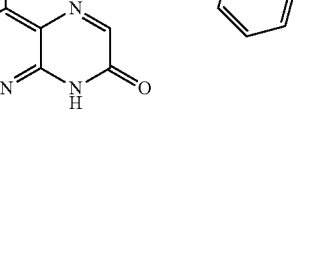 |
| BB-010 | 38 | 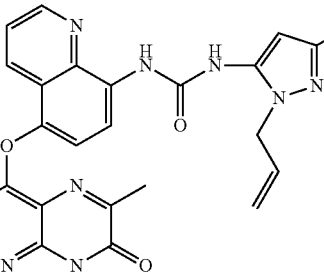 |

-continued

| Compound | Synthesis | Structure |
|---|---|---|
| BB-011 | 42 | 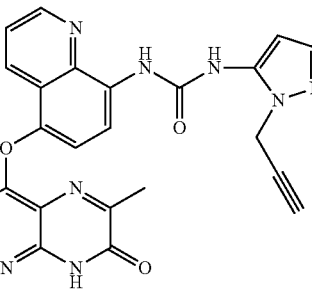 |
| BB-012 | 43 | 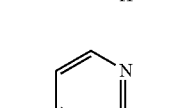 |
| BB-013 | 44 | 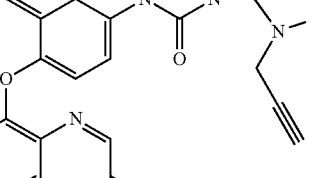 |

Substantially Purified Forms

One aspect of the present invention pertains to AQ compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to a equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and half chair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

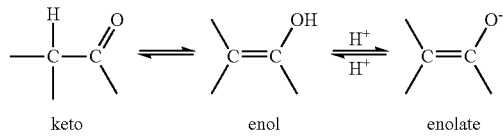

keto          enol          enolate

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts; 3rd Edition; John Wiley and Sons, 1999).

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)$CH_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—$CH_3$); a benzyloxy amide (—NHCO—$OCH_2C_6H_5$, —NH-Cbz); as a t-butoxy amide (—NHCO—OC$(CH_3)_3$, —NH-Boc); a 2-biphenyl-2-propoxy amide (—NHCO—OC$(CH_3)_2C_6H_4C_6H_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O.).

For example, a carboxylic acid group may be protected as an ester for example, as: an $C_{1-7}$alkyl ester (e.g., a methyl ester; a t-butyl ester); a $C_{1-7}$haloalkyl ester (e.g., a $C_{1-7}$trihaloalkyl ester); a tri$C_{1-7}$alkylsilyl-$C_{1-7}$alkyl ester; or a $C_{5-20}$aryl-$C_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—$CH_2$NHC(=O)$CH_3$).

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Several methods for the chemical synthesis of AQ compounds of the present invention are described herein. These and/or other well known methods may be modified and/or adapted in known ways in order to facilitate the synthesis of additional compounds within the scope of the present invention.

Compositions

One aspect of the present invention pertains to a composition (e.g., a pharmaceutical composition) comprising an AQ compound, as described herein, and a pharmaceutically acceptable carrier, diluent, or excipient.

Another aspect of the present invention pertains to a method of preparing a composition (e.g., a pharmaceutical composition) comprising admixing an AQ compound, as described herein, and a pharmaceutically acceptable carrier, diluent, or excipient.

Uses

The compounds described herein are useful, for example, in the treatment of diseases and disorders that are ameliorated by the inhibition of RAF (e.g., B-RAF), such as, for example, proliferative disorders, cancer, etc.

Use in Methods of Inhibiting RAF (e.g., B-RAF)

One aspect of the present invention pertains to a method of inhibiting RAF (e.g., B-RAF) function, in vitro or in vivo, comprising contacting a RAF (e.g., B-RAF) with an effective amount of an AQ compound, as described herein.

One aspect of the present invention pertains to a method of inhibiting RAF (e.g., B-RAF) function in a cell, in vitro or in vivo, comprising contacting the cell with an effective amount of an AQ compound, as described herein.

In one embodiment, the method is performed in vitro.
In one embodiment, the method is performed in vivo.

One of ordinary skill in the art is readily able to determine whether or not, and/or the degree to which, a candidate compound inhibits RAF (e.g., B-RAF) function. Suitable assays for determining RAF (e.g., B-RAF) function inhibition are described herein and/or are known in the art.

B-RAF Assays:

B-raf kinase activity is measured using a 4-tiered cascade enzyme assay similar to that described by Marais R., et al., 1997, J. Biol. Chem., Vol. 272, pp. 4378-4383. B-Raf containing the V600E mutation (Davies, H., et al., 2002, Nature, Vol. 417, pp. 949-954) and an N-terminal MDRGSH6 tag is expressed in SF9 insect cells. Detergent soluble extracts from these cells are diluted 1:100 into an assay mixture containing GST-MEK-H6 (6.5 μg/ml) and GST-ERK-H6 (100 μg/ml) in a buffer containing 800 μM ATP and appropriate concentrations of inhibitor or diluent as control. The mixture is incubated for up to 10 minutes at 30° C. to activate the ERK in a B-Raf dependent manner within the cascade. The reaction is then stopped by addition of 20 mM EDTA. The extent of activation of the GST-ERK is then determined by adding a portion of this quenched reaction mixture to a further reaction mixture containing MBP and 100 µM ATP/gamma [$^{32}$P]ATP. After 12 minutes' incubation at 30° C., the incorporation of [$^{32}$P] into the MBP substrate, as a measure of B-raf activity, is determined by precipitation with phosphoric acid and isolation by filtration on p81 phosphocellulose paper. The % inhibition of the B-raf kinase activity is calculated and plotted in order to determine the concentration of test compound required to inhibit 50% of the B-raf kinase activity ($IC_{50}$).

Alternatively, B-raf kinase activity is measured using a different 4-tiered cascade enzyme assay. B-Raf containing the V600E mutation (Davies, H., et al., 2002, *Nature*, Vol. 417, pp. 949-954) and an N-terminal MDRGSH6 tag is expressed in SF9 insect cells. Detergent soluble extracts from these cells are diluted 1:250 into an assay mixture containing GST-MEK-H6 (25 µg/ml), GST-ERK-H6 (281.25 µg/ml) and MBP in a buffer containing appropriate concentrations of inhibitor or diluent as control. 0.03 µL (100 µM) ATP is added and the mixture is incubated for up to 10 minutes at 30° C. to activate the ERK in a B-Raf dependent manner within the cascade. The extent of activation of the GST-ERK is then determined by adding 0.033 µL (100 µM) HOT $^{32}$Pα. After 10 minutes' incubation at 30° C., the reaction is stopped by isolation of a portion of the reaction mixture on p81 phosphocellulose paper and submersion of this paper in 0.4% orthophosphoric acid. Incorporation of [$^{32}$P] into the MBP substrate, as a measure of B-raf activity, is determined using a Packard Cernekov counter.

The % inhibition of the B-raf kinase activity is calculated and plotted in order to determine the concentration of test compound required to inhibit 50% of the B-raf kinase activity ($IC_{50}$).

C-RAF Assay:

C-raf (human) is diluted to a 10× working stock in 50 mM Tris pH 7.5, 0.1 mM EGTA, 0.1 mM sodium vanadate, 0.1% β-mercaptoethanol, 1 mg/ml BSA. One unit equals the incorporation of 1 nmol of phosphate per minute into myelin basic protein per minute. In a final reaction volume of 25 µl, c-raf (5-10 mU) is incubated with 25 mM Tris pH 7.5, 0.02 mM EGTA, 0.66 mg/ml myelin basic protein, 10 mM MgAcetate, [γ-$^{33}$P-ATP] (specific activity approx 500 cpm/µmol, concentration as required) and appropriate concentrations of inhibitor or diluent as control. The reaction is initiated by the addition of $Mg^{2+}$+[γ-$^{33}$P-ATP]. After incubation for 40 minutes at room temperature, the reaction is stopped by the addition of 5 µl of a 3% phosphoric acid solution. 10 µl of the reaction is spotted onto a P30 filtermat and washed 3 times for 5 minutes in 75 mM phosphoric acid and once in methanol prior to drying and counting to determine the C-raf activity. The % inhibition of the C-raf kinase activity is calculated and plotted in order to determine the concentration of test compound required to inhibit 50% of the C-raf kinase activity ($IC_{50}$).

Selectivity:

In one embodiment, the AQ compound selectively inhibits one RAF (e.g., B-RAF), over at least one other RAF (e.g., A-RAF and/or C-RAF).

For example, in one embodiment, the ratio of the $IC_{50}$ value for B-RAF to the $IC_{50}$ value for the other RAF (e.g., A-RAF and/or C-RAF) is at least 10, more preferably at least 100, most preferably at least 1000.

Use in Methods of Inhibiting Cell Proliferation, Etc.

The AQ compounds described herein, e.g., (a) regulate (e.g., inhibit) cell proliferation; (b) inhibit cell cycle progression; (c) promote apoptosis; or (d) a combination of one or more of these.

One aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of an AQ compound, as described herein.

In one embodiment, the method is a method of regulating (e.g., inhibiting) cell proliferation (e.g., proliferation of a cell), in vitro or in vivo, comprising contacting a cell with an effective amount of an AQ compound, as described herein.

In one embodiment, the method is performed in vitro.

In one embodiment, the method is performed in vivo.

In one embodiment, the AQ compound is provided in the form of a pharmaceutically acceptable composition.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays which may conveniently be used to assess the activity offered by a particular compound are described herein.

For example, a sample of cells (e.g., from a tumour) may be grown in vitro and a compound brought into contact with said cells, and the effect of the compound on those cells observed.

As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to an AQ compound, as described herein, for use in a method of treatment of the human or animal body by therapy.

Use in the Manufacture of Medicaments

Another aspect of the present invention pertains to use of an AQ compound, as described herein, in the manufacture of a medicament for use in treatment.

In one embodiment, the medicament comprises the AQ compound.

Methods of Treatment

Another aspect of the present invention pertains to a method of treatment comprising administering to a patient in need of treatment a therapeutically effective amount of an AQ compound, as described herein, preferably in the form of a pharmaceutical composition.

Conditions Treated—Conditions Ameliorated by the Inhibition of RAF

In one embodiment (e.g., of use in methods of therapy, of use in the manufacture of medicaments, of methods of treatment), the treatment is treatment of a disease or disorder that is characterised by the up-regulation and/or activation of RAF (e.g., B-RAF), and/or is ameliorated by the inhibition of RAF (e.g., B-RAF).

In one embodiment, the treatment is treatment of cancer that is characterised by the up-regulation and/or activation of RAF (e.g., B-RAF), and/or is ameliorated by the inhibition of RAF (e.g., B-RAF).

Conditions Treated—Conditions Ameliorated by the Inhibition of RTKs

In one embodiment (e.g., of use in methods of therapy, of use in the manufacture of medicaments, of methods of treatment), the treatment is treatment of a disease or disorder that is characterised by the up-regulation and/or activation of a receptor tyrosine kinase (RTK), and/or is ameliorated by the inhibition of a receptor tyrosine kinase (RTK). Examples of RTKs include FGFR, Tie, VEGFR and/or Eph, for example, FGFR-1, FGFR-2, FGFR-3, Tie2, VEGFR-2 and/or EphB2.

In one embodiment, the treatment is treatment of cancer that is characterised by the up-regulation and/or activation of a receptor tyrosine kinase (RTK), and/or is ameliorated by the inhibition of a receptor tyrosine kinase (RTK).

Conditions Treated—Conditions characterised by Angiogenesis

In one embodiment (e.g., of use in methods of therapy, of use in the manufacture of medicaments, of methods of treatment), the treatment is treatment of a disease or disorder that is characterised by inappropriate, excessive, and/or undesirable angiogenesis (as "anti-angiogenesis agents"). Examples of such disorders are discussed herein.

Conditions Treated—Proliferative Disorders and Cancer

The AQ compounds are useful in the treatment of proliferative disorders (as "anti-proliferative agents"), cancer (as "anti-cancer agents"), etc.

In one embodiment (e.g., of use in methods of therapy, of use in the manufacture of medicaments, of methods of treatment), the treatment is treatment of a proliferative disorder.

The term "proliferative disorder," as used herein, pertains to an unwanted or uncontrolled cellular proliferation of excessive or abnormal cells which is undesired, such as, neoplastic or hyperplastic growth.

In one embodiment, the treatment is treatment of: a proliferative disorder characterised by benign, pre-malignant, or malignant cellular proliferation, including but not limited to, neoplasms, hyperplasias, and tumours (e.g., histocytoma, glioma, astrocytoma, osteoma), cancers (see below), psoriasis, bone diseases, fibroproliferative disorders (e.g., of connective tissues), pulmonary fibrosis, atherosclerosis, smooth muscle cell proliferation in the blood vessels, such as stenosis or restenosis following angioplasty.

In one embodiment, the treatment is treatment of: cancer.

In one embodiment, the treatment is treatment of: lung cancer, small cell lung cancer, non-small cell lung cancer, gastrointestinal cancer, stomach cancer, bowel cancer, colon cancer, rectal cancer, colorectal cancer, thyroid cancer, breast cancer, ovarian cancer, endometrial cancer, prostate cancer, testicular cancer, liver cancer, kidney cancer, renal cell carcinoma, bladder cancer, pancreatic cancer, brain cancer, glioma, sarcoma, osteosarcoma, bone cancer, skin cancer, squamous cancer, Kaposi's sarcoma, melanoma, malignant melanoma, lymphoma, or leukemia.

In one embodiment, the treatment is treatment of:
a carcinoma, for example a carcinoma of the bladder, breast, colon (e.g., colorectal carcinomas such as colon adenocarcinoma and colon adenoma), kidney, epidermal, liver, lung (e.g., adenocarcinoma, small cell lung cancer and non-small cell lung carcinomas), oesophagus, gall bladder, ovary, pancreas (e.g., exocrine pancreatic carcinoma), stomach, cervix, thyroid, prostate, skin (e.g., squamous cell carcinoma);
a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma;
a hematopoietic tumor of myeloid lineage, for example acute and chronic myelogenous leukemias, myelodysplastic syndrome, or promyelocytic leukemia;
a tumour of mesenchymal origin, for example fibrosarcoma or habdomyosarcoma;
a tumor of the central or peripheral nervous system, for example astrocytoma, neuroblastoma, glioma or schwannoma;
melanoma; seminoma; teratocarcinoma; osteosarcoma; xenoderoma pigmentoum; keratoctanthoma; thyroid follicular cancer; or Kaposi's sarcoma.

In one embodiment, the treatment is treatment of solid tumour cancer.

In one embodiment, the treatment is treatment of melanoma or malignant melanoma.

In one embodiment, the treatment is treatment of colorectal cancer.

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death). The AQ compounds of the present invention may be used in the treatment of the cancers described herein, independent of the mechanisms discussed herein.

Conditions Treated—Proliferative Disorders and Cancer Associated with RAF

Cancers with, for example, activating mutations of ras, raf and EGFR or over expression of ras, raf and EGFR including any of the isoforms thereof, may be particularly sensitive to inhibitors of RAF (e.g., B-RAF) activity. Patients with activating mutants of RAF (e.g., B-RAF) may also find treatment with inhibitors of RAF (e.g., B-RAF) activity particularly beneficial. Cancers with other abnormalities leading to an upregulated raf-MEK-ERK pathway signal may also be particularly sensitive to treatment with inhibitors of RAF (e.g., B-RAF) activity. Examples of such abnormalities include consitutive activation of a growth factor receptor; overexpression of one or more growth factor receptors; and overexpression of one or more growth factors.

In one embodiment (e.g., of use in methods of therapy, of use in the manufacture of medicaments, of methods of treatment), the treatment is treatment of a proliferative disorder as described above, for example, cancer, that is characterised by:
(a) activating mutants of ras or raf;
(b) upregulation of ras or raf;
(c) upregulated raf-MEK-ERK pathway signals;
(d) upregulation of growth factor receptors, such as ERBB2 and EGFR.

In one embodiment, the proliferative disorder is characterised by cells which overexpress RAF (e.g., B-RAF) or express or overexpress mutant raf (e.g., B-RAF). In one embodiment, the proliferative disorder is characterised by cells which overexpress raf (e.g., B-RAF). In one embodiment, the proliferative disorder is characterised by cells which express or overexpress mutant RAF (e.g., B-RAF). In one embodiment, the proliferative disorder is characterised by cells which overexpress RAF (e.g., B-RAF), or overexpress mutant RAF (e.g., B-RAF), as compared to corresponding normal cells. In one embodiment, the overexpression is by a factor of 1.5, 2, 3, 5, 10, or 20.

In one embodiment (e.g., of use in methods of therapy, of use in the manufacture of medicaments, of methods of treatment), the treatment is treatment of a disease or disorder associated with a mutated form of RAF (e.g., B-RAF), such as, for example, the mutations described in Wan, P., et al., 2004, *Cell*, Vol. 116, pp. 855-867 and Stratton et at, 2003, published international patent application publication number WO 03/056036.

Conditions Treated—Inflammation etc.

The AQ compounds are useful in the treatment of disorders associated with inflammation (as "anti-inflammation agents"), etc.

The function of inflammatory cells is controlled by many factors the effects of which are mediated by different signal transduction pathways. Although some key pro-inflammatory functions are mediated by p38 Map kinase (e.g., TNF release), others are mediated by other pathways. The raf-MEK-ERK pathway, in particular, is an important activating and proliferative signal in many inflammatory cells. B and T lymphocytes, in particular, require activation of the raf-MEK-ERK pathway for clonal expansion and generation of effector populations (see, e.g., Cantrell, D. A., 2003, *Immunol Rev.*, Vol. 192, pp. 122-130; Genot, E. and Cantrell, D. A., 2000, *Curr. Opin. Immunol.*, Vol. 12(3), pp. 289-294).

In one embodiment, the treatment is treatment of: inflammatory diseases, such as rheumatoid arthritis, osteoarthritis, rheumatoid spondylitis, gouty arthritis, traumatic arthritis, rubella arthritis, psoriatic arthritis, and other arthritic conditions; Alzheimer's disease; toxic shock syndrome, the inflammatory reaction induced by endotoxin or inflammatory bowel disease; tuberculosis; atherosclerosis; muscle degeneration; Reiter's syndrome; gout; acute synovitis; sepsis; septic shock; endotoxic shock; gram negative sepsis; adult respiratory distress syndrome; cerebral malaria; chronic pulmonary inflammatory disease; silicosis; pulmonary sarcoisosis; bone resorption diseases; reperfusion injury; graft versus host reaction; allograft rejections; fever and myalgias due to infection, such as influenza, cachexia, in particular cachexia secondary to infection or malignancy, cachexia secondary to acquired immune deficiency syndrome (AIDS); AIDS; ARC (AIDS related complex); keloid formation; scar tissue formation; Crohn's disease; ulcerative colitis; pyresis; chronic obstructive pulmonary disease (COPD); acute respiratory distress syndrome (ARDS); asthma; pulmonary fibrosis; bacterial pneumonia.

In one preferred embodiment, the treatment is treatment of: arthritic conditions, including rheumatoid arthritis and rheumatoid spondylitis; inflammatory bowel disease, including Crohn's disease and ulcerative colitis; and chronic obstructive pulmonary disease (COPD).

In one preferred embodiment, the treatment is treatment of: an inflammatory disorder characterized by T-cell proliferation (T-cell activation and growth), for example, tissue graft rejection, endotoxin shock, and glomerular nephritis.

Screening

Prior to treatment, a patient may be screened to determine whether a disease or disorder from which the patient is or may be suffering is one which would be susceptible to treatment with a compound that inhibits RAF (e.g., B-RAF) activity or has activity against an RTK (e.g., FGFR-1, FGFR-2, FGFR-3, VEGFR-2, Tie2, EphB2).

For example, a biological sample taken from a patient may be analysed to determine whether a disease or disorder, such as cancer, that the patient is or may be suffering from is one which is characterised by elevated expression or activation of RAF (e.g., B-RAF), or an RTK (e.g., FGFR-1, FGFR-2, FGFR-3, VEGFR-2, Tie2, EphB2), or is the result of an activating mutation. Thus, the patient may be subjected to a diagnostic test to detect a marker characteristic of over-expression or activation of RAF (e.g., B-RAF) or an RTK (e.g., FGFR-1, FGFR-2, FGFR-3, VEGFR-2, Tie2, EphB2), or a mutation thereof.

As used herein, the term "marker" includes genetic markers (including, e.g., the measurement of DNA composition to identify mutations of raf, ras, MEK, ERK or a growth factor such as ERBB2 or EGFR) and markers which are characteristic of upregulation of raf, ras, MEK, ERK, growth factors receptors such as ERBB2 or EGFR including enzyme activity, enzyme levels, enzyme state (e.g. phosphorylated or not) and mRNA levels of the aforementioned proteins. Methods for identification and analysis of mutations are well known. See, for example, *Anticancer Research*, 1999, Vol. 19(4A), pp. 2481-2483; *Clin. Chem.*, 2002, Vol. 48, p. 428; *Cancer Research*, 2003, Vol. 63(14), pp. 3955-3957.

The term "marker" further includes genetic markers including, for example, the measurement of DNA composition to identify mutations of RTKs, e.g., FGFR-1, FGFR-2, FGFR-3, VEGFR-2, Tie2, and EphB2. The term "marker" also includes markers that are characteristic of up-regulation of RTKs, including enzyme activity, enzyme levels, enzyme state (e.g., phosphorylated or not) and mRNA levels of the aforementioned proteins.

Upregulation includes elevated expression or over expression, including gene amplification (i.e., multiple gene copies), increased expression by a transcriptional effect, hyperactivity, and activation, including activation by mutations.

Other tumours that have an upregulated raf-MEK-ERK pathway signal may also be particularly sensitive to inhibitors of RAF (e.g., B-RAF) activity. A number of assays exist which can identify tumours that exhibit upregulation in the raf-MEK-ERK pathway, including the commercially available MEK½ (MAPK Kinase) assay from Chemicon International. Upregulation can result from over expression or activation of growth factor receptors such as ERBB2 and EGFR, or mutant ras or raf proteins.

Typical methods for screening for over expression, upregulation or mutants include, but are not limited to, standard methods such as reverse-transcriptase polymerase chain reaction (RT-PCR) or in-situ hybridisation.

In screening by RT-PCR, the level of mRNA for the aforementioned proteins in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described, for example, in Ausubel, F. M. et al., eds., *Current Protocols in Molecular Biology*, 2004 (John Wiley & Sons Inc.); Innis, M. A. et-al., eds., *PCR Protocols: A Guide to Methods and Applications*, 1990 (Academic Press). Reactions and manipulations involving nucleic acid techniques are also described in Sambrook at al., *Molecular Cloning: A Laboratory Manual*, 3rd edition, 2001 (Cold Spring Harbor Laboratory Press). Alternatively, a commercially available kit for RT-PCR (e.g., Roche Molecular Biochemicals) may be used, or methodology as set forth in U.S. Pat. Nos. 4,666,828; 4,683,202; 4,801,531; 5,192,659, 5,272,057, 5,882,864, and 6,218,529.

An example of an in-situ hybridisation technique would be fluorescence in situ hybridisation (FISH) (see, e.g., Angerer, 1987, *Meth. Enzymol.*, Vol. 152, p. 649). Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, in order to enable specific hybridization with the target nucleic acid(s) under stringent conditions. Standard methods for carrying out FISH are described, for example, in Ausubel, F. M. et al., eds., *Current Protocols in Molecular Biology*, 2004 (John Wiley & Sons Inc.); Bartlett, John M. S., "Fluorescence In Situ Hybridization: Technical Overview," in: *Molecular Diagnosis of Cancer, Methods and Protocols, 2nd ed.* (*Series: Methods in Molecular. Medicine*), March 2004, pp. 77-88 (ISBN: 1-59259-760-2).

Alternatively, the protein products expressed from the mRNAs may be assayed by immunohistochemistry of tumour sections, solid phase immunoassay with microtiter plates, Western blotting, 2-dimensional SDS-polyacrylamide gel electrophoresis, ELISA, and other methods known in the art for detection of specific proteins. Detection methods would include the use of site specific antibodies, such as, phospho raf, phospho ERK, phospho MEK, or phosphotyrosine. In addition to tumour biopsies, other samples which could be utilised include pleural fluid, peritoneal fluid, urine, stool biopsies, sputum, blood (isolation and enrichment of shed tumour cells).

In addition, mutant forms of raf, EGFR or ras can be identified by direct sequencing of, for example, tumour biopsies using PCR and methods to sequence PCR products directly, for example, using methods as described herein. These and other well-known techniques for detection of the over expression, activation, or mutations may be used.

Also, abnormal levels of proteins such as raf, ras and EGFR can be measured using standard enzyme assays, for example for raf those assays described herein.

Alternative methods for the measurement of the over expression or activation of FGFR, Tie, VEGFR or Eph kinases, in particular VEGFR including the isoforms thereof, include the measurement of microvessel density. This can be measured, for example, using methods described by Orre and Rogers, 1999, *Int. J. Cancer*, Vol. 84(2), pp. 101-108. Assay methods also include the use of markers; for example, in the case of VEGFR, markers include CD31, CD34 and CD105 (Mineo et al., 2004, *J. Clin. Pathol.*, Vol. 57(6), pp. 591-597).

Treatment

The term "treatment," as used herein in the context of treating a disease or disorder, pertains generally to treatment and therapy, whether of a human or an animal (e.g., in veterinary applications), in which some desired therapeutic effect is achieved, for example, the inhibition of the progress of the disease or disorder, and includes a reduction in the rate of progress, a halt in the rate of progress, alleviation of symptoms of the disease or disorder, amelioration of the disease or disorder, and cure of the disease or disorder. Treatment as a prophylactic measure (i.e., prophylaxis) is also included. For example, use with patients who have not yet developed the disease or disorder, but who are at risk of developing the disease or disorder, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents, for example, cytotoxic agents, anticancer agents, etc. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

For example, it may be beneficial to combine treatment with a compound as described herein with one or more other (e.g., 1, 2, 3, 4) agents or therapies that regulates cell growth or survival or differentiation via a different mechanism, thus treating several characteristic features of cancer development.

One aspect of the present invention pertains to a compound as described herein, in combination with one or more additional therapeutic agents, as described below.

Examples of additional therapeutic agents that may be administered together (whether concurrently or at different time intervals) with the compounds described herein include:

(a) topoisomerase I inhibitors;
(b) antimetabolites;
(c) tubulin targeting agents;
(d) DNA binder and topoisomerase II inhibitors;
(e) alkylating agents;
(f) monoclonal antibodies;
(g) anti-hormones;
(h) signal transduction inhibitors;
(i) proteasome inhibitors;
(j) DNA methyl transferases;
(k) cytokines and retinoids.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Other Uses

The AQ compounds described herein may also be used as cell culture additives to inhibit RAF (e.g., B-RAF) function, e.g., to inhibit cell proliferation, etc.

The AQ compounds described herein may also be used as part of an in vitro assay, for example, in order to determine whether a candidate host is likely to benefit from treatment with the compound in question.

The AQ compounds described herein may also be used as a standard, for example, in an assay, in order to identify other compounds, other RAF (e.g., B-RAF) function inhibitors, other anti-proliferative agents, other anti-cancer agents, etc.

Kits

One aspect of the invention pertains to a kit comprising (a) an AQ compound as described herein, or a composition comprising an AQ compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The AQ compound or pharmaceutical composition comprising the AQ compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

Furthermore, the subject/patient may be any of its forms of development, for example, a fetus.

In one preferred embodiment, the subject/patient is a human.

Formulations

While it is possible for the AQ compound to be administered alone, it is preferable to present it as a pharmaceutical formulation (e.g., composition, preparation, medicament) comprising at least one AQ compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, antioxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one AQ compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, lozenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, lozenges, pastilles, as well as patches, adhesive plasters, depots, and reservoirs. Lozenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, lozenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichorotetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the AQ compounds, and compositions comprising the AQ compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular AQ compound, the route of administration, the time of administration, the rate of excretion of the AQ compound, the duration of the treatment, other drugs, compounds, and/or materials used in combination, the severity of the disease or disorder, and the species, sex, age, weight, condition, general health, and prior medical history of the patient. The amount of AQ compound and route of administration will ultimately be at the discretion of the physician, veterinarian, or clinician, although generally the dosage will be selected to achieve local concentrations at the site of action which achieve the desired effect without causing substantial harmful or deleterious side-effects. Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the AQ compound is in the range of about 10 µg to about 250 mg (more typically about 100 µg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

Chemical Synthesis

Several methods for the chemical synthesis of compounds of the present invention are described herein. These and/or other well known methods may be modified and/or adapted in known ways in order to facilitate the synthesis of additional compounds within the scope of the present invention.

Descriptions of general laboratory methods and procedures, useful for the preparation of the compounds described herein, are provided in *Vogel's Textbook of Practical Organic Chemistry, 5th Edition,* 1989, (Editors: Furniss, B. S., Hannaford, A. J., Smith, P. W. G., Tatchell, A. R.) (published by Longmann, UK).

Methods for the synthesis of pyridine compounds in particular are described in *Heterocyclic Chemistry, 3rd Edition,* 1998, Joule, J. A, Mills, R. and Smith, G. F. (published by Chapman & Hall, UK).

The compounds described herein can be prepared via a key intermediate (2). This intermediate can be prepared from commercially available starting material, 2-amino-3-nitro-4-chloropyridine, (1), and optionally substituted amino-hydroxy-quinolines or amino-hydroxy-isoquinolines. Compounds (2) are then protected selectively at the amino group, for example as a BOC carbamate or trifluoroacetamide, to afford intermediates, (3). The intermediates, (3), can also be obtained directly from 2-amino-3-nitro-4-chloropyridine, (1), and N-BOC-protected amino-hydroxy-quinolines or amino-hydroxy-isoquinolines. The nitro group of the protected intermediate, (3), may be reduced to an amino group with Pd/C and ammonium formate or hydrogen, or with $NiCl_2$ and $NaBH_4$ to give the diamino intermediate (4). The same method can be applied using any of the amino-hydroxy-quinolines or -isoquinolines shown in Table 1 below. Intermediate (4) can be cyclised to give pyridoimidazolone (5) using phosgene or triphosgene. Deprotection of (5) affords the key common intermediate (6). An example of such a method is illustrated in the following scheme using 5-hydroxy-8-aminoquinoline.

Scheme 1

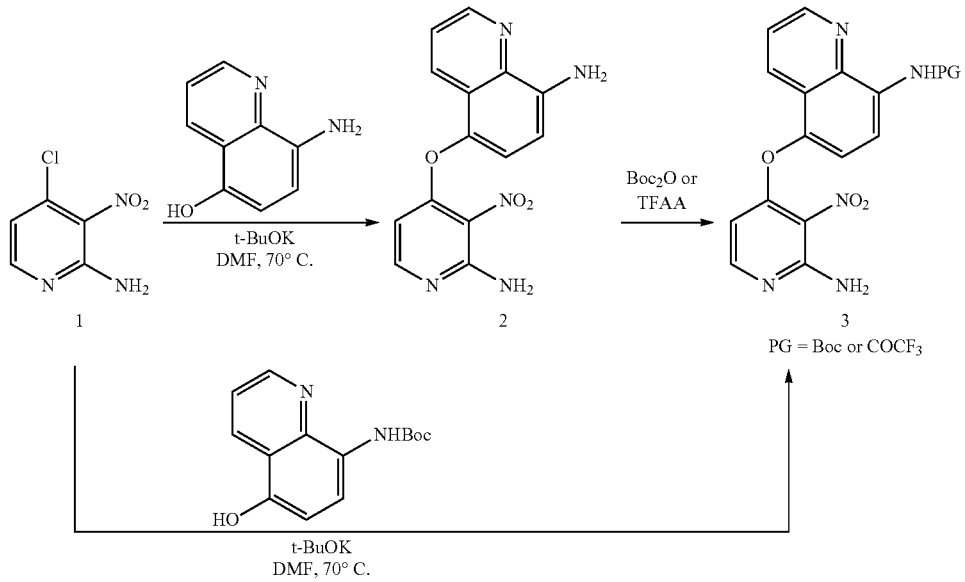

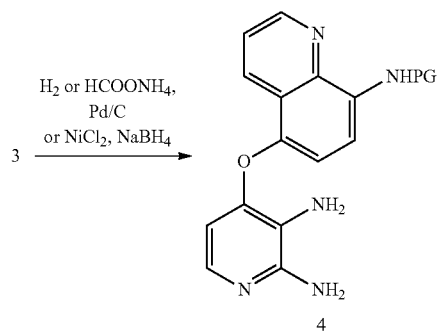
TABLE 1
| Starting Material | Structure | Intermediate (4) |
|---|---|---|
| 5-Amino-8-hydroxyquinoline | 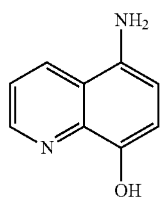 [SMILES: Nc1ccc(O)c2ncccc12] | |
| 5-Amino-8-hydroxy-isoquinoline | 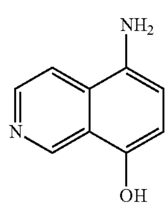 [SMILES: Nc1ccc(O)c2cnccc12] | |
| 8-Amino-5-hydroxy-isoquinoline | 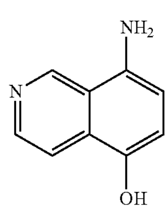 [SMILES: Nc1ccc(O)c2ccncc12] | |

TABLE 1-continued

| Starting Material | Structure | Intermediate (4) |
|---|---|---|
| 8-Amino-5-hydroxy-quinoline | 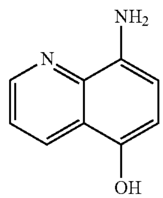 [SMILES: Nc1ccc(O)c2cccnc12] | |
| 1-Amino-4-hydroxy-isoquinoline | 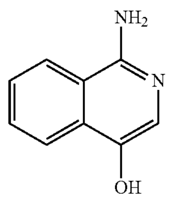 [SMILES: Nc1ncc(O)c2ccccc12] | |
| 2-amino-7-hydroxy-isoquinoline | 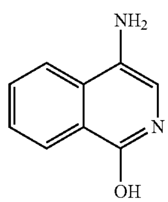 [SMILES: Nc1cnc(O)c2ccccc12] | |
| 6-Amino-8-hydroxy-quinoline | 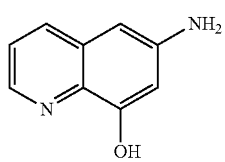 [SMILES: Nc1cc(O)c2ncccc2c1] | |
| 8-Amino-6-hydroxy-quinoline | 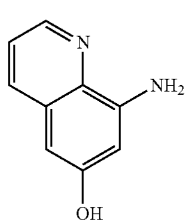 [SMILES: Nc1cc(O)cc2cccnc12] | |

TABLE 1-continued

| Starting Material | Structure | Intermediate (4) |
|---|---|---|
| 2-Amino-4-hydroxy-quinoline | 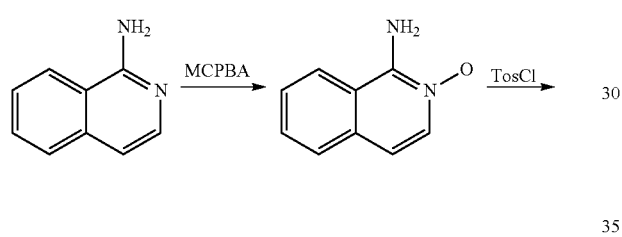 | |

All of the starting materials presented in Table 1 (above) are commercially available, except 1-amino-4-hydroxy-isoquinoline, which can be prepared, for example, as shown in the following scheme, and 1-hydroxy-4-amino-isoquinoline which can be prepared, for example, as shown in the subsequent scheme.

Scheme 2A

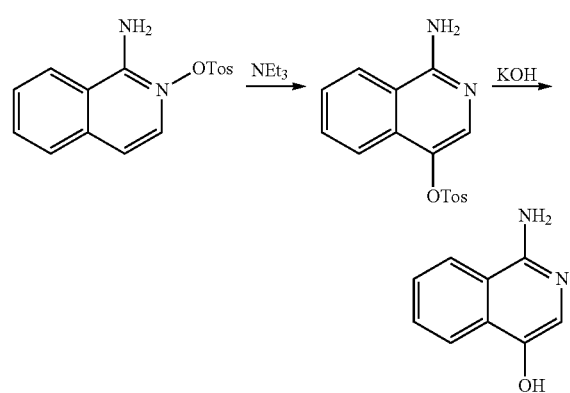

Scheme 2B

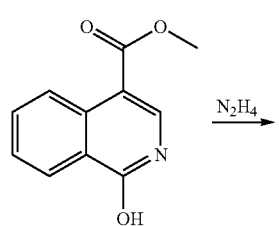

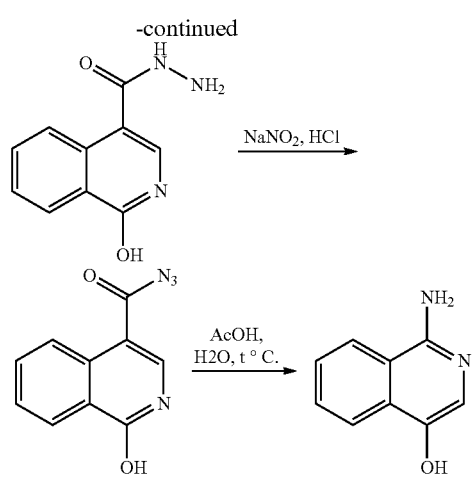

The following methods and schemes are illustrated using unsubstituted quinolinyl/isoquinolinyl groups, but it should be understood that these methods are also suitable for the preparation of compounds with substituted quinolinyl/isoquinolinyl groups.

Cyclisation of the diamino intermediate (4) to the bicyclic systems is exemplified for 8-amino-5-hydroxyquinoline in Scheme 3. Similar methods can be used with the other quinolines and isoquinolines described in Table 1 above. Intermediate (4) can be cyclised to pyridoimidazolone (5) using phosgene or triphosgene. Deprotection of (5) affords the key common intermediate (6). An example of such a method is illustrated in the following scheme using 5-hydroxy-8-aminoquinoline. Pyridopyrazinones can be obtained from intermediate (4) by reaction with ethyl glyoxylate, ethyl pyruvate or similar α-ketoesters. Both isomers (7) and (8) can be obtained from the reaction of (4) with ethyl glyoxylate. Deprotection of the protecting group (PG) with TFA or tetrabutyl ammonium fluoride (TBAF) (for Boc protecting group) or ammonia (for trifluoroacetamide) produces the common intermediates (9) or (10). Similarly, two isomers, (13) and (14), can be obtained from the reaction of (4) with ethyl pyruvate followed by deprotection. Amino-pyridopyrazinones (17) and (18) can be obtained from intermediate (4) by reaction with ethyl 2-ethoxy-2-iminoacetate and deprotection. The ratio of the two isomers can be influenced by the choice of solvents, so that one is obtained preferentially. Pyridopyrazines (20) can be obtained from intermediate (4) by reaction with glyoxal or 1,4-dioxane-2,3-diol followed by deprotection. Pyridopyrazin-diones (22) can be obtained from intermediate (4) by reaction with diethyloxalate or oxalyl chloride followed by deprotection.
Scheme 3
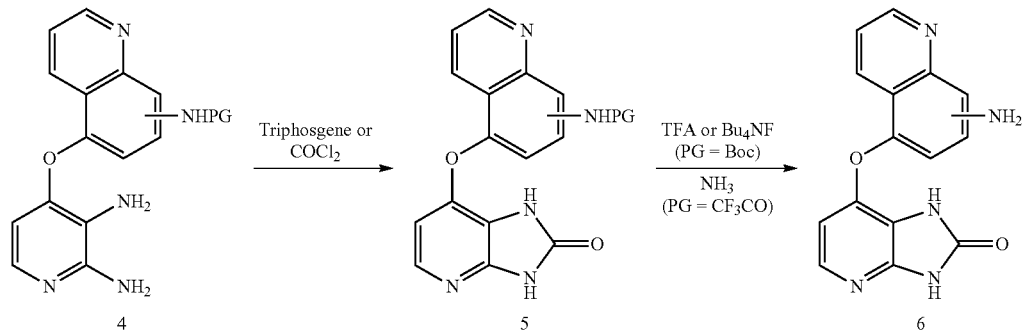
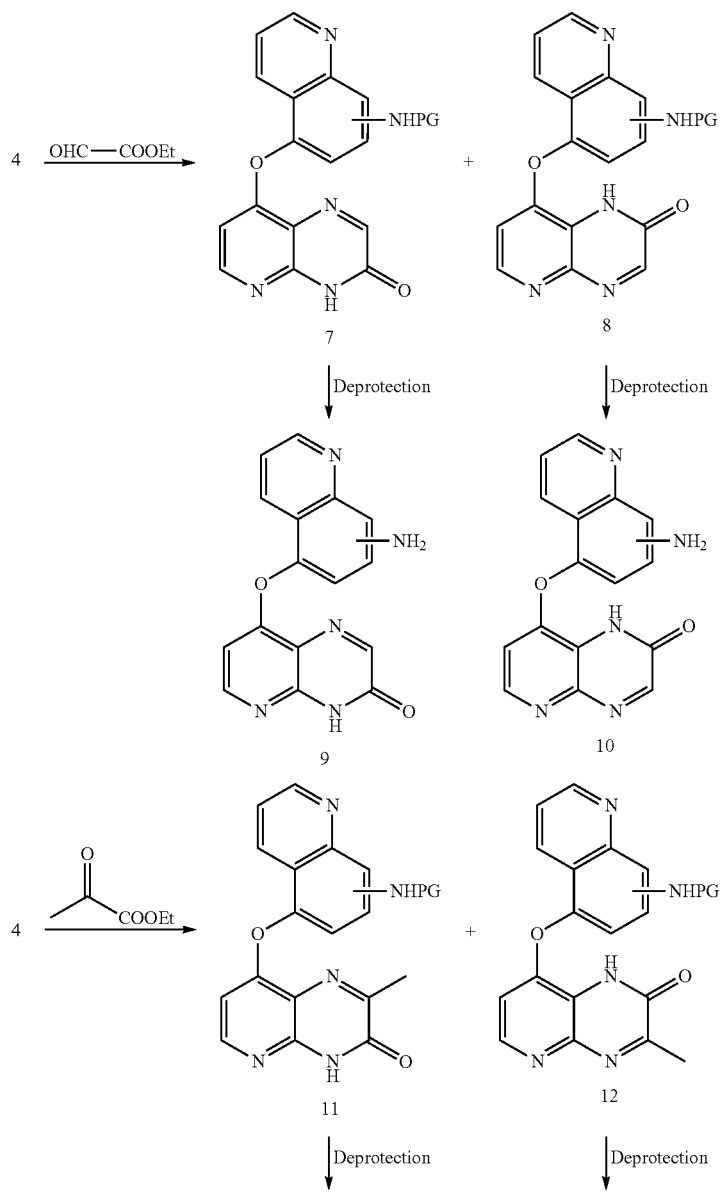

-continued
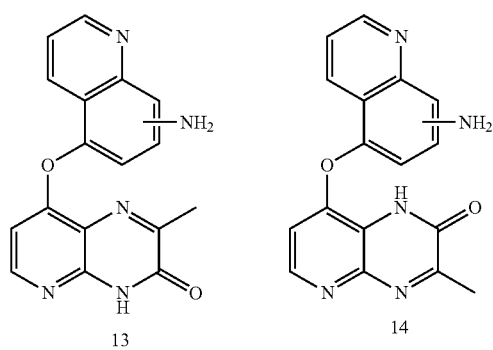
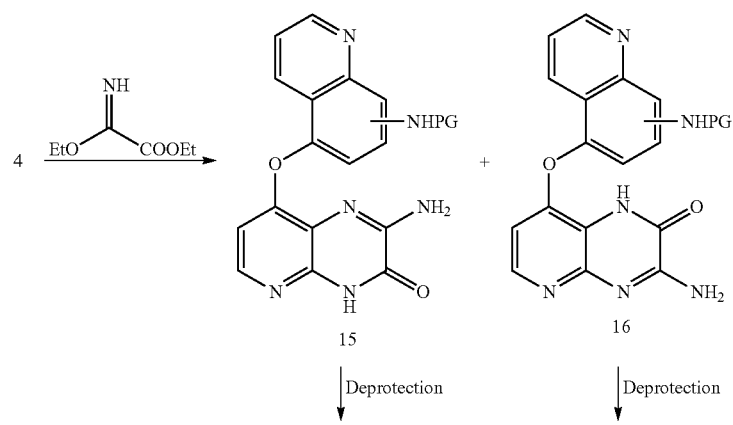
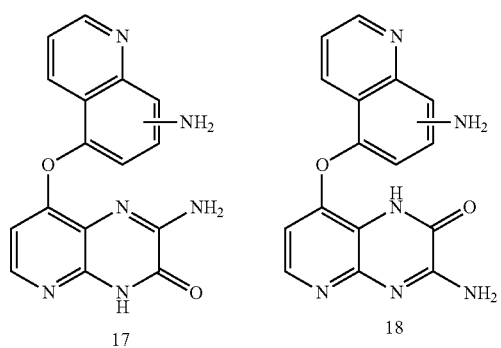
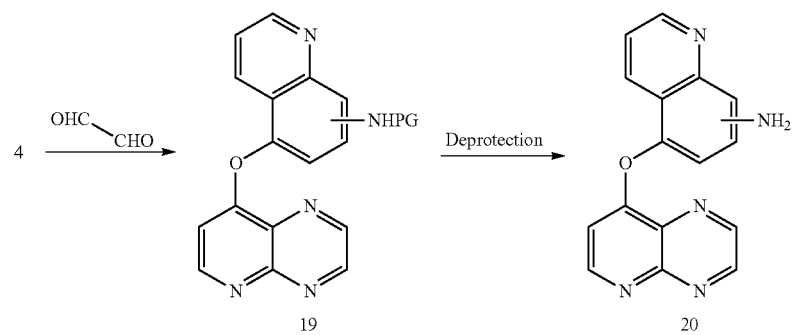

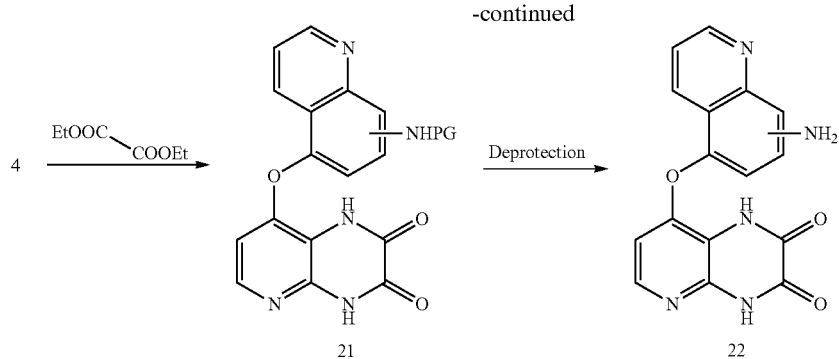

Substituted pyridopyrazines (27) and (28) can be obtained from intermediates (7) and (8). The carbonyl group of the pyrazinone can be converted to give the chloropyrazine intermediates (23) or (24) with PPh₃ and N-chlorosuccinimide, and then the chloro group substituted with ammonia, primary or secondary amine, alcohols and thiols to afford amines, ethers and thioethers (25) or (26). Deprotection affords the common intermediates (27) or (28). See, for example, the following scheme.

Scheme 4

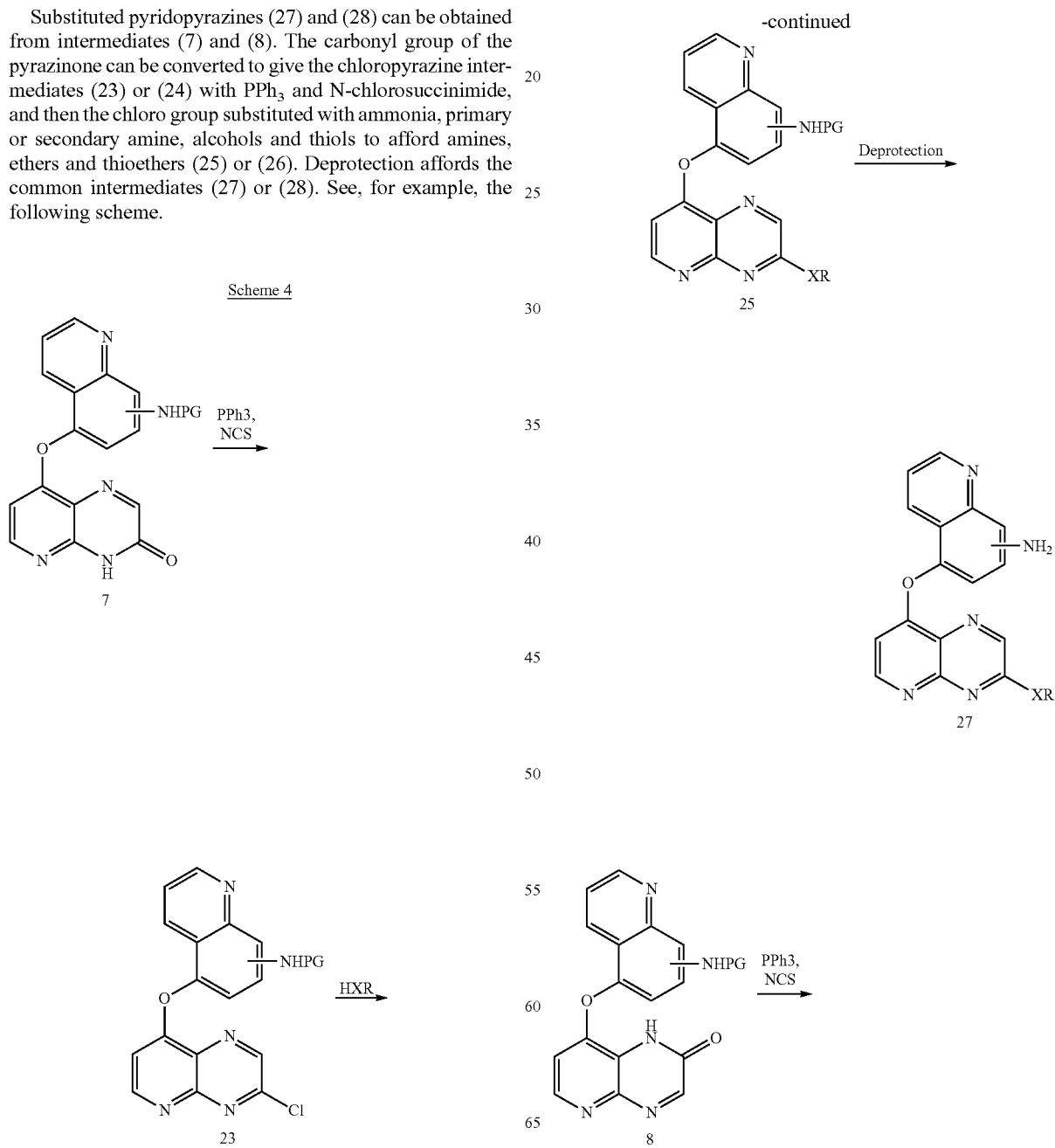

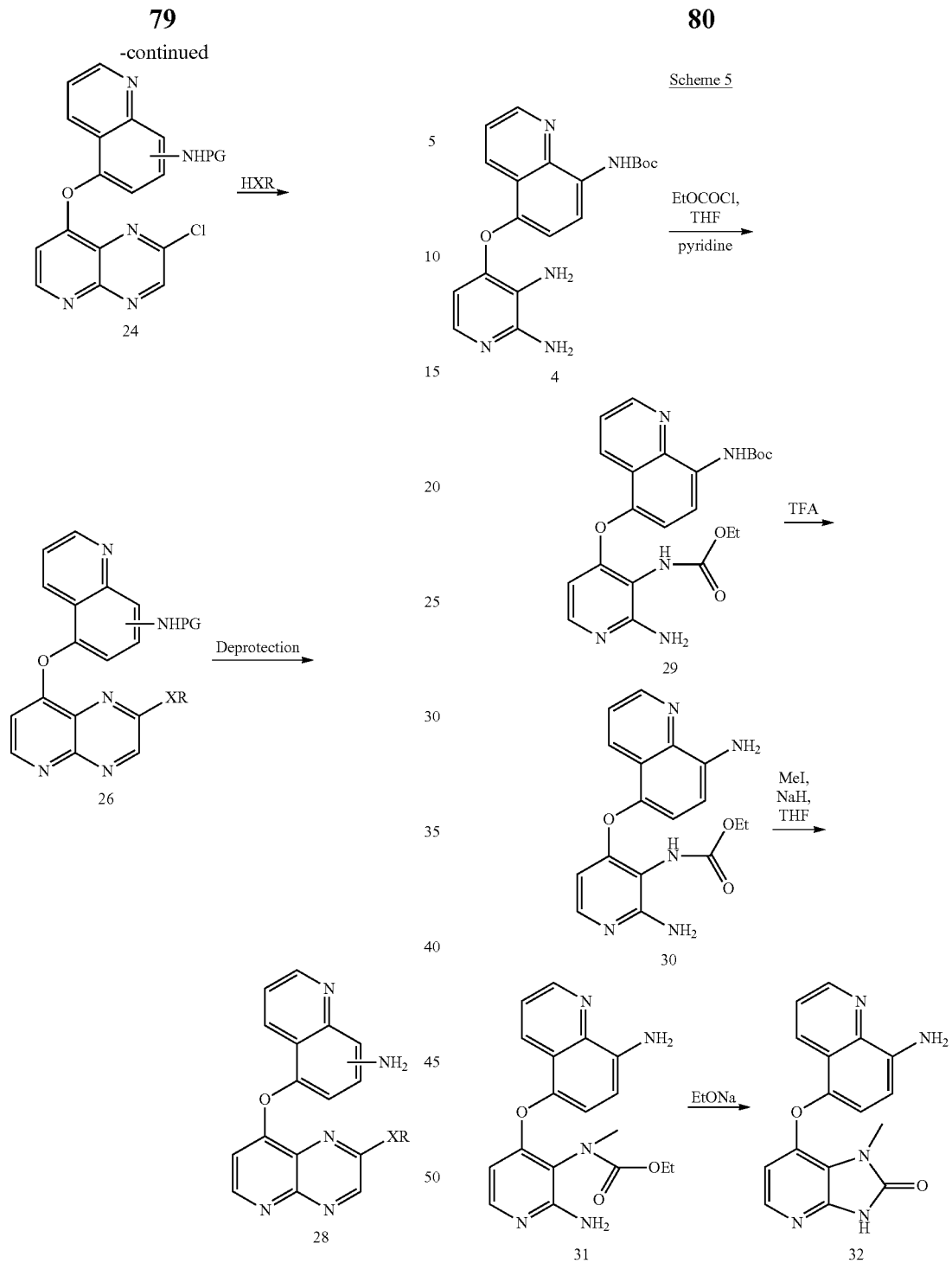

Scheme 5

In another approach, the key intermediate (32) is prepared starting from intermediate (4). The more nucleophilic 3-amino group on the pyridine is selectively converted to a carbamate, the BOC group is deprotected, and the carbamate is alkylated. The ring closure under basic conditions affords imidazo[4,5-b]pyridine-2-one.

For example, intermediate (4) is converted to ethyl carbamate (29) and the BOC group is removed with TFA to afford (30). Deprotonation of the acidic carbamate proton with NaH creates an anion on N-3 that is alkylated to afford the intermediate (31). Intermediate (31) is cyclised to the common intermediate (32) in the presence of base. An example of such a method is illustrated in the following scheme.

In another approach, compounds substituted at the N-2 position (with respect to the pyridine ring) can be obtained by alkylation of the amino group of the starting material.

For example, 2-amino-3-nitro-4-chloropyridine, (1), is Boc-protected at the amino group, methylated with MeI and NaH and the Boc protection removed to afford (33). Intermediate (33) can be used similarly to intermediate 1 to afford the common intermediate (34), using the same method described in Scheme 1 above. An example of such a method is illustrated in the following scheme.

Scheme 6

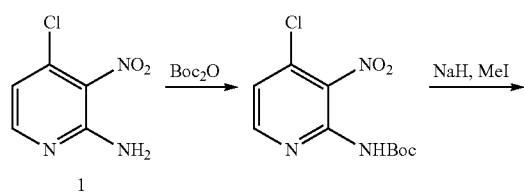

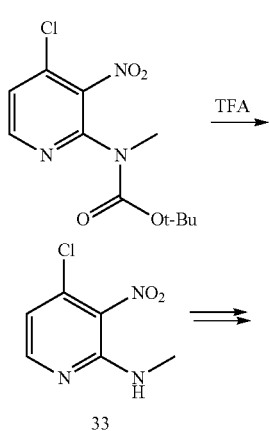

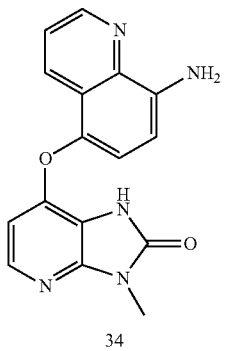

Scheme 7

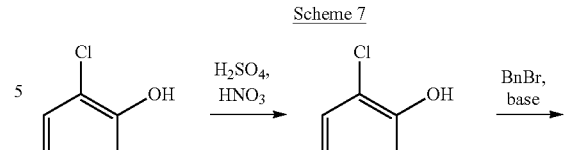

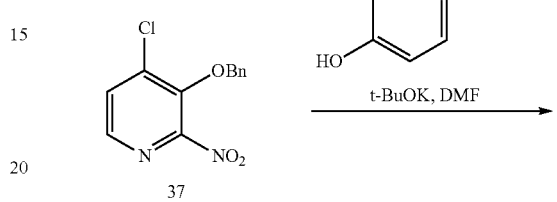

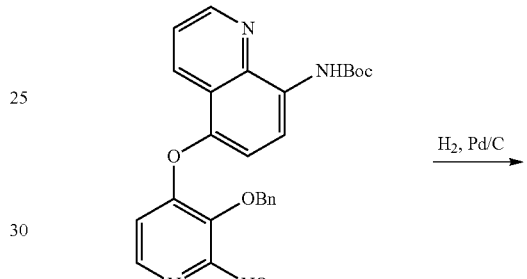

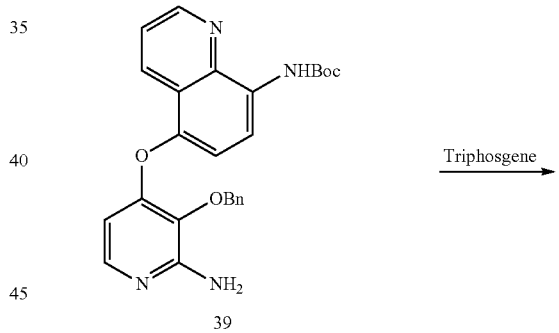

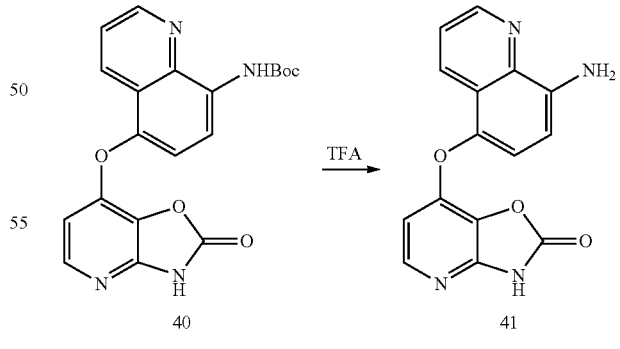

In another approach, another key intermediate is prepared from the commercially available reagent 3-hydroxy-4-chloro-pyridine. The reagent is nitrated, the hydroxyl group is protected as benzyl ether, and the chloro group is replaced with a BOC-protected hydroxyl-amino-quinoline/isoquinoline. The benzyl group is removed concomitant with the reduction of the nitro function. Then, the ring is closed using triphosgene, phosgene or carbonyldiimidazole, and the initial amino group is deprotected to give the desired intermediate pyridoimidazolone.

For example, 3-hydroxy-4-chloropyridine (35) is nitrated selectively in the 2-position, then the phenol protected as Bn ether to afford (37). Displacement of the 4-chloro with 8-N-BOC-amino-5-hydroxyquinoline yields (38). This intermediate is then reduced to convert the nitro group to amino simultaneously with the removal of benzyl protection to generate (39). Ring closure with triphosgene followed by deprotection with TFA affords the common intermediate (41). See, for example, the following scheme.

The key intermediates (6), (9), (10), (13), (14), (17), (18), (20), (22), (27), (28), (32), (34), and (41) may then be used to prepare a range of compounds with different linker groups, L, and different terminal groups, A. This is exemplified bellow with intermediate (6), but it is applicable to any of the key intermediates shown above.

For example, the intermediate (6) can be reacted with activated carboxylic acids or acid chloride to afford amides (NHCO); with activated thioacetic acids to afford thioamide (NHCS); with isocyanates to afford ureas (NHCONH); with activated carbamates to afford ureas (NHCONH); with isothiocyanates to afford thioureas (NHCSNH); with sulfonyl chlorides to afford sulfonamides (SO$_2$NH); with activated sulfamoyl derivatives to afford sulfamides (NHSO$_2$NH); with haloacetic amide to afford glycinamides (NHCH$_2$CONH).

Examples of such methods are exemplified in the following scheme with one of the quinoline groups. It should be understood that all of the other examples of common intermediates with quinoline and isoquinoline rings as described in Table 1 above and with bicyclic rings as in intermediates (9), (10), (13), (14), (17), (18), (20), (22), (27), (28), (32), (34), and (41) can be used in the same way.

Scheme 8

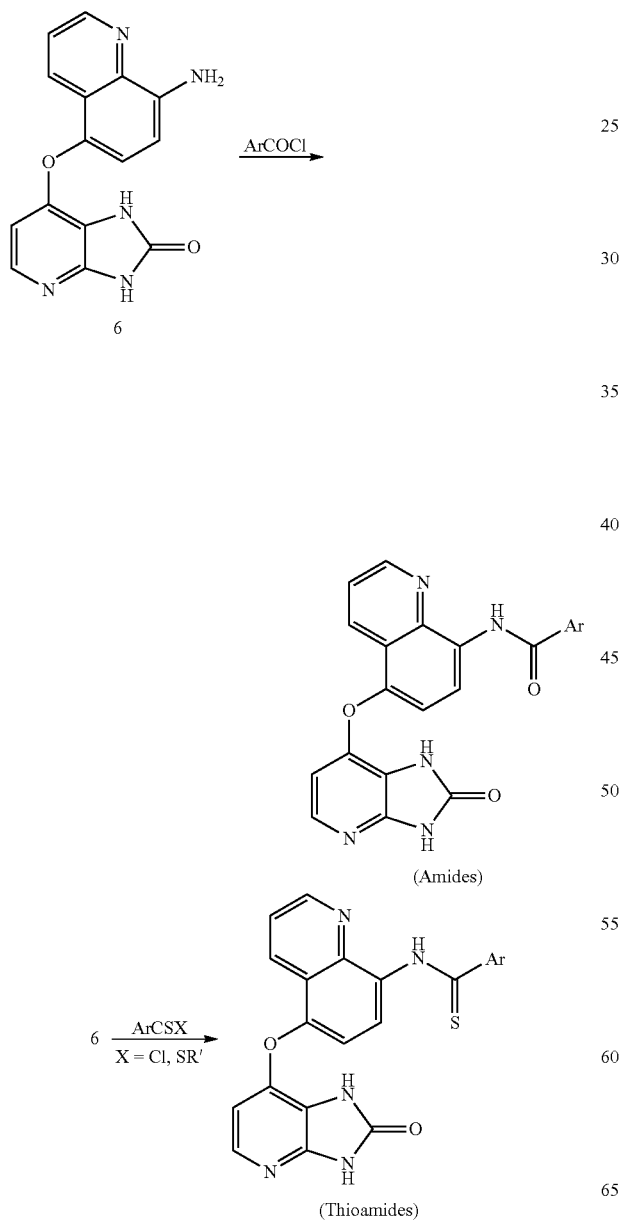

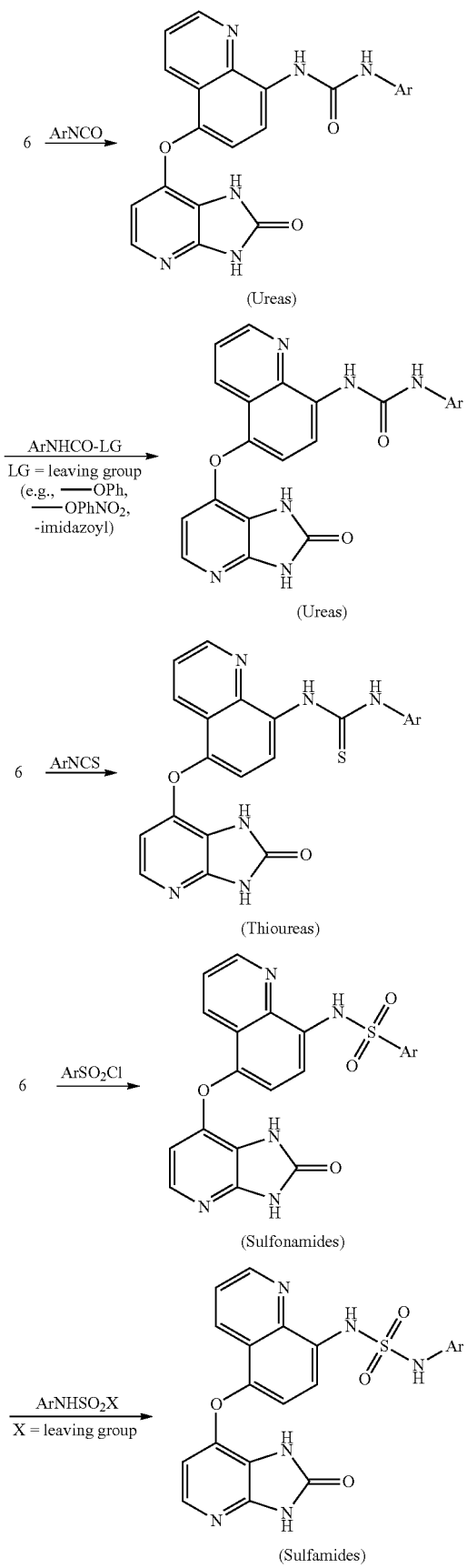

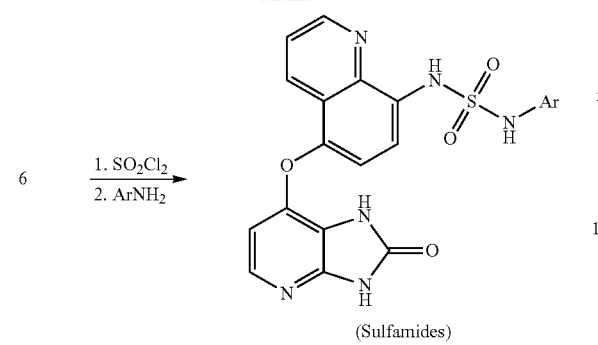

(Sulfamides)

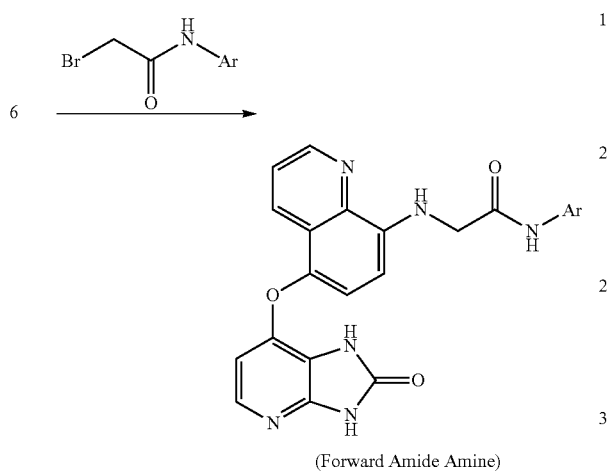

(Forward Amide Amine)

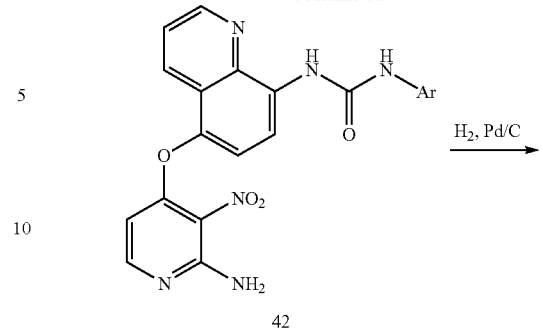

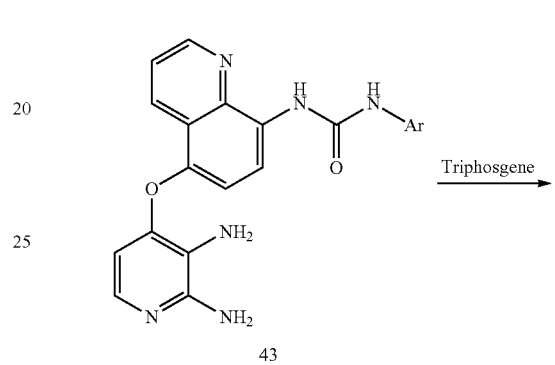

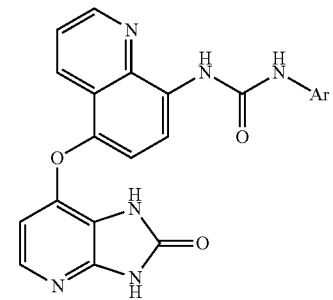

In another approach, the key intermediate (2) is first converted to a urea, thiourea, amide, thioamide, sulfonamide, or sulfamide, using a method as described in the Scheme 8 above, and then converted to any of the bicyclic systems described in Scheme 3 above. This approach is exemplified for a urea linker (L), 8-amino-5-hydroxyquinoline, and imidazo[4,5-b]pyridine-2-one bicyclic system in the following scheme. Any of the linkers L shown in Scheme 8, any of the quinoline/isoquinolines presented in Table 1 above, and any of the bicyclic systems described in Scheme 3 may be substituted. For example, the reaction of (2) with isocyanates produces ureas (42). Reduction of nitro group followed by cyclisation of (43) to imidazolones affords the final product (44). An example of such a method is illustrated in the following scheme.

Scheme 9

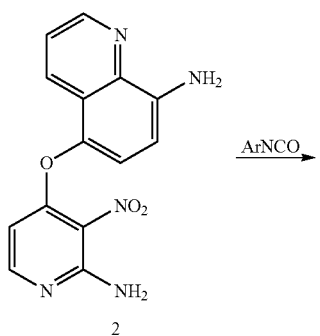

In another approach, the hydroxyl-aminoquinoline or hydroxyl-aminoisoquinoline (as shown in Table 1 above) is first converted to a urea, thiourea, amide, thioamide, sulfonamide, or sulfamide, using a method as described above, and then reacted with 2-amino-3-nitro-4-chloropyridine (1), to form intermediate (42). This intermediate is then converted to target compounds by reduction and cyclisation, for example, as described above in Scheme 8. For example, the reaction of 8-amino-5-hydroxyquinoline with isocyanates produces ureas (45).

Reaction of the hydroxyl group with 2-amino-3-nitro-4-chloropyridine (1) generates intermediate (42). Reduction of nitro group to give intermediate (43) followed by cyclisation to imidazolones affords the target compound (44). An example of such a method is illustrated in the following scheme. Alternatively, any of the linker groups, L, shown in Scheme 8 above, any of the quinolines or isoquinolines shown in Table 1 above, and any of the bicyclic systems described in Scheme 3 above, may be used, alone or in combination.

Scheme 10

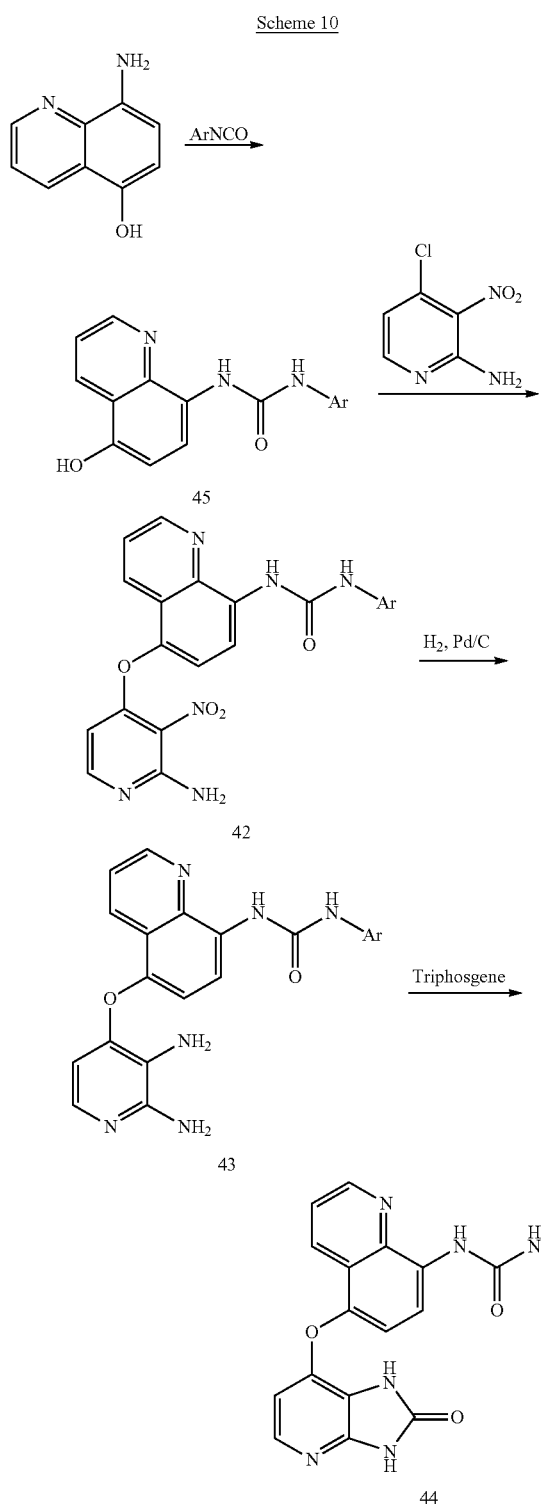

Chemical Synthesis

All starting materials, reagents and solvents for reactions were reagent grade and used as purchased. Chromatography solvents were HPLC grade and were used without further purification. Reactions were monitored by thin layer chromatography (TLC) analysis using Merck silica gel 60 F-254 thin layer plates. Flash column chromatography was carried out on Merck silica gel 60 (0.015-0.040 mm) or in disposable Isolute Flash Si and Si II silica gel columns. Preparative TLC was performed on either Macherey-Nagel [809 023] pre-coated TLC plates SIL G-25 UV$_{254}$ or Analtech [2015] pre-coated preparative TLC plates, 2000 μm with UV$_{254}$. LCMS analyses were performed on a Micromass LCT/Water's Alliance 2795 HPLC system with a Discovery 5 μm, C18, 50 mm×4.6 mm i.d. column from Supelco at a temperature of 22° C. using the following solvent systems: Solvent A: Methanol; Solvent B: 0.1% formic acid in water at a flow rate of 1 mL/min. Gradient starting with 10% A/90% B from 0-0.5 minutes then 10% A/90% B to 90% A/10% B from 0.5 minutes to 6.5 minutes and continuing at 90% A/10% B up to 10 minutes. From 10-10.5 minutes the gradient reverted back to 10% A/90% where the concentrations remained until 12 minutes. UV detection was at 254 nm and ionisation was positive or negative ion electrospray. Molecular weight scan range is 50-1000. Samples were supplied as 1 mg/mL in DMSO or methanol with 3 μL injected on a partial loop fill. NMR spectra were recorded in DMSO-d$_6$ on a Bruker Advance 500 MHz spectrometer.

Synthesis 1

4-(5-N-BOC-amino-quinolinyl-8-oxy)-5-nitro-6-amino-pyridine (3a)

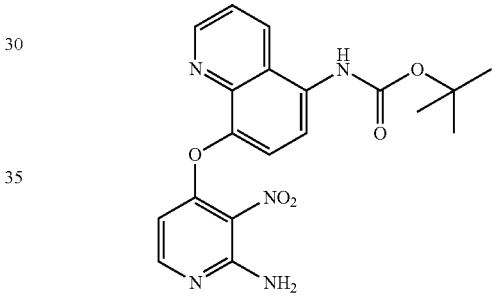

To 400 mg (2.32 mmol) of 5-N-BOC-amino-8-hydroxyquinoline dissolved in 30 mL DMF (dry), were added under stirring and argon atmosphere, 360 mg (3.20 mmol) tert-BuOK. After 30 minutes, 400 mg (2.32 mmol) 2-amino-3-nitro-4-chloropyridine were added at once and the reaction mixture heated at 85° C. (bath) for 5 hours. After cooling, 200 mL AcOEt were added and the solution extracted with 2×200 mL brine. The solution was dried (MgSO$_4$) and evaporated under vacuum. The residue was purified on an Isolute column (Flash Si II; 50 g, 170 mL) eluted with AcOEt. The title compound was obtained as a yellow solid: 0.534 g. Yield: 58%. $^1$H NMR (500 MHz, DMSO-d$_6$) δ: 1.51 (s, 9H, C(CH$_3$)$_3$), 5.65 (d, 1H, H$_{Pyr}$, J=5.6 Hz), 7.14 (s, 2H, NH$_2$), 7.58-7.61 (m, 1H, H$_{Arom}$), 7.64 (d, 1H, H$_{Arom}$, J=8.3 Hz), 7.74 (d, 1H, H$_{Arom}$, J=8.3 Hz), 7.82 (d, 1H, H$_{Pyr}$), 8.53-8.55 (m, 1H, H$_{arom}$), 8.84-8.86 (m, 1H, H$_{arom}$), 9.51 (s, 1H, NH); LC-MS, t$_R$=6.51 min, m/z: 397.1 (M)$^+$, calcd for C$_{19}$H$_{19}$N$_5$O$_5$.

Synthesis 2

4-(8-N-BOC-amino-quinolinyl-5-oxy)-5-nitro-6-amino-pyridine (3b)

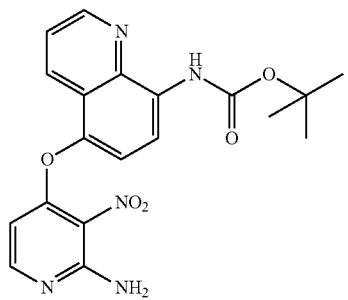

Starting from 1.2 g (4.61 mmol) 8-N-BOC-amino-5-hydroxy-quinoline and using the same procedure as described for (3a), 1.048 g of the title compound were obtained after purification by chromatography. Yield: 57%. $^1$H NMR (500 MHz, DMSO-$d_6$) δ: 1.54 (s, 9H, C(CH$_3$)$_3$), 5.89 (d, 1H, H$_{Pyr}$, J=5.6 Hz), 7.24 (s, 2H, NH$_2$), 7.48 (d, 1H, J=8.4 Hz, H$_{Arom}$), 7.69-7.72 (m, 1H, H$_{Arom}$), 7.92 (d, 1H, H$_{Pyr}$), 8.28-8.32 (m, 2H, H$_{arom}$), 8.96-8.97 (m, 2H, NH+H$_{Arom}$); LC-MS, t$_R$=8.39 min, m/z: 397.1 (M)$^+$, calcd for C$_{19}$H$_{19}$N$_5$O$_5$.

Synthesis 3

4-(5-N-BOC-amino-quinolinyl-8-oxy)-5,6-diamino-pyridine (4a)

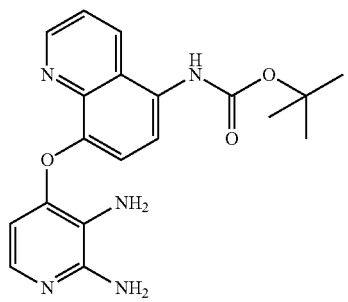 [SMILES: CC(C)(C)OC(=O)Nc1ccc(Oc2ccnc(N)c2[N+](=O)[O-])c2ncccc12]

2.5 g (6.29 mmol) 4-(5-N-BOC-amino-quinolinyl-8-oxy)-5-nitro-6-amino-pyridine (3a) dissolved in 300 mL AcOEt:EtOH 1:1, were hydrogenated at room temperature in the presence of 480 mg Pd/C 10% catalyst. After 18 hours, the catalyst was filtered and the solvent evaporated under vacuum. The residue thus obtained was purified on an Isolute column (Flash Si II; 50 g/170 mL) using AcOEt:EtOH 9:1 as eluent. After evaporation of the solvent, 1.120 g of the title compound were obtained. Yield: 49%. $^1$H NMR (500 MHz, DMSO-$d_6$) δ: 1.50 (s, 9H, C(CH$_3$)$_3$), 4.48 (s, 2H, NH$_2$), 5.51 (s, 2H, NH$_2$), 5.78 (d, 1H, H$_{Pyr}$, J=5.7 Hz), 7.15 (m, 1H, J=5.6 Hz, H$_{Arom}$), 7.31 (d, 1H, H$_{Arom}$, J=8.3 Hz), 7.58 (m, 2H, H$_{Pyr}$+H$_{Arom}$), 8.45 (m, 1H, H$_{Arom}$), 8.86-8.88 (m, 1H, H$_{arom}$), 9.33 (s, 1H, NH); LC-MS, t$_R$=3.89 min, m/z: 367.1 (M)$^+$, calcd for C$_{19}$H$_{21}$N$_5$O$_3$.

Synthesis 4

4-(8-N-BOC-amino-quinolinyl-5-oxy)-5,6-diamino-pyridine (4b)

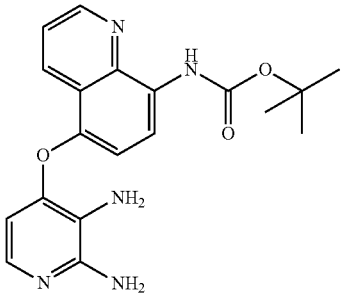 [SMILES: CC(C)(C)OC(=O)Nc1ccc(Oc2ccnc(N)c2N)c2cccnc12]

1.037 g (2.61 mmol) 4-(8-N-BOC-amino-quinolinyl-5-oxy)-5-nitro-6-amino-pyridine (3b) dissolved in 200 mL AcOEt:EtOH 1:1 were hydrogenated using a hydrogenation cube and a Pd/C 10% cartridge. The flow rate was 1 mL/min. After solvent evaporation, 0.941 g of the title compound were obtained. Yield: 98%. $^1$H NMR (500 MHz, DMSO-$d_6$) δ: 1.53 (s, 9H, C(CH$_3$)$_3$), 4.60 (s, 2H, NH$_2$), 5.65 (s, 2H, NH$_2$), 5.92 (d, 1H, H$_{Pyr}$, J=5.7 Hz), 7.11 (d, 1H, J=8.5 Hz, H$_{Arom}$), 7.19 (d, 1H, H$_{Pyr}$, J=5.6 Hz), 7.67 (m, 1H, H$_{Arom}$), 8.19 (d, 1H, J=8.5 Hz, H$_{Arom}$), 8.43 (m, 1H, H$_{arom}$), 8.87 (s, 1H, NH), 8.94 (m, 1H, H$_{Arom}$); LC-MS, t$_R$=5.02 min, m/z: 367.1 (M)$^+$, calcd for C$_{19}$H$_{21}$N$_5$O$_3$.

Synthesis 5

4-(5-Amino-quinolinyl-8-oxy)-pyridine-5,6-imidazolone (6a)

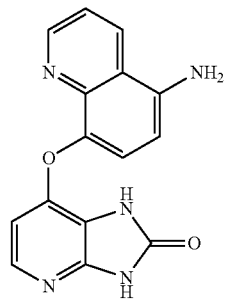 [SMILES: Nc1ccc(Oc2ccnc3[nH]c(=O)[nH]c23)c2ncccc12]

Cyclisation: 1.071 g (2.92 mmol) 4a and 1.370 mL (16.9 mmol) pyridine were dissolved in 50 mL THF dry, under stirring and argon atmosphere. The reaction mixture was cooled (ice bath) and a solution of 0.893 g (3.0 mmol) triphosgene in 20 mL dry THF was added dropwise over 1 hour. The reaction mixture was allowed to reach room temperature and then stirred for an additional 16 hours. The reaction mixture was evaporated under vacuum, 4-5 mL acetone were added, followed by 50 mL H$_2$O. The precipitate was filtered, dried and redissolved in 50 mL dry THF and 1.3 mL pyridine.

The solution was refluxed for 24 hours and the same work up repeated. 0.769 g of 4-(5-N-BOC-amino-quinolinyl-8-oxy)-pyridine-5,6-imidazolone, 5a, was obtained.

Deprotection: 0.769 g of 5a were dissolved at room temperature in 15 mL TFA and stirred for 2.5 hours. The solution was evaporated under vacuum and 2×10 mL AcOEt was added, and the solutions evaporated again under vacuum. The oily residue was dissolved in 20 mL H$_2$O and adjusted to pH 7.5-8.0 with Na$_2$CO$_3$ solution. The precipitate was filtered, washed (H$_2$O) and dried, providing 0.520 g of the title compound. Yield: 61% (over 2 steps). $^1$H NMR (500 MHz, DMSO-d$_6$) δ: 5.89 (d, 1H, H$_{Pyr}$, J=5.7 Hz), 6.04 (s, 2H, NH$_2$), 6.72 (d, 1H, J=8.2 Hz, H$_{Arom}$), 7.37 (d, 1H, H$_{Arom}$, J=8.2 Hz), 7.41-7.44 (m, 1H, H$_{Arom}$), 7.54 (d, 1H, H$_{Pyr}$), 8.58 (m, 1H, H$_{Arom}$), 8.70 (m, 1H, H$_{arom}$), 11.18 (s, 1H, NH), 11.21 (s, 1H, NH); LC-MS, t$_R$=2.63 min, m/z: 293.1 (M)$^+$, calcd for C$_{15}$H$_{11}$N$_5$O$_2$.

Synthesis 6

4-(8-Amino-quinolinyl-5-oxy)-pyridine-5,6-imidazolone (6b)

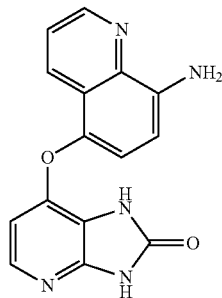 [SMILES: Nc1ccc(Oc2ccnc3[nH]c(=O)[nH]c23)c2cccnc12]

Cyclisation: 370 mg (1.0 mmol) 4b and 0.470 mL (5.85 mmol) pyridine were dissolved in 20 mL THF dry, under stirring and argon atmosphere. The reaction mixture was cooled (ice bath) and a solution of 300 mg (1.01 mmol) triphosgene in 5 mL dry THF was added dropwise over 1 hour. The reaction mixture was allowed to reach room temperature and then stirred for an additional 16 hours. The reaction mixture was evaporated under vacuum, 4 mL acetone were added, followed by 50 mL H$_2$O. The precipitate was filtered, dried and redissolved in 20 mL dry THF and 0.5 mL pyridine. The solution was refluxed for 24 hours and the same work up repeated. 368 mg of 4-(8-N-BOC-amino-quinolinyl-5-oxy)-pyridine-5,6-imidazolone, 5b, was obtained.

Deprotection: 300 mg of 5b were dissolved at room temperature in 10 mL TFA and stirred for 2.5 hours. The solution was evaporated under vacuum and 2×10 mL AcOEt was added and the solutions evaporated again under vacuum. The oily residue was dissolved in 20 mL H$_2$O and adjusted to pH 7.5-8.0 with Na$_2$CO$_3$ solution. The precipitate was filtered, washed (H$_2$O) and dried, resulting in 275 mg of the title compound. Yield: 94% (over 2 steps). $^1$H NMR (500 MHz, DMSO-d$_6$) δ: 5.99 (s, 2H, NH$_2$), 6.11 (d, 1H, H$_{Pyr}$, J=5.9 Hz), 6.87 (d, 1H, J=8.2 Hz, H$_{Arom}$), 7.22 (d, 1H, H$_{Arom}$, J=8.2 Hz), 7.49-7.51 (m, 1H, H$_{Arom}$), 7.64 (d, 1H, H$_{Pyr}$), 8.10 (d, 1H, J=7.5 Hz, H$_{Arom}$), 8.79 (d, 1H, J=1.8 Hz, H$_{arom}$), 11.26 (s, 1H, NH), 11.31 (S, 1H, NH).

Synthesis 7

4-(8-N-BOC-amino-quinolinyl-5-oxy)-5-N-carbamoylethyl-6-amino-pyridine (29)

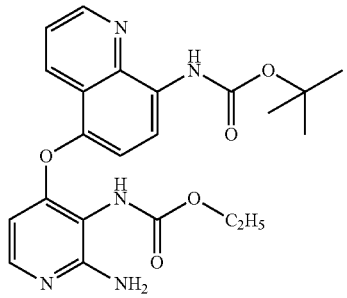 [SMILES: CCOC(=O)Nc1c(Oc2ccc(NC(=O)OC(C)(C)C)c3ncccc23)ccnc1N]

To a solution containing 900 mg (2.45 mmol) 4-(8-N-BOC-amino-quinolinyl-5-oxy)-5,6-diamino-pyridine, 4b, and 2.8 mL pyridine, in 25 mL THF (extra dry), under stirring, argon atmosphere and at 0° C., 1.52 mL ethylchloroformate were added at once. After 30 minutes, the reaction mixture was allowed to reach room temperature and was stirred for an extra 18 hours. The reaction mixture was evaporated to dryness and the resulted solid partitioned between AcOEt (30 mL) and a solution of Na$_2$CO$_3$ (30 mL). The organic layer was washed with brine (2×30 mL), dried and evaporated under vacuum. The residue was purified by flash chromatography, using an Isolute column (Flash Si II; 50 g/170 mL), to give 805 mg of the title compound. Yield: 75%. $^1$H NMR (500 MHz, DMSO-d$_6$) δ: 1.17 (t, 3H, J=3.4 Hz, CH$_3$), 1.54 (s, 9H, C(CH$_3$)$_3$), 4.04 (q, 2H, CH$_2$), 5.71 (d, 1H, H$_{Pyr}$, J=5.7 Hz), 5.86 (s, 1H, H$_{Arom}$), 7.29 (d, 1H, J=8.3 Hz, H$_{Arom}$), 7.62 (d, 1H, H$_{Pyr}$), 7.65-7.67 (m, 1H, H$_{Arom}$), 8.25 (d, 1H, J=8.3 Hz, H$_{Arom}$), 8.40 (s, broad, 2H, 2×NH), 8.93 (d, 1H, J=1.8 Hz, H$_{arom}$).

Synthesis 8

4-(8-Amino-quinolinyl-5-oxy)-5-N-carbamoylethyl,6-amino-pyridine (30)

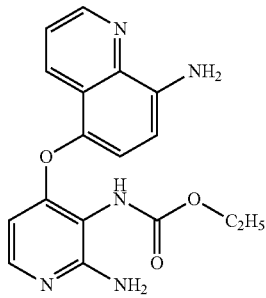 [SMILES: CCOC(=O)Nc1c(Oc2ccc(N)c3ncccc23)ccnc1N]

850 mg 4-(8-N-BOC-amino-quinolinyl-5-oxy)-5-N-carbamoylethyl,6-amino-pyridine (17) were dissolved in 15 mL TFA at room temperature under stirring. After 2.5 hours, the solution was evaporated under vacuum and 2×10 mL AcOEt were added and the solutions evaporated again under vacuum.

The oily residue was dissolved in 20 mL H₂O and adjusted to pH 7.5-8.0 with Na₂CO₃ solution. The precipitate was filtered, washed (H₂O), dried, and recrystallised from AcOEt giving 500 mg of the title compound. Yield: 77%. $^1$H NMR (500 MHz, DMSO-$d_6$) δ: 1.16 (t, 3H, J=3.4 Hz, CH₃), 4.04 (q, 2H, CH₂), 5.60 (d, 1H, $H_{Pyr}$, J=5.7 Hz), 5.92 (s, 2H, NH₂), 5.86 (s, 2H, NH₂), 6.85 (d, 1H, J=8.2 Hz, $H_{Arom}$), 7.08 (d, 1H, J=8.2 Hz, $H_{Arom}$), 7.42-7.48 (m, 1H, $H_{Arom}$), 7.57 (d, 1H, $H_{Pyr}$), 8.25 (s, broad, 1H, NH), 8.77 (m, 1H, $H_{arom}$).

Synthesis 9

4-(8-Amino-quinolinyl-5-oxy)-5-N-carbamoylethyl-N-methyl,6-amino-pyridine (31)

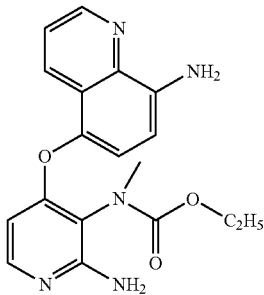 [SMILES: CCOC(=O)N(C)c1c(Oc2ccc(N)c3ncccc23)ccnc1N]

To a solution containing 485 mg (1.45 mmol) 4-(8-amino-quinolinyl-5-oxy)-5-N-carbamoylethyl-6-amino-pyridine (18) in 20 mL DMF dry, under stirring and argon, at 0° C., 78 mg (1.93 mmol) NaH in mineral oil 60% was added at once. The reaction mixture was stirred for 40 minutes, then 100 μL (1.61 mmol) methyl iodide were added at once. After 30 minutes, the reaction mixture was allowed to reach room temperature and was stirred for an extra 16 hours. At the end, the reaction mixture was diluted with 100 mL AcOEt and extracted with brine (2×100 mL). The organic layer was dried and evaporated to 4-5 mL, to yield a precipitate as a yellow solid. After recrystallisation of the precipitate from AcOEt, 140 mg of the title compound were obtained. Yield: 27%. $^1$H NMR (500 MHz, DMSO-$d_6$) δ: 1.15 (t, 3H, J=3.4 Hz, CH₃), 3.36 (s, 3H, CH₃), 4.04 (q, 2H, CH₂), 5.56 (d, 1H, $H_{Pyr}$, J=5.8 Hz), 5.95 (s, 2H, NH₂), 5.99 (s, 1H, NH₂), 6.20 (s, 1H, $H_{Arom}$), 7.07 (d, 1H, J=8.3 Hz, $H_{Arom}$), 7.08 (d, 1H, J=8.2 Hz, $H_{Arom}$), 7.48-7.51 (m, 1H, $H_{Arom}$), 7.58 (d, 1H, $H_{Pyr}$), 7.74 (s, 1H, $H_{Arom}$), 8.78 (m, 1H, $H_{arom}$).

Synthesis 10

4-(8-Amino-quinolinyl-5-oxy)-pyridine-5-N-methyl-6-imidazolone (32)

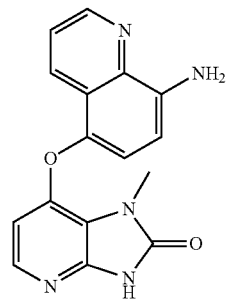 [SMILES: Cn1c(=O)[nH]c2nccc(Oc3ccc(N)c4ncccc34)c21]

140 mg (0.4 mmol) of 4-(8-amino-quinolinyl-5-oxy)-5-N-carbamoylethyl-N-methyl-6-amino-pyridine (19) suspended in 5 mL of a solution of NaOEt/EtOH 1.0 M in a microwave tube. The sample was heated in a microwave oven for 60 minutes, at 100° C. (150 W) under stirring. After cooling, the reaction mixture was evaporated under vacuum, the residue was dissolved in 20 mL H₂O and AcOH was added to pH 5.5-6.0. The precipitate was filtered and dried resulting in 98 mg of the title compound. Yield: 80%. $^1$H NMR (500 MHz, DMSO-$d_6$) δ: 3.60 (s, 3H, CH₃), 5.98 (s, 2H, NH₂), 6.13 (d, 1H, $H_{Pyr}$, J=5.7 HZ), 6.88 (d, 1H, J=8.2 Hz, $H_{Arom}$), 7.21 (d, 1H, J=8.2 HZ, $H_{Arom}$), 7.49-7.51 (m, 1H, $H_{Arom}$), 7.65 (d, 1H, $H_{Pyr}$), 8.22-8.24 (m, 1H, $H_{Arom}$), 8.80 (m, 1H, $H_{arom}$), 11.4 (s, 1H, NH).

Synthesis 11

4-(5-Amino-quinolinyl-8-oxy)-pyridine-5,6-N-methyl-imidazolone (34)

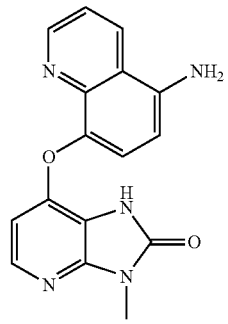 [SMILES: Cn1c(=O)[nH]c2c(Oc3ccc(N)c4cccnc34)ccnc21]

Cyclisation: 500 mg (1.30 mmol) 4-(5-amino-quinolinyl-8-oxy)-5,6-N-methyl-diamino-pyridine- and 630 μL (16.9 mmol) pyridine were dissolved in 25 mL THF dry, under stirring and argon atmosphere. The reaction mixture was cooled (ice bath) and a solution of 401 mg (1.35 mmol) triphosgene in 10 mL dry THF was added dropwise over 1 hour. The reaction mixture was allowed to reach room temperature and then stirred for an additional 16 hours. The reaction mixture was evaporated under vacuum, 4-5 mL acetone were added followed by 50 mL H₂O. The precipitate was filtered, dried, giving 512 mg (yield 96%) of 4-(5-N-BOC-amino-quinolinyl-8-oxy)-pyridine-5,6N-methyl-imidazolone. $^1$H NMR (500 MHz, DMSO-$d_6$) δ: 1.53 (s, 9H), 3.33 (s, 3H), 6.39 (d, 1H, J=5.9 Hz), 7.35 (d, 1H, J=8.5 Hz), 7.67-7.7.69 (m, 1H), 7.80 (d, 1H, J=5.9 Hz), 8.25 (d, 1H, J=8.5 Hz), 8.39 (d, 1H, J=8.0 Hz), 8.89-9.02 (m, 2H), 11.18 (s, 1H, NH), 11.54 (s, 1H, NH). HRMS: (M+H)⁺ calcd for $C_{21}H_{21}N_5O_4$ 408.1666. Found: 408.1666.

Deprotection: 4-(5-N-BOC-amino-quinolinyl-8-oxy)-pyridine-5,6N-methyl-imidazolone (100 mg, 0.21 mmol) were dissolved in 8 mL TBAF solution in THF 1.0 M, and refluxed for 48 hours. The solvent was evaporated under vacuum, 20 mL H₂O was added and the precipitate filtered and dried, resulting in 71 mg of the title compound. Yield: 93%. $^1$H NMR (500 MHz, DMSO-$d_6$) δ: δ: 3.32 (s, 3H), 5.99 (s, 2H, NH₂), 6.17 (d, 1H, J=6.0 Hz), 6.88 (d, 1H, J=8.3 Hz), 7.22 (d, 1H, J=8.3 Hz), 7.47-7.7.51 (m, 1H), 7.72 (d, 1H, J=6.0 Hz), 8.09 (d, 1H, J=5.8 Hz), 8.79-8.82 (m, 1H), 11.54 (s, 1H, NH), 11.54 (s, 1H, NH). HRMS: (M+H)⁺ calcd for C₁₆H₁₄N₅O₂ 308.1142. Found: 308.1144.

Synthesis 12

5-(8-BOC-amino-quinolinyl-5-oxy)-pyridin-[2,3]-3-methylpyrazin-2-one (11)

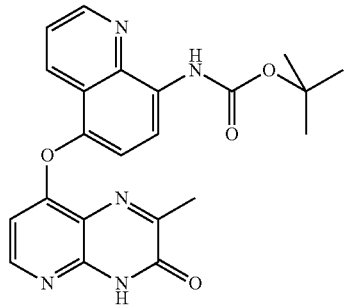 [SMILES: Cc1nc2c(Oc3ccc(NC(=O)OC(C)(C)C)c4ncccc34)ccnc2[nH]c1=O]

To 500 mg (1.36 mmol) of 4-(8-BOC-amino-quinolinyl-5-oxy)-5,6-diaminopyridine dissolved in 15 mL EtOH under stirring and at reflux, 246 µL (2.22 mmol) of ethyl piruvate was added at once. The reaction was continued for another 2 hour, and then allowed to reach room temperature. The solid thus formed was filtered to give 230 mg (yield, 40%) of the title compound as a white solid. ¹H NMR (500 MHz, DMSO-d₆) δ 1.55 (s, 9H), 2.46 (s, 3H), 6.41 (d, 1H, J=5.7 Hz), 7.47 (d, 1H, J=8.5 Hz), 7.64-7.67 (m, 1H), 8.19 (d, 1H, J=5.7 Hz), 8.26-8.28 (m, 1H), 8.58 (d, 1H, J=8.6 Hz), 8.31 (d, 1H, J=8.6 Hz), 8.96-8.98 (m, 1H), 8.99 (s, 1H, NH), 12.80 (s, 1H). LC-MS, t$_R$=2.67 min, m/z: 420.2 (M+H)⁺, calcd for C₂₂H₂₁N₅O₄; HRMS: (M+H)⁺ calcd for C₂₂H₂₁N₅O₄, 420.1666. Found: 420.1664.

Synthesis 13

5-(8-Amino-quinolinyl-5-oxy)-pyridin-[2,3]-3-methylpyrazin-2-one (13)

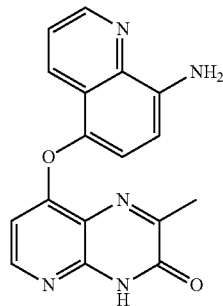 [SMILES: Cc1nc2c(Oc3ccc(N)c4ncccc34)ccnc2[nH]c1=O]

To 200 mg (0.48 mmol) of 4-(8-BOC-amino-quinolinyl-5-oxy)-5,6-diamino pyridine dissolved in mL TBAF and refluxed for 24 hours. The solvent was evaporated under vacuum and 10 mL of water added. The titled compound precipitated as a white solid, 100 mg (yield, 65%). ¹H NMR (500 MHz, DMSO-d₆) δ 2.48 (s, 3H), 6.04 (s, 2H, NH₂), 6.27 (d, 1H, J=5.7 Hz), 6.91 (d, 1H, J=8.3 Hz), 7.25 (d, 1H, J=8.3 Hz), 7.46-7.48 (m, 1H), 8.01 (d, 1H, J=8.5 Hz), 8.13 (d, 1H, J=5.7 Hz), 8.80 (m, 1H), 12.73 (s, 1H). LC-MS, t$_R$=1.67 min, m/z: 320 (M+H)⁺, calcd for C₁₇H₁₃N₅O₂; HRMS: (M+H)⁺ calcd for C₁₇H₁₃N₅O₂, 320.1142. Found: 320.1157.

Synthesis 14

4-[(5-Amino-quinolinyl-8-oxy)carbonylamino-(2-fluoro-5-trifloromethylphenyl)]-pyridin-5,6-imidazolone (AA-001)

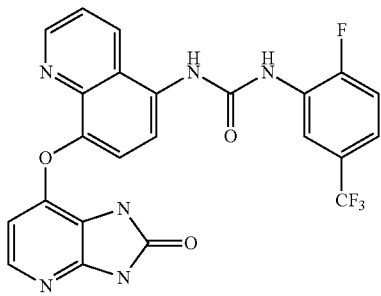 [SMILES: O=C(Nc1cc(C(F)(F)F)ccc1F)Nc1ccc(Oc2ccnc3[nH]c(=O)[nH]c23)c2ncccc12]

To 40 mg (0.14 mmol) of 4-(5-amino-quinolinyl-8-oxy)-pyridin-5,6-imidazolone, 6a, dissolved in 5 mL of THF, were added under stirring and inert atmosphere 24 µL (33 mg, 0.16 mmol) of 2-fluoro-3-trifluoromethyl-phenyl isocyanate. The reaction mixture was stirred at 40° C. for 20 hours. The solvent was evaporated, the solid residue triturated with Et₂O and filtered. 33.4 mg (yield, 48%) of the title compound were obtained. ¹H NMR (500 MHz, DMSO-d₆) δ 6.01 (d, 1H, H$_{Pyr}$, J=5.9 Hz), 7.37-7.72 (m, 5H, H$_{Pyr}$+H$_{Arom}$), 8.11 (d, 1H, J=8.4 Hz, H$_{Arom}$), 8.64 (d, 1H, J=6.8 Hz, H$_{Arom}$), 8.67 (d, 1H, H$_{Arom}$, J=7.2 Hz), 8.89 (d, 1H, J=5.4 Hz, H$_{Arom}$), 9.34 (s, 1H, NH$_{urea}$), 9.50 (s, 1H, NH$_{urea}$), 11.26 (s, 1H, NH), 11.31 (s, 1H, NH); LC-MS, t$_R$=4.71 min, m/z: 498.1 (M)⁺, calcd for C₂₃H₁₄N₆O₃F₄.

Synthesis 15

4-[(8-Oxy-quinolinyl-5-amino)carbonylamino-(3-trifluoromethyl-4-chloro-phenyl)]-pyridin-5,6-imidazolone (AA-002)

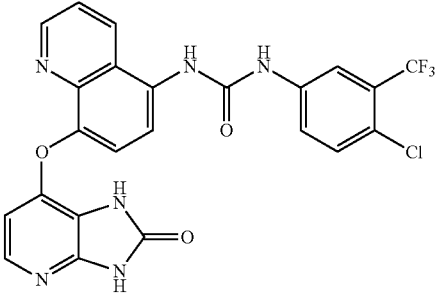 [SMILES: O=C(Nc1ccc(Cl)c(C(F)(F)F)c1)Nc1ccc(Oc2ccnc3[nH]c(=O)[nH]c23)c2ncccc12]

To 40 mg (0.14 mmol) of 4-(5-amino quinolinyl-8-oxy)-pyridin-5,6-imidazolone, 6a, dissolved in 5 mL of THF, were added under stirring and inert atmosphere 36 mg (0.16 mmol) of 3-trifluoromethyl-4-chloro-phenyl isocyanate. The reaction mixture was stirred at 40° C. for 20 hours. The solvent was evaporated, the solid residue triturated with Et₂O and filtered. 49 mg (yield, 68%) of the title compound were obtained. ¹H NMR (500 MHz, DMSO-d₆) δ: 6.02 (d, 1H, $H_{Pyr}$, J=5.9 Hz), 7.36-7.77 (m, 5H, $H_{Pyr}$+$H_{Arom}$), 7.97 (d, 1H, J=8.4 Hz, $H_{Arom}$), 8.16 (d, 1H, J=2.8 Hz, $H_{Arom}$), 8.55 (d, 1H, $H_{Arom}$, J=7.2 Hz), 8.87 (d, 1H, J=2.8 Hz, $H_{Arom}$), 9.09 (s, 1H, $NH_{urea}$), 9.50 (s, ¹H, $NH_{urea}$), 11.26 (s, 1H, NH), 11.31 (s, 1H, NH); LC-MS, $t_R$=4.89 min, m/z: 515.1 (M)⁺, calcd for $C_{23}H_{14}N_6O_3ClF_3$.

Synthesis 16

4-[(8-Oxy-quinolinyl-5-amino)carbonyl-methyl-(3-trifluoro methyloxy-phenyl)]-pyridin-5,6-imidazolone (AA-003)

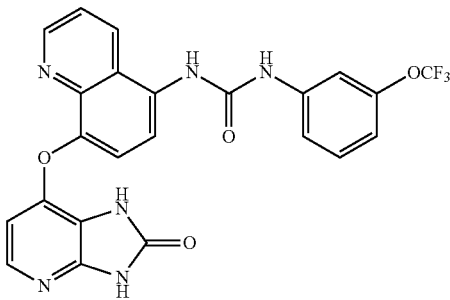 [SMILES: O=C(Nc1cccc(OC(F)(F)F)c1)Nc1ccc(Oc2ccnc3[nH]c(=O)[nH]c23)c2ncccc12]

To 50 mg (0.17 mmol) of 4-(5-amino quinolinyl-8-oxy)-pyridin-5,6-imidazolone, 6a, dissolved in 7 mL of dioxane (dry), were added under stirring and inert atmosphere 96 μL (0.20 mmol) of 3-trifluoromethyloxy-phenyl-methylene-carbonyl chloride and 150 μL triethylamine. The reaction mixture was stirred at 80° C. for 20 hours. The solvent was evaporated under vacuum, the residue washed with 5 mL water, dried and triturated with Et₂O and filtered. 39 mg (yield, 46%) of the title compound were obtained. ¹H NMR (500 MHz, DMSO-d₆) δ 3.93 (s, 2H, CH₂), 6.00 (d, 1H, $H_{Pyr}$, J=5.9 HZ), 7.25-7.81 (m, 8H, $H_{Pyr}$+$H_{Arom}$), 8.53 (d, 1H, $H_{Arom}$, J=8.3 Hz), 8.86 (d, 1H, J=2.8 Hz, $H_{Arom}$), 10.41 (s, 1H, $NH_{amide}$), 11.31 (S, 1H, NH), 11.36 (s, 1H, NH); LC-MS, $t_R$=4.32 min, m/z: 479.1 (M)⁺, calcd for $C_{24}H_{16}N_5O_4F_3$; HRMS: (M+H)⁺ calcd for $C_{24}H_{17}N_5O_4F_3$, 496.1233. Found: 496.1228.

Synthesis 17

4-[(8-Oxy-quinolinyl-5-amino)carbonyl-methyl-(3-trifluoromethyl-phenyl)]-pyridin-5,6-imidazolone (AA-004)

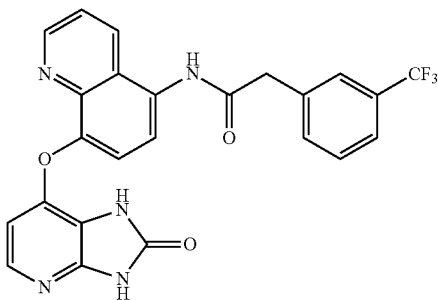 [SMILES: O=C(Cc1cccc(C(F)(F)F)c1)Nc1ccc(Oc2ccnc3[nH]c(=O)[nH]c23)c2ncccc12]

To 50 mg (0.17 mmol) of 4-(5-amino-quinolinyl-8-oxy)-pyridin-5,6-imidazolone, 6a, dissolved in 7 mL of dioxane (dry), were added under stirring and inert atmosphere 80 μL (0.20 mmol) of 3-trifluoromethyl-phenyl-methylene-carbonyl chloride and 150 μL triethylamine. The reaction mixture was stirred at 80° C. for 20 hours. The solvent was evaporated under vacuum, the residue washed with 5 mL water, dried and triturated with Et₂O and filtered. 53 mg (yield, 65%) of the title compound were obtained. ¹H NMR (500 MHz, DMSO-d₆) δ: 3.99 (s, 2H, CH₂), 6.00 (d, 1H, $H_{Pyr}$, J=5.9 Hz), 7.53-7.82 (m, 8H, $H_{Pyr}$+$H_{Arom}$), 8.57 (d, 1H, $H_{Arom}$, J=8.3 Hz), 8.86 (d, 1H, J=1.2 Hz, $H_{Arom}$), 10.43 (s, 1H, $NH_{amide}$), 11.30 (s, 1H, NH), 11.36 (s, 1H, NH); LC-MS, $t_R$=4.21 min, m/z: 479.1 (M)⁺, calcd for $C_{24}H_{16}N_5O_3F_3$; HRMS: (M+H)⁺ calcd for $C_{24}H_{17}N_6O_3F_3$, 480.1283. Found: 480.1292.

Synthesis 18

4-[(5-Oxy-quinolinyl-8-amino)carbonyl-amino-(1-N-phenyl-3-t-butyl-pyrazol-5-yl)]-pyridin-5,6-imidazolone (AA-005)

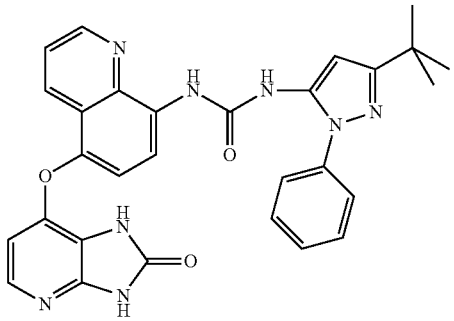

To 50 mg (0.17 mmol) of 4-(8-amino-quinolinyl-5-oxy)-pyridin-5,6-imidazolone, 6b, dissolved in 6 mL of THF (dry), were added under stirring and inert atmosphere, 1.0 mL solution containing 0.19 mmol of 1-N-phenyl-3-t-butyl-pyrazol-5-yl isocyanate. The reaction mixture was stirred at 40° C. for 20 hours. The solvent was evaporated under vacuum, the residue washed with 5 mL water, dried and triturated with Et₂O and filtered. 57 mg (yield, 63%) of the title compound were obtained. ¹H NMR (500 MHz, DMSO-d₆) δ 1.30 (s, 9H, t-Bu), 6.30 (d, 1H, $H_{Pyr}$, J=5.9 Hz), 6.43 (s, 1H, $H_{Pyrazol}$), 7.33-7.71 (m, 8H, $H_{Pyr}$+$H_{Arom}$), 8.37 (d, 1H, $H_{Arom}$), 8.52 (d, 1H, $H_{Arom}$, J=8.6 Hz), 9.08 (d, 1H, $H_{Arom}$), 9.57 (s, 1H, $NH_{urea}$), 9.94 (s, 1H, $NH_{urea}$), 11.27 (s, 1H, NH), 11.39 (s, 1H, NH); LC-MS, $t_R$=5.12 min, m/z: 534.2 (M)⁺, calcd for $C_{29}H_{27}N_8O_3$; HRMS: (M+H)⁺ calcd for $C_{29}H_{27}N_8O_3$, 535.2206. Found: 535.2208.

Synthesis 19

4-[(8-Oxy-quinolinyl-5-amino)carbonyl-amino-(1-N-phenyl-3-t-butyl-pyrazol-5-yl)]-pyridin-5,6-imidazolone (AA-006)

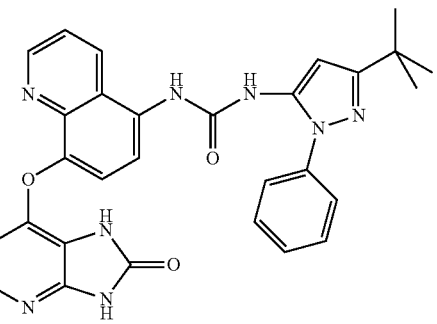

To 40 mg (0.14 mmol) of 4-(5-amino-quinolinyl-8-oxy)-pyridin-5,6-imidazolone, 6a, dissolved in 5 mL THF (dry), was added under stirring and inert atmosphere 1.0 mL solution containing 0.19 mmol of 1-N-phenyl-3-t-butyl-pyrazol-5-yl isocyanate. The reaction mixture was stirred at 40° C. for 20 hours. The solvent was evaporated under vacuum, the residue triturated with Et$_2$O and filtered. 65 mg (yield, 87%) of the title compound were obtained. $^1$H NMR (500 MHz, DMSO-d$_6$) δ: 1.29 (s, 9H, t-Bu), 5.99 (d, 1H, H$_{Pyr}$, J=5.9 Hz), 6.41 (s, 1H, H$_{Pyrazol}$), 7.44-7.63 (m, 8H, H$_{Pyr}$+H$_{Arom}$), 7.93 (d, 1H, H$_{Arom}$, J=8.3 Hz), 8.43 (d, 1H, H$_{Arom}$), 8.76 (s, 1H, NH$_{urea}$), 8.85 (d, $^1$H, H$_{Arom}$), 9.20 (s, 1H, NH$_{urea}$), 11.24 (s, 1H, NH), 11.30 (s, 1H, NH); LC-MS, t$_R$=4.63 min, m/z: 534.2 (M)$^+$, calcd for C$_{29}$H$_{27}$N$_8$O$_3$; HRMS: (M+H)$^+$ calcd for C$_{29}$H$_{27}$N$_8$O$_3$, 535.2206. Found: 535.2202.

Synthesis 20

4-[(5-Oxy-quinolinyl-8-amino)carbonylamino-(3-trifluoromethyl-4-chloro-phenyl)]-pyridin-5,6-imidazolone (AA-007)

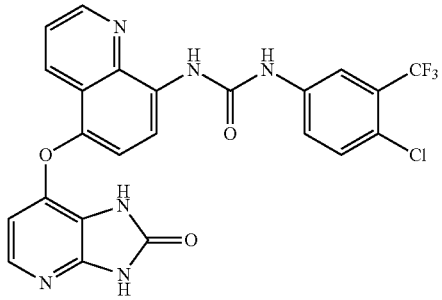 [SMILES: O=C(Nc1ccc(Cl)c(C(F)(F)F)c1)Nc1ccc(Oc2ccnc3[nH]c(=O)[nH]c23)c2cccnc12]

To 50 mg (0.17 mmol) of 4-(8-amino quinolinyl-5-oxy)-pyridin-5,6-imidazolone, 6b, dissolved in 6 mL of THF (dry), were added under stirring and inert atmosphere 40 mg (0.18 mmol) of 3-trifluoromethyl-4-chloro-phenyl isocyanate. The reaction mixture was stirred at 40° C. for 20 hours. The solvent was evaporated under vacuum, the residue triturated with Et$_2$O and filtered. 66 mg (yield, 75%) of the title compound were obtained. $^1$H NMR (500 MHz, DMSO-d$_6$) δ: 6.33 (d, 1H, H$_{Pyr}$, J=5.9 Hz), 7.37 (d, 1H, H$_{Arom}$), 7.64-7.72 (m, 6H, H$_{Pyr}$+H$_{Arom}$), 8.17 (d, 1H, J=2.2 Hz, H$_{Arom}$), 8.41 (d, $^1$H, H$_{Arom}$), 8.56 (d, 1H, J=8.5 Hz, H$_{Arom}$), 9.02 (d, 1H, J=1.8 Hz, H$_{Arom}$), 9.75 (s, 1H, NH$_{urea}$), 10.33 (s, 1H, NH$_{urea}$), 11.28 (s, 1H, NH), 11.40 (S, 1H, NH); LC-MS, t$_R$=5.44 min, m/z: 514.1 (M)$^+$, calcd for C$_{23}$H$_{14}$N$_6$O$_3$ClF$_3$; HRMS: (M+H)$^+$ calcd for C$_{23}$H$_{15}$N$_6$O$_3$ClF$_3$, 515.0846. Found: 515.0845.

Synthesis 21

4-[(5-Oxy-quinolinyl-8-amino)carbonylamino-(3-trifluoromethyl-phenyl)]-pyridin-5,6-imidazolone (AA-008)

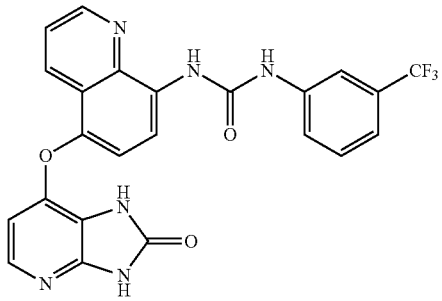 [SMILES: O=C(Nc1cccc(C(F)(F)F)c1)Nc1ccc(Oc2ccnc3[nH]c(=O)[nH]c23)c2cccnc12]

To 50 mg (0.17 mmol) of 4-(8-amino-quinolinyl-5-oxy)-pyridin-5,6-imidazolone, 6b, dissolved in 6 mL of THF (dry), were added under stirring and inert atmosphere 24 mg (0.18 mmol) of 3-trifluoromethyl-phenyl isocyanate. The reaction mixture was stirred at 40° C. for 20 hours. The solvent was evaporated under vacuum, the residue triturated with Et$_2$O and filtered. 54 mg (yield, 66%) of the title compound were obtained. $^1$H NMR (500 MHz, DMSO-d$_6$) δ 6.32 (d, 1H, H$_{Pyr}$, J=5.9 Hz), 7.37-7.72 (m, 6H, H$_{Pyr}$+H$_{Arom}$), 8.09 (s, 1H, H$_{Arom}$), 8.40 (d, 1H, J=8.2 Hz, H$_{Arom}$), 8.57 (d, 2H, H$_{Arom}$), 9.01 (d, 1H, J=2.9 Hz, H$_{Arom}$), 9.75 (s, 1H, NH$_{urea}$), 10.22 (s, 1H, NH$_{urea}$), 11.28 (s, 1H, NH), 11.40 (s, 1H, NH); LC-MS, t$_R$=5.17 min, m/z: 480.1 (M)$^+$, calcd for C$_{23}$H$_{15}$N$_6$O$_3$F$_3$; HRMS: (M+H)$^+$ calcd for C$_{23}$H$_{16}$N$_6$O$_3$F$_3$, 481.1236. Found: 481.1237.

Synthesis 22

4-[(5-Oxy-quinolinyl-8-amino)carbonylamino-(3-trifluoromethyl thio-phenyl)]-pyridin-5,6-imidazolone (AA-009)

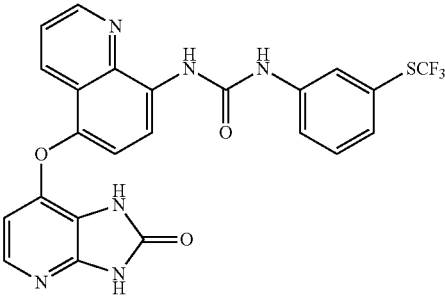

To 50 mg (0.17 mmol) of 4-(8-amino-quinolinyl-5-oxy)-pyridin-5,6-imidazolone, 6b, dissolved in 6 mL of THF (dry), were added under stirring and inert atmosphere, 40 mg (0.18 mmol) of 3-trifluoromethylthio-phenyl isocyanate. The reaction mixture was stirred at 40° C. for 20 hours. The solvent was evaporated under vacuum, the residue triturated with Et$_2$O and filtered. 61 mg (yield, 70%) of the title compound were obtained. $^1$H NMR (500 MHz, DMSO-d$_6$) δ: 6.32 (d, 1H, H$_{Pyr}$, J=5.9 Hz), 7.35-7.72 (m, 6H, H$_{Pyr}$+H$_{Arom}$), 8.06 (s, 1H, H$_{Arom}$), 8.40 (d, 1H, J=8.2 Hz, H$_{Arom}$), 8.57 (d, 2H, H$_{Arom}$), 9.01 (d, 1H, J=2.9 Hz, H$_{Arom}$), 9.74 (s, 1H, NH$_{urea}$), 10.16 (s, 1H, NH$_{urea}$), 11.28 (S, 1H, NH), 11.40 (S, 1H, NH); LC-MS, t$_R$=5.39 min, m/z: 512.1 (M)$^+$, calcd for C$_{23}$H$_{15}$N$_6$O$_3$SF$_3$; HRMS: (M+H)$^+$ calcd for C$_{23}$H$_{16}$N$_6$O$_3$SF$_3$, 513.0951. Found: 513.0957.

Synthesis 23

4-[(5-Oxy-quinolinyl-8-amino)carbonylamino-(2-fluoro-5-trifluoromethyl-phenyl)]-pyridin-5,6-imidazolone AA-010

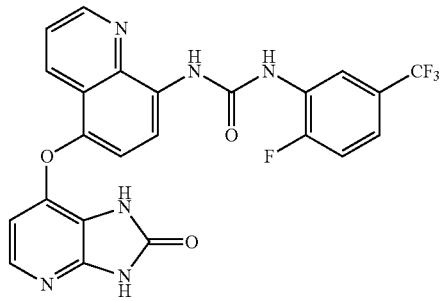 [SMILES: O=C(Nc1cc(C(F)(F)F)ccc1F)Nc1ccc(Oc2ccnc3[nH]c(=O)[nH]c23)c2cccnc12]

To 50 mg (0.17 mmol) of 4-(8-amino-quinolinyl-5-oxy)-pyridin-5,6-imidazolone, 6b, dissolved in 6 mL of THF (dry), were added under stirring and inert atmosphere 37 μL (0.18 mmol) of 2-fluoro-5-trifluoromethyl-phenyl isocyanate. The reaction mixture was stirred at 40° C. for 20 hours. The solvent was evaporated under vacuum, the residue triturated with Et$_2$O and filtered. 63 mg (yield, 74%) of the title compound were obtained. $^1$H NMR (500 MHz, DMSO-d$_6$) δ: 6.33 (d, 1H, H$_{Pyr}$, J=5.9 Hz), 7.35-7.72 (m, 5H, H$_{Pyr}$+H$_{Arom}$), 8.40 (d, 1H, J=5.4 Hz, H$_{Arom}$), 8.52 (d, 2H, H$_{Arom}$), 8.70 (d, 1H, J=6.7 Hz, H$_{Arom}$), 9.02 (d, 1H, J=2.8 Hz, H$_{Arom}$), 10.10 (s, 1H, NH$_{urea}$), 10.33 (s, 1H, NH$_{urea}$), 11.28 (s, 1H, NH), 11.40 (s, 1H, NH); LC-MS, t$_R$=5.20 min, m/z: 498.1 (M)$^+$, calcd for C$_{23}$H$_{14}$N$_6$O$_3$F$_4$; HRMS: (M+H)$^+$ calcd for C$_{23}$H$_{15}$N$_6$O$_3$F$_4$, 499.1143. Found: 499.1142.

Synthesis 24

4-[(5-Oxy-quinolinyl-8-amino)carbonyl-amino-(1-N-p-tolyl-3-t-butyl-pyrazol-5-yl)]-pyridin-5-N-methyl,6-imidazolone (AA-011)

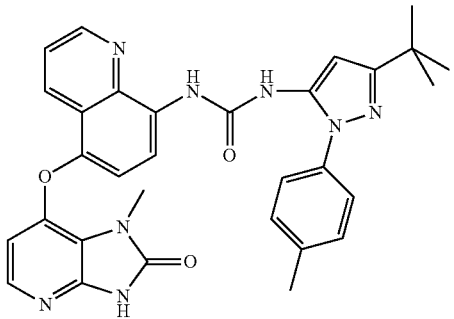 [SMILES: Cc1ccc(-n2nc(C(C)(C)C)cc2NC(=O)Nc2ccc(Oc3ccnc4[nH]c(=O)n(C)c34)c3cccnc23)cc1]

To 40 mg (0.13 mmol) of 4-(8-amino-quinolinyl-5-oxy)-pyridin-5-N-methyl,6-imidazolone, 32, dissolved in 6 mL of THF (dry), were added under stirring and inert atmosphere 1.0 mL (0.18 mmol) of a solution of 1N-p-tolyl-3-t-butyl-pyrazol-5-yl isocyanate in DCM. The reaction mixture was stirred at 40° C. for 18 hours. The solvent was evaporated under vacuum, the residue triturated with Et$_2$O and filtered. 55 mg (yield, 75%) of the title compound were obtained. $^1$H NMR (500 MHz, DMSO-d$_6$) δ: 1.29 (s, 9H, t-Bu), 2.37 (s, 1H, C—CH$_3$), 3.54 (s, 3H, N—CH$_3$), 6.30 (d, 1H, H$_{Pyr}$, J=5.9 Hz), 6.41 (s, 1H, H$_{Pyrazol}$), 7.34-7.70 (m, 6H, H$_{Pyr}$+H$_{Arom}$), 7.73 (d, 1H, H$_{Arom}$), 8.52-8.54 (2×d, 2H, H$_{Arom}$), 8.95 (d, 1H, J=8.6 Hz, H$_{Arom}$), 9.51 (s, 1H, NH$_{urea}$), 9.95 (s, 1H, NH$_{urea}$), 11.64 (s, 1H, NH); LC-MS, t$_R$=5.39 min, m/z: 562.2 (M)$^+$, calcd for C$_{31}$H$_{30}$N$_8$O$_3$; HRMS: (M+H)$^+$ calcd for C$_{31}$H$_{31}$N$_8$O$_3$, 563.2513. Found: 563.2510.

Synthesis 25

4-[(5-Oxy-quinolinyl-8-amino)carbonyl-amino-(1-N-phenyl-3-t-butyl-pyrazol-5-yl)]-pyridin-5-N-methyl,6-imidazolone (AA-012)

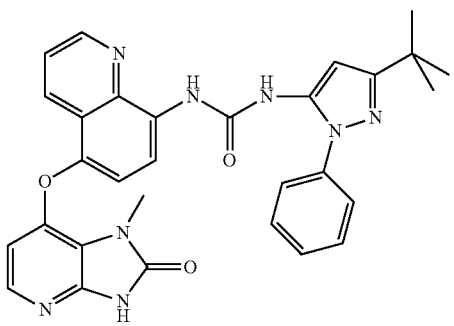 [SMILES: Cn1c(=O)[nH]c2nccc(Oc3ccc(NC(=O)Nc4cc(C(C)(C)C)nn4-c4ccccc4)c4ncccc34)c21]

To 40 mg (0.13 mmol) of 4-(8-amino-quinolinyl-5-oxy)-pyridin-5-N-methyl,6-imidazolone, 32, dissolved in 6 mL of THF (dry), were added under stirring and inert atmosphere 1.0 mL (0.18 mmol) of a solution of 1N-phenyl-3-t-butyl-pyrazol-5-yl isocyanate in DCM. The reaction mixture was stirred at 40° C. for 18 hours. The solvent was evaporated under vacuum, the residue triturated with Et$_2$O and filtered. 55 mg (yield, 75%) of the title compound were obtained. $^1$H NMR (500 MHz, DMSO-d$_6$) δ: 1.30 (s, 9H, t-Bu), 3.54 (s, 3H, N—CH$_3$), 6.31 (d, 1H, H$_{Pyr}$, J=5.9 Hz), 6.43 (s, $^1$H, H$_{Pyrazol}$), 7.34-7.70 (m, 7H, H$_{Pyr}$+H$_{Arom}$), 7.73 (d, 1H, H$_{Arom}$), 8.52-8.54 (2×d, 2H, H$_{Arom}$), 8.95 (d, 1H, J=8.6 Hz, H$_{Arom}$), 9.58 (s, 1H, NH$_{urea}$), 9.95 (s, 1H, NH$_{urea}$), 11.64 (s, 1H, NH); LC-MS, t$_R$=5.29 min, m/z: 548.2 (M)$^+$, calcd for C$_{30}$H$_{28}$N$_8$O$_3$; HRMS: (M+H)$^+$ calcd for C$_{30}$H$_{29}$N$_8$O$_3$, 549.2357. Found: 549.2353.

Synthesis 26

5-[(8-Amino-quinolinyl-5-oxy)carbonylamino-3-(2-fluoro-5-trifluoromethyl-phenyl)]-Pyridin-[2,3]-N-methylimidazol-2-one (AA-013)

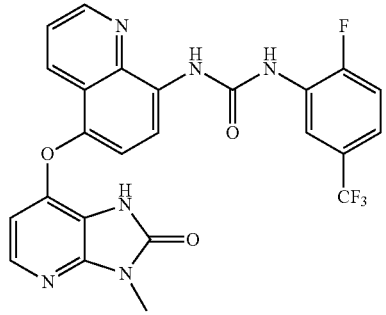 [SMILES: Cn1c(=O)[nH]c2c(Oc3ccc(NC(=O)Nc4cc(C(F)(F)F)ccc4F)c4ncccc34)ccnc21]

Using the same method with 50 mg (0.16 mmol) of 5-(8-amino-quinolinyl-5-oxy)-pyridin-[2,3]-1N-methylpyrazin-2-one, and 43 μL (0.21 mmol) of 2-fluoro-5-trifluoromethyl-phenyl-isocyanate, 56 mg (yield, 68%) of the title compound were obtained. $^1$H NMR (500 MHz, DMSO-d$_6$) δ 3.34 (s, 3H), 6.39 (d, 1H, J=5.9 Hz), 7.37 (d, 1H, J=8.6 Hz), 7.38-7.42 (m, 1H), 7.49 (t, 1H, J=9.4 Hz), 7.66-7.72 (m, 1H), 7.54 (m, 1H), 7.65-7.69 (m, 1H), 7.80 (d, 1H, J=5.9 Hz), 8.39 (dd, 1H, J=10.1 Hz), 8.59 (d, 1H, J=8.6 Hz), 8.68-8.72 (m, 1H), 8.97-9.02 (m, 1H), 9.02-9.04 (m, 1H), 10.10 (s, 1H), 10.33 (s, 1H), 11.56 (s, 1H). LC-MS, t$_R$=2.80 min, m/z: 512.1 M$^+$, calcd for C$_{24}$H$_{16}$F$_4$N$_6$O$_3$; HRMS: (M+H)$^+$ calcd for C$_{24}$H$_{17}$F$_4$N$_6$O$_3$, 513.1293. Found: 513.1299.

Synthesis 27

5-[(8-Amino-quinolinyl-5-oxy)carbonylamino-3-(2-trifluoromethyl-3-chloro-phenyl)]-pyridin-[2,3]-N-methylimidazol-2-one (AA-014)

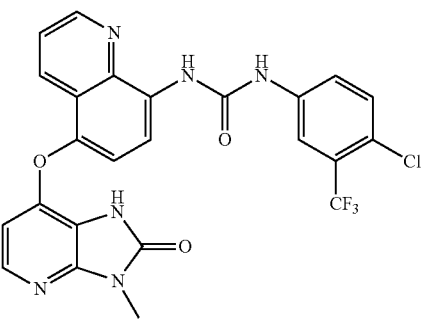 [SMILES: Cn1c(=O)[nH]c2c(Oc3ccc(NC(=O)Nc4ccc(Cl)c(C(F)(F)F)c4)c4ncccc34)ccnc21]

Using the same method with 50 mg (0.16 mmol) of 5-(8-amino-quinolinyl-5-oxy)-pyridin-[2,3]-1N-methylpyrazin-2-one, and 47 mg (0.21 mmol) of 2-trifluoromethyl-3-chloro-phenyl-isocyanate, 63 mg (yield, 75%) of the title compound were obtained. $^1$H NMR (500 MHz, DMSO-d$_6$) δ 3.34 (s, 3H), 6.39 (d, 1H, J=5.9 Hz), 7.37 (d, 1H, J=8.6 Hz), 7.59-7.72 (m, 3H), 7.80 (d, 1H, J=5.9 Hz), 8.17 (d, 1H, J=2.5 Hz), 8.40 (dd, 1H, J=10.1 Hz), 8.56 (d, 1H, J=8.6 Hz), 9.00-9.04 (m, 1H), 9.76 (s, 1H), 10.34 (s, 1H), 11.56 (s, 1H). LC-MS, t$_R$=2.98 min, m/z: 528.1 M$^+$, calcd for C$_{24}$H$_{16}$ClF$_3$N$_6$O$_3$; HRMS: (M+H)$^+$ calcd for C$_{24}$H$_{17}$ClF$_3$N$_6$O$_3$, 529.0997. Found: 529.1009.

Synthesis 28

5-[(8-Amino-quinolinyl-5-oxy)carbonylamino-(2-fluoro-5-trifloromethylphenyl)]-pyridin-[2,3]-3-methylpyrazin-2-one (BB-001)

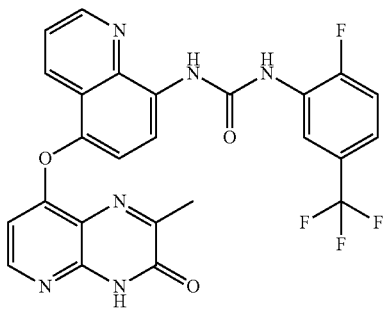 [SMILES: Cc1nc2c(Oc3ccc(NC(=O)Nc4cc(C(F)(F)F)ccc4F)c4ncccc34)ccnc2[nH]c1=O]

Method A: To 40 mg (0.13 mmol) of 5-(8-amino-quinolinyl-5-oxy)-pyridin-[2,3]-3-methylpyrazin-2-one (13), dissolved in 5 mL of DMSO, were added under stirring and inert atmosphere 29 µL (0.20 mmol) of 2-fluoro-3-trifluoromethyl-phenyl isocyanate. The reaction mixture was stirred at room temperature for 18 hours. 15 mL AcOEt were added to the reaction mixture. The solution washed with brine (2×20 mL), the organic layer dried (MgSO$_4$) and evaporated under vacuum. The solid residue thus obtained was triturated with Et$_2$O and filtered. 53 mg (yield, 77%) of the title compound were obtained. $^1$H NMR (500 MHz, DMSO-d$_6$) δ 2.47 (s, 3H), 6.42 (d, 1H, J=5.7 Hz), 7.48 (d, 1H, J=8.6 Hz), 7.48-7.53 (m, 2H), 7.65-7.68 (m, 1H), 8.20 (d, 1H, J=5.7 Hz), 8.28 (dd, 1H, J=1.6 Hz, J$_o$=8.5 Hz), 8.64 (d, 1H, J=8.6 Hz), 9.03-9.05 (m, 1H), 10.13 (s, 1H), 10.38 (s, 1H), 12.79 (s, 1H). LC-MS, t$_R$=2.83 min, m/z: 525.2 (M+H)$^+$, calcd for C$_{25}$H$_{16}$F$_4$N$_6$O$_3$; HRMS: (M+H)$^+$ calcd for C$_{25}$H$_{16}$F$_4$N$_6$O$_3$, 525.1293. Found: 525.1295.

Synthesis 29

5-[(8-Amino-quinolinyl-5-oxy)carbonylamino-3-(2-trifluoromethyl-3-chloro-phenyl)]-pyridin-[2,3]-N-methylimidazol-2-one (AA-015)

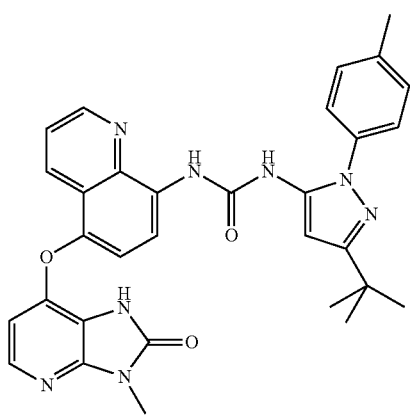 [SMILES: Cc1ccc(-n2nc(C(C)(C)C)cc2NC(=O)Nc2ccc(Oc3ccnc4c3[nH]c(=O)n4C)c3cccnc23)cc1]

Using the same method with 50 mg (0.16 mmol) of 5-(8-amino-quinolinyl-5-oxy)-pyridin-[2,3]-1N-methylpyrazin-2-one, and 0.21 mmol of 1-N-p-tolyl-3-t-butyl-imidazol-5-yl-isocyanate, 68 mg (yield, 76%) of the title compound were obtained. $^1$H NMR (500 MHz, DMSO-d$_6$) δ 1.29 (s, 9H), 2.38 (s, 3H), 3.33 (s, 3H), 6.36 (d, 1H, J=5.9 Hz), 6.40 (s, 1H), 7.31-7.35 (m, 3H), 7.41 (d, 2H, J=8.4 Hz), 7.63-7.68 (m, 1H), 7.79 (d, 1H, J=5.9 Hz), 8.36 (dd, 1H, J=10.1 Hz), 8.53 (d, 1H, J=8.6 Hz), 8.93-8.96 (m, 1H), 9.52 (s, 1H), 9.95 (s, 1H), 11.55 (s, 1H). LC-MS, t$_R$=2.76 min, m/z: 562.2 M$^+$, calcd for C$_{31}$H$_{30}$N$_8$O$_3$; HRMS: (M+H)$^+$ calcd for C$_{31}$H$_{31}$N$_8$O$_3$, 563.2527. Found: 563.2513.

Synthesis 30

5-[(8-Amino-quinolinyl-5-oxy)carbonylamino-5-(2-fluoro-5-trifluoromethyl-phenyl)]-pyridin-[2,3] pyrazin-3-one (BB-004)

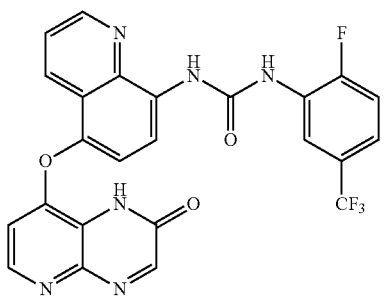 [SMILES: O=C(Nc1cc(C(F)(F)F)ccc1F)Nc1ccc(Oc2ccnc3ncc(=O)[nH]c23)c2cccnc12]

To 30 mg (0.13 mmol) of 5-(8-amino-quinolinyl-5-oxy)-pyridin-[2,3]-pyrazin-3-one, dissolved in 5 mL DMSO, 27 µL (0.18 mmol) of 2-fluoro-5-trifluoromethyl-phenyl-isocyanate, were added and the solution stirred for 18 hours at room temperature. The reaction mixture was diluted with 20 mL AcOEt, washed with 20 mL citric acid solution, then with 20 mL NaHCO$_3$ solution and finally with brine (2×20 mL). The organic layer was dried (MgSO$_4$), and evaporated to dryness to give 27 mg (yield, 41%) of the title compound. $^1$H NMR (500 MHz, DMSO-d$_6$) δ 6.79 (d, 1H, J=5.4 Hz), 7.40-7.45 (m, 1H), 7.48-7.55 (m, 2H), 7.65-7.71 (m, 1H), 8.28 (d, 1H, J=5.3 Hz), 8.41 (dd, 1H, J=8.5 Hz), 8.46 (s, 1H), 8.64 (d, 1H, J=8.6 Hz), 8.71 (d, 1H, J=7.3 Hz), 9.02-9.05 (m, 1H), 10.13 (s, 1H), 10.38 (s, 1H), 12.76 (s, 1H). LC-MS, t$_R$=2.65 min, m/z: 511.1 (M+H)$^+$, calcd for C$_{24}$H$_{14}$F$_4$N$_6$O$_3$.

Synthesis 31

5-[(8-Amino-quinolinyl-5-oxy)carbonylamino-5-(2-fluoro-5-trifluoromethyl-phenyl)]-pyridin-[2,3] pyrazin-2-one (BB-005)

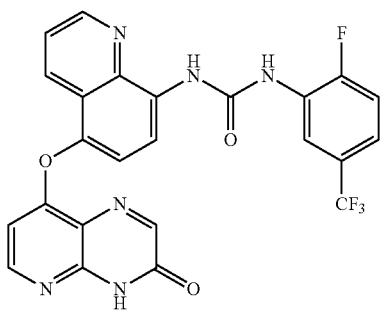 [SMILES: O=C(Nc1cc(C(F)(F)F)ccc1F)Nc1ccc(Oc2ccnc3[nH]c(=O)cnc23)c2cccnc12]

To 30 mg (0.13 mmol) of 5-(8-amino-quinolinyl-5-oxy)-pyridin-[2,3]-pyrazin-2-one, dissolved in 5 mL DMSO, 27 μL (0.18 mmol) of 2-fluoro-5-trifluoromethyl-phenyl-isocyanate, were added and the solution stirred for 18 hours at room temperature. The reaction mixture was diluted with 20 mL AcOEt, washed with 20 mL citric acid solution, then with 20 mL NaHCO$_3$ solution and finally with brine (2×20 mL). The organic layer was dried (MgSO$_4$), and evaporated to dryness to give 25 mg (yield, 38%) of the title compound. $^1$H NMR (500 MHz, DMSO-d$_6$) δ 6.49 (d, 1H, J=5.7 Hz), 7.46-7.50 (m, 1H), 7.55-7.64 (m, 2H), 7.69-7.71 (m, 1H), 8.21 (s, 1H), 8.28-8.32 (m, 2H), 8.64 (d, 1H, J=8.6 Hz), 8.70 (dd, 1H, J=7.2 Hz), 9.03-9.06 (m, 1H), 10.13 (s, 1H), 10.38 (s, 1H), 12.94 (s, 1H). LC-MS, t$_R$=2.73 min, m/z: 511.1 (M+H)$^+$, calcd for C$_{24}$H$_{14}$F$_4$N$_6$O$_3$; HRMS: (M+H)$^+$ calcd for C$_{24}$H$_{15}$F$_4$N$_6$O$_3$, 511.1136. Found 511.1139.

Synthesis 32

5-[(8-Amino-quinolinyl-5-oxy)carbonylamino-5-(1-N-p-tolyl-3-t-butyl-imidazolyl)]-pyridin-[2,3]-3-methylpyrazin-2-one (BB-002)

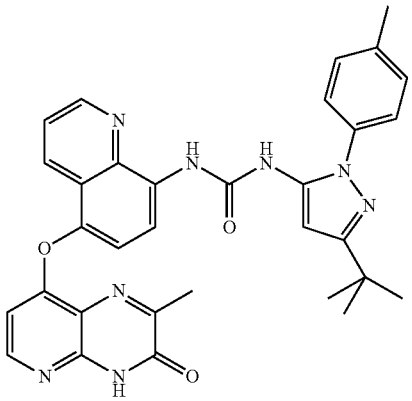 [SMILES: Cc1ccc(-n2nc(C(C)(C)C)cc2NC(=O)Nc2ccc(Oc3ccnc4[nH]c(=O)c(C)nc34)c3cccnc23)cc1]

Using a method analogous to Method A, with 40 mg (0.13 mmol) of 5-(8-amino-quinolinyl-5-oxy)-pyridin-[2,3]-3-methylpyrazin-2-one (13), and 0.2 mmol of 1-p-tolyl-3-t-butyl-imidazolyl-5-isocyanate, 63 mg (yield, 84%) of the title compound were obtained. $^1$H NMR (500 MHz, DMSO-d$_6$) δ 1.30 (s, 9H), 2.38 (s, 3H), 2.47 (s, 3H), 6.40 (d, 1H, J=5.7 Hz), 6.41 (s, 1H), 7.34 (d, 2H, J=8.2 Hz), 7.41-7.45 (m, 3H), 7.62-7.65 (m, 1H), 8.19 (d, 1H, J=5.7 Hz), 8.24 (dd, 1H, J=1.6 Hz, J$_o$=8.5 Hz), 8.58 (d, 1H, J=8.6 Hz), 8.85-8.87 (m, 1H), 9.54 (s, 1H), 9.99 (s, 1H), 12.75 (s, 1H). LC-MS, t$_R$=2.85 min, m/z: 575.2 (M+H)$^+$, calcd for C$_{32}$H$_{30}$N$_8$O$_3$; HRMS: (M+H)$^+$ calcd for C$_{32}$H$_{30}$N$_6$O$_3$, 575.2513. Found: 575.2520.

Synthesis 33

5-[(8-Amino-quinolinyl-5-oxy)carbonylamino-5-(1-N-p-phenyl-3-t-butyl-imidazolyl)]-pyridin-[2,3]-3-methylpyrazin-2-one (BB-003)

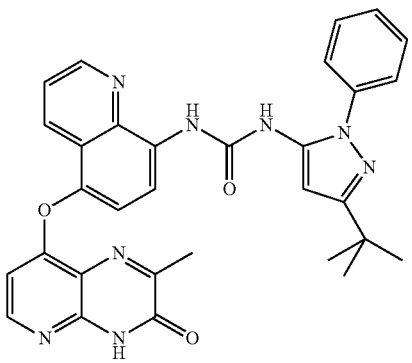 [SMILES: Cc1nc2c(Oc3ccc(NC(=O)Nc4cc(C(C)(C)C)nn4-c4ccccc4)c4ncccc34)ccnc2[nH]c1=O]

Using a method analogous to Method A, with 40 mg (0.13 mmol) of 5-(8-amino-quinolinyl-5-oxy)-pyridin-[2,3]-3-methylpyrazin-2-one (13), and 0.2 mmol of 1-p-tolyl-3-t-butyl-imidazolyl-5-isocyanate, 49 mg (yield, 67%) of the title compound were obtained. $^1$H NMR (500 MHz, DMSO-d$_6$) δ 1.31 (s, 9H), 2.47 (s, 3H), 6.40 (d, 1H, J=5.7 Hz), 6.44 (s, 1H), 7.34 (d, 1H, J=8.6 Hz), 7.54-7.56 (m, 3H), 7.62-7.65 (m, 1H), 8.18 (d, 1H, J=5.7 Hz), 8.27 (dd, 1H, J=1.6 Hz, J$_o$=8.5 Hz), 8.58 (d, 1H, J=8.6 Hz), 8.85-8.87 (m, 1H), 9.61 (s, 1H), 9.99 (s, 1H), 12.78 (s, 1H). LC-MS, t$_R$=2.78 min, m/z: 561.2 (M+H)$^+$, calcd for C$_{31}$H$_{28}$N$_8$O$_3$; HRMS: (M+H)$^+$ calcd for C$_{31}$H$_{28}$N$_8$O$_3$, 561.2357. Found: 561.2356.

Synthesis 34

5-[(8-Amino-quinolinyl-5-oxy)carbonylamino-5-(1-N-p-tolyl-3-t-butyl-imidazolyl)]-pyridin-[2,3]pyrazin-2-one (BB-007)

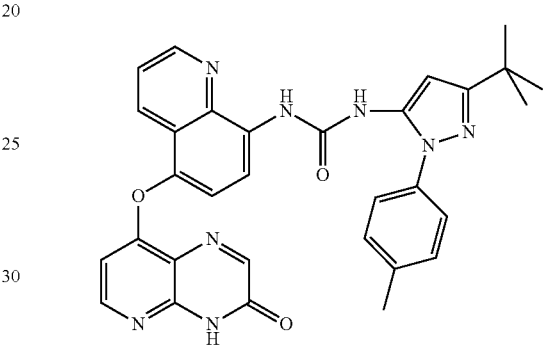

Using the same method with 30 mg (0.10 mmol) of 5-(8-amino-quinolinyl-5-oxy)-pyridin-[2,3]-pyrazin-2-one, and 0.18 mmol of 1-p-tolyl-3-t-butyl-imidazolyl-5-isocyanate, 38 mg (yield, 70%) of the title compound were obtained. $^1$H NMR (500 MHz, DMSO-d$_6$) δ 1.29 (s, 9H), 6.42 (s, 1H), 6.46 (d, 2H, J=8.3 Hz), 6.46 (d, 2H, J=8.3 Hz), 7.42 (d, 2H), 7.47 (d, 1H, J=8.6 Hz), 7.62-7.66 (m, 1H), 8.22-8.29 (m, 2H), 8.58 (d, 1H, J=8.6 Hz), 8.95-9.00 (m, 1H), 9.58 (s, 1H), 10.02 (s, 1H), 12.98 (s, 1H). LC-MS, t$_R$=2.78 min, m/z: 561.2 (M+H)$^+$, calcd for C$_{31}$H$_{28}$N$_8$O$_3$; HRMS: (M+H)$^+$ calcd for C$_{31}$H$_{29}$N$_8$O$_3$, 561.2357. Found: 561.2366.

Synthesis 35

5-[(8-Amino-quinolinyl-5-oxy)carbonylamino-5-(1-N-phenyl-3-t-butyl-imidazolyl)]-pyridin-[2,3]pyrazin-2-one (BB-008)

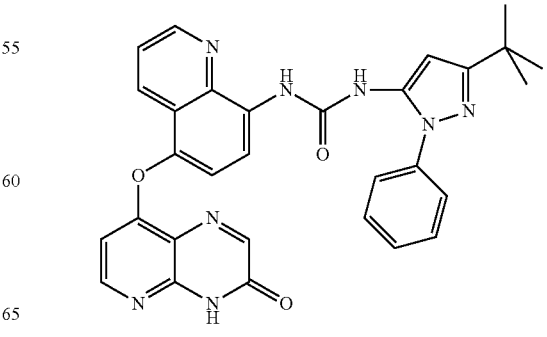

Using the same method with 30 mg (0.10 mmol) of 5-(8-amino-quinolinyl-5-oxy)-pyridin-[2,3]-pyrazin-2-one, and 0.18 mmol of 1-phenyl-3-t-butyl-imidazolyl-5-isocyanate, 35 mg (yield, 64%) of the title compound were obtained. $^1$H NMR (500 MHz, DMSO-$d_6$) δ 1.29 (s, 9H), 6.44 (s, 1H), 6.47 (d, 1H, J=5.7 Hz), 7.38 (t, 1H, J=6.6 Hz), 7.46 (d, 1H, J=8.7 Hz), 7.52-7.58 (m, 4H), 7.61-7.67 (m, 1H), 8.23 (s, 1H), 8.27 (d, 1H, J=5.7 Hz), 8.57 (d, 1H, J=8.6 Hz), 8.95-8.97 (m, 1H), 9.61 (s, 1H), 9.99 (s, 1H), 12.92 (s, 1H). LC-MS, $t_R$=2.70 min, m/z: 546.2 M$^+$, calcd for $C_{30}H_{26}N_8O_3$; HRMS: (M+H)$^+$ calcd for $C_{30}H_{27}N_8O_3$, 547.2201. Found: 547.2201.

Synthesis 36

5-[(8-Amino-quinolinyl-5-oxy)carbonylamino-5-(1-phenyl-3-t-butyl-imidazolyl)]-pyridin-[2,3]1-N-methylimidazol-2-one (AA-016)

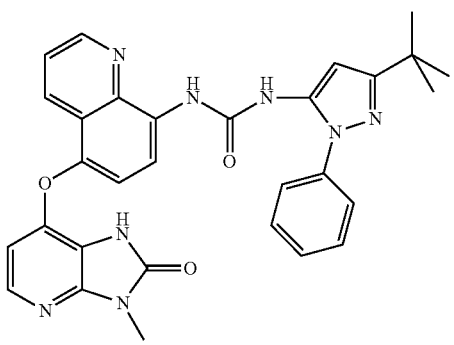 [SMILES: Cn1c(=O)[nH]c2c(Oc3ccc(NC(=O)Nc4cc(C(C)(C)C)nn4-c4ccccc4)c4ncccc34)ccnc21]

Using the same method with 50 mg (0.16 mmol) of 5-(8-amino-quinolinyl-5-oxy)-pyridin-[2,3]-1N-methylpyrazin-2-one, and 0.21 mmol of 1-phenyl-3-t-butyl-imidazolyl-5-isocyanate, 60 mg (yield, 68%) of the title compound were obtained. $^1$H NMR (500 MHz, DMSO-$d_6$) δ 1.30 (s, 9H), 3.34 (s, 3H), 6.36 (d, 1H, J=5.9 Hz), 6.43 (s, 1H), 7.35 (d, 1H, J=8.6 Hz), 7.36-7.42 (m, 1H), 7.50-7.57 (m, 4H), 7.64-7.68 (m, 1H), 7.79 (d, 1H, J=5.9 Hz), 8.36 (dd, 1H, J=10.1 Hz), 8.53 (d, 1H, J=8.6 Hz), 8.94-9.00 (m, 1H), 9.58 (s, 1H), 9.95 (s, 1H), 11.55 (s, 1H). LC-MS, $t_R$=3.20 min, m/z: 549.2 (M+H)$^+$, calcd for $C_{30}H_{29}N_{18}O_3$; HRMS: (M+H)$^+$ calcd for $C_{30}H_{29}N_8O_3$, 549.2357. Found: 549.2356.

Synthesis 37

5-[(8-Amino-quinolinyl-5-oxy)carbonylamino-3-(t-butyl-phenyl)]-pyridin-[2,3]1-N-methylimidazol-2-one (AA-018)

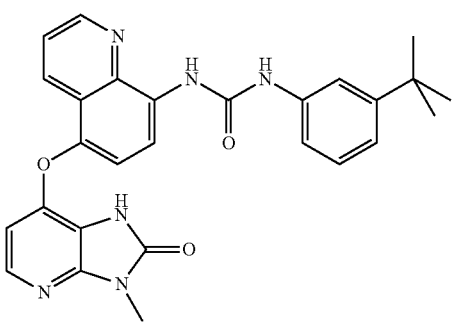 [SMILES: Cn1c(=O)[nH]c2c(Oc3ccc(NC(=O)Nc4cccc(C(C)(C)C)c4)c4ncccc34)ccnc21]

Using the same method with 50 mg (0.16 mmol) of 5-(8-amino-quinolinyl-5-oxy)-pyridin-[2,3]-1N-methylpyrazin-2-one, and 0.21 mmol of 1-t-butyl-phenyl-3-isocyanate, 63 mg (yield, 81%) of the title compound were obtained. $^1$H NMR (500 MHz, DMSO-$d_6$) δ 1.30 (s, 9H), 3.34 (s, 3H), 6.36 (d, 1H, J=5.9 Hz), 7.03 (d, 1H, J=8.7 Hz), 7.23 (t, 1H, J=7.9 Hz), 7.34-7.41 (m, 2H), 7.54 (m, 1H), 7.65-7.69 (m, 1H), 7.79 (d, 1H, J=5.9 Hz), 8.36 (dd, 1H, J=10.1 Hz), 8.58 (d, 1H, J=8.6 Hz), 8.97-9.02 (m, 1H), 9.67 (s, 1H), 9.82 (s, 1H), 11.56 (s, 1H). LC-MS, $t_R$=3.30 min, m/z: 487.2 (M+H)$^+$, calcd for $C_{27}H_{27}N_6O_3$; HRMS: (M+H)$^+$ calcd for $C_{27}H_{27}N_6O_3$, 483.2139. Found: 483.2143.

Synthesis 38

5-[(8-Amino-quinolinyl-5-oxy)carbonylamino-5-(1-phenyl-3-t-butyl-imidazolyl)]-pyridin-[2,3]pyrazin-3-one (BB-010)

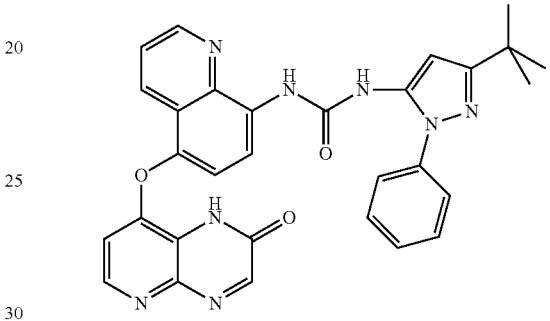

To 30 mg (0.13 mmol) of 5-(8-amino-quinolinyl-5-oxy)-pyridin-[2,3]-pyrazin-3-one, dissolved in 5 mL DMSO, 55 mg (0.20 mmol) of 1-phenyl-3-t-butyl-imidazolyl-5-isocyanate, were added and the solution stirred for 18 hours at room temperature. The reaction mixture was diluted with 20 mL AcOEt, washed with 20 mL citric acid solution, then with 20 mL NaHCO$_3$ solution and finally with brine (2×20 mL). The organic layer was dried (MgSO$_4$), and evaporated to dryness to give 33 mg (yield, 46%) of the title compound. $^1$H NMR (500 MHz, DMSO-$d_6$) δ 1.31 (s, 9H), 6.43 (s, 1H), 6.77 (d, 1H, J=5.3 Hz), 7.49 (d, 2H, J=8.6 Hz), 7.51-7.57 (m, 3H), 7.63-7.68 (m, 1H), 8.28 (d, 1H, J=5.3 Hz), 8.38 (dd, 1H, J=8.5 Hz), 8.58 (d, 1H, J=8.6

Hz), 8.95-8.99 (m, 1H), 9.61 (s, 1H), 9.99 (s, 1H), 12.75 (s, 1H). LC-MS, $t_R$=2.78 min, m/z: 546.2 (M+H)$^+$, calcd for $C_{30}H_{26}N_8O_3$; HRMS: (M+H)$^+$ calcd for $C_{30}H_{27}N_6O_3$ 547.2200. Found: 547.2197.

Synthesis 39

5-[(8-Amino-quinolinyl-5-oxy)carbonylamino-5-(1-methyl-3-t-butyl-imidazolyl)]-pyridin-[2,3]-3-methylpyrazin-2-one (BB-006)

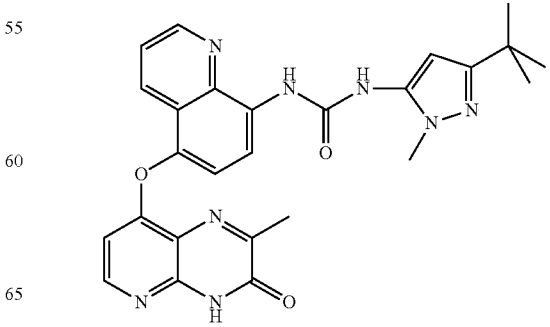

To 40 mg (0.13 mmol) of 5-(8-amino-quinolinyl-5-oxy)-pyridin-[2,3]-3-methylpyrazin-2-one, dissolved in 5 mL DMSO, 55 mg (0.2 mmol) of 1-methyl-3-t-butyl-imidazolyl-5-N-phenyl carbamate, were added and the solution stirred for 18 hours at room temperature. The reaction mixture was diluted with 20 mL AcOEt, washed with 20 mL citric acid solution, then with 20 mL NaHCO$_3$ solution and finally with brine (2×20 mL). The organic layer was dried (MgSO$_4$) and evaporated to dryness to give 39 mg (yield, 67%) of the title compound. After chromatography on Isolute column (Flash Si II, 10 g; eluent: AcOEt:EtOH 4:1) 17 mg were obtained. $^1$H NMR (500 MHz, DMSO-d$_6$) δ 1.23 (s, 9H), 2.47 (s, 3H), 3.68 (s, 3H), 6.16 (s, 1H), 6.41 (d, 1H, J=5.6 Hz), 7.47 (d, 1H, J=8.6 Hz), 7.64-7.70 (m, 1H), 8.19 (d, 1H, J=5.6 Hz), 8.27 (dd, 1H, J=9.9 Hz), 8.60 (d, 1H, J=8.6 Hz), 9.00-9.04 (m, 1H), 9.65 (s, 1H), 9.97 (s, 1H), 12.80 (s, 1H). LC-MS, t$_R$=2.60 min, m/z: 499.2 (M+H)$^+$, calcd for C$_{26}$H$_{27}$N$_6$O$_3$; HRMS: (M+H)$^+$ calcd for C$_{26}$H$_{27}$N$_8$O$_3$, 499.2201. Found: 499.2200.

Synthesis 40

5-[(8-Amino-quinolinyl-5-oxy)carbonylamino-5-(1-methyl-3-t-butyl-imidazolyl)]-pyridin-[2,3]1-N-methylimidazol-2-one (AA-017)

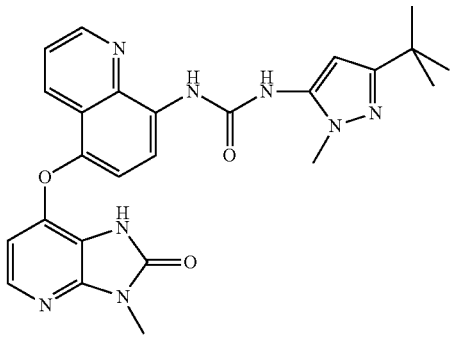 [SMILES: Cn1nc(C(C)(C)C)cc1NC(=O)Nc1ccc(Oc2ccnc3c2[nH]c(=O)n3C)c2cccnc12]

To 50 mg (0.16 mmol) of 5-(8-amino-quinolinyl-5-oxy)-pyridin-[2,3]-1 N-methylimidazol-2-one, dissolved in 6 mL DMSO, 55 mg (0.2 mmol) of 1-methyl-3-t-butyl-imidazolyl-5-N-phenyl carbamate, were added and the solution stirred for 18 hours at room temperature. The reaction mixture was diluted with 20 mL AcOEt, washed with 20 mL citric acid solution, then with 20 mL NaHCO$_3$ solution and finally with brine (2×20 mL). The organic layer was dried (MgSO$_4$) and evaporated to dryness to give 40 mg (yield, 54%) of the title compound. $^1$H NMR (500 MHz, DMSO-d$_6$) δ 1.22 (s, 9H), 2.49 (s, 3H), 2.67 (s, 3H), 6.16 (s, 1H), 6.36 (d, 1H, J=5.9 Hz), 7.38 (d, 1H, J=8.6 Hz), 7.67-7.71 (m, 1H), 7.79 (d, 1H, J=5.9 Hz), 8.77 (dd, 1H, J=10.1 Hz), 8.55 (d, 1H, J=8.6 Hz), 8.98-9.02 (m, 1H), 9.67 (s, 1H), 9.96 (s, 1H), 11.61 (s, 1H). LC-MS, t$_R$=2.78 min, m/z: 487.2 (M+H)$^+$, calcd for C$_{25}$H$_{26}$N$_8$O$_2$; HRMS: (M+H)$^+$ calcd for C$_{25}$H$_{26}$N$_8$O$_3$, 487.2201. Found: 487.2192.

Synthesis 41

5-[(8-Amino-quinolinyl-5-oxy)carbonylamino-5-(1-allyl-3-t-butyl-imidazolyl)]-pyridin-[2,3]-3-methylpyrazin-2-one (BB-009)

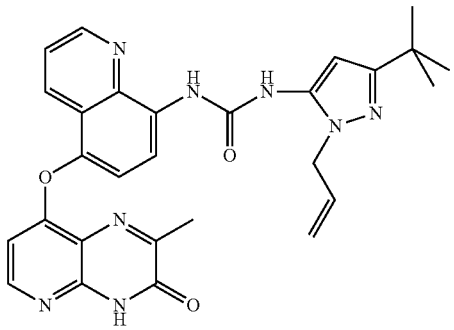 [SMILES: C=CCn1nc(C(C)(C)C)cc1NC(=O)Nc1ccc(Oc2ccnc3[nH]c(=O)c(C)nc23)c2cccnc12]

3-tert-butyl-1-(allyl)-1H-pyrazole-5-carboxylic acid (65.2 mg, 0.313 mmol) was added under stirring and argon to dry triethylamine (0.044 mL, 0.313 mmol) and dry DMF (1.5 mL) to give a colorless solution. The solution was cooled to 0° C., DPPA (0.067 mL, 0.313 mmol) was added at once and the solution was stirred at 0° C. for an additional 30 minutes and then at room temperature for 1 hour. Then, 8-(8-amino-quinolyl-5-oxy)pyrido[2,3-b]-2-methylpyrazin-3(4H)-one (50 mg, 0.157 mmol) was added at once and the solution was heated to 100° C. for 30 minutes. The reaction mixture was allowed to reach room temperature, then 10 mL AcOEt added and the solution washed with (2×10 mL) brine. The organic layer was dried (MgSO$_4$) and concentrated using a rotary evaporator. The solid residue resulted was triturated with Et$_2$O and filtered giving 38 mg (yield, 46.5%) of the title compound. $^1$H NMR (500 MHz, DMSO-d$_6$) δ 1.24 (s, 9H), 4.67 (d, 2H, J=4.9 Hz), 4.94 (d, 1H, J=17.1 Hz), 5.13 (d, 1H, J=10.3 Hz), 5.92-6.04 (m, 1H), 6.22 (s, 1H), 6.41 (d, 1H, J=5.7 Hz), 7.46 (d, 1H, J=8.6 Hz), 7.62-7.71 (m, 1H), 8.19 (d, 1H, J=5.7 Hz), 8.27 (d, 1H, J=7.1 Hz), 8.60 (d, 1H, J=8.6 Hz), 8.95-9.02 (m, 1H), 9.57 (s, 1H), 9.96 (s, 1H), 12.80 (s, 1H). LC-MS, t$_R$=2.70 min, m/z: 524.2 M$^+$, calcd for C$_{28}$H$_{28}$N$_8$O$_3$; HRMS: (M+H)$^+$ calcd for C$_{31}$H$_{29}$N$_8$O$_3$, 525.2357. Found: 525.2356.

Synthesis 42

5-[(8-Amino-quinolinyl-5-oxy)carbonylamino-5-(1-propargyl-3-t-butyl-imidazolyl)]-pyridin-[2,3]-3-methylpyrazin-2-one (BB-011)

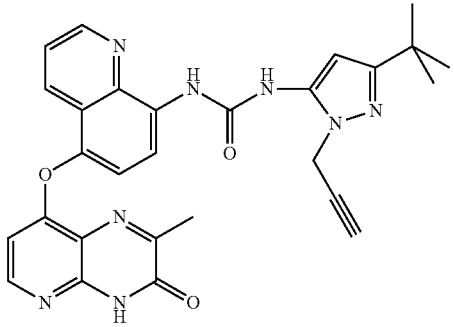 [SMILES: C#CCn1nc(C(C)(C)C)cc1NC(=O)Nc1ccc(Oc2ccnc3[nH]c(=O)c(C)nc23)c2cccnc12]

3-tert-butyl-1-(propargyl)-1H-pyrazole-5-carboxylic acid (64.6 mg, 0.313 mmol) was added under stirring and argon to dry triethylamine (0.044 mL, 0.313 mmol) and dry DMF (1 mL) to give a colorless solution. The solution was cooled to 0° C., DPPA (0.067 mL, 0.313 mmol) was added at once and the solution was stirred at 0° C. for an additional 30 minutes and then at room temperature for 1 hour. Then, 8-(8-amino-quinolyl-5-oxy)pyrido[2,3-b]-2-methylpyrazin-3(4H)-one (50 mg, 0.157 mmol) was added at once and the solution was heated to 100° C. for 30 minutes. The reaction mixture was allowed to reach room temperature, then 10 mL AcOEt added and the solution washed with (2×10 mL) brine. The organic layer was dried (MgSO$_4$) and concentrated using a rotary evaporator. The solid residue resulted was triturated with Et$_2$O and filtered giving 58 mg (71%) of the desired compound. $^1$H NMR (500 MHz, DMSO-d$_6$) δ 1.24 (s, 9H), 2.47 (s, 3H), 4.90 (s, 2H), 6.23 (s, 1H), 6.41 (d, 1H, J=5.7 Hz), 7.47 (d, 1H, J=8.6 Hz), 7.65-7.71 (m, 1H), 7.95 (s, 1H), 8.19 (d, 1H, J=5.7 Hz), 8.28 (d, 1H, J=8.5 Hz), 8.61 (d, 1H, J=8.5 Hz), 8.90-9.07 (m, 1H), 9.78 (s, 1H), 9.99 (s, 1H), 12.80 (s, 1H). LC-MS, t$_R$=2.59 min, m/z: 522.2 M$^+$, calcd for C$_{28}$H$_{27}$N$_8$O$_3$; HRMS: (M+H)$^+$ calcd for C$_{28}$H$_{26}$N$_8$O$_3$, 523.2201. Found: 523.2200.

Synthesis 43

5-[(8-amino-quinolinyl-5-oxy)carbonylamino-5-(1-propargyl-3-t-butyl-imidazolyl)]-pyridin-[2,3]pyrazin-2-one (BB-012)

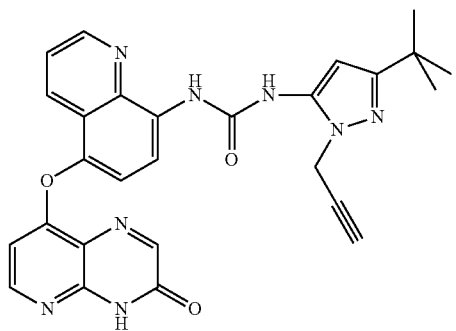 [SMILES: C#CCn1nc(C(C)(C)C)cc1NC(=O)Nc1ccc(Oc2ccnc3[nH]c(=O)cnc23)c2cccnc12]

Using the same method as for BB-009, 3-tert-butyl-1-(propargyl)-1H-pyrazole-5-carboxylic acid (135 mg, 0.655 mmol), dry triethylamine (0.091 mL, 0.655 mmol) and dry DMF (2.5 mL) were reacted with DPPA (0.141 mL, 0.655 mmol) and then with 4-(8-amino-quinazolyl-5-oxy)pyrido[2,3-b]pyrazin-3(4H)-one (100 mg, 0.328 mmol). After trituration with Et$_2$O, a solid resulted (110 mg) which was purified using preparative HPLC on silica to give the title compound. $^1$H NMR (500 MHz, DMSO-d$_6$) δ 1.24 (s, 9H), 4.89 (s, 2H), 6.24 (s, 1H), 6.48 (d, 1H, J=5.7 Hz), 7.49 (d, 1H, J=8.6 Hz), 7.65-7.71 (m, 1H), 8.24-8.30 (m, 3H), 8.61 (d, 1H, J=8.6 Hz), 9.01-9.04 (m, 1H), 9.82 (s, 1H), 10.02 (s, 1H), 12.99 (s, 1H). LC-MS, t$_R$=2.58 min, m/z: 509.2 (M+H)$^+$, calcd for C$_{27}$H$_{24}$N$_8$O$_3$; HRMS: (M+H)$^+$ calcd for C$_{27}$H$_{24}$N$_8$O$_3$, 509.2044. Found: 509.2032.

Synthesis 44

5-[(8-amino-quinolinyl-5-oxy)carbonylamino-5-(1-allyl-3-t-butyl-imidazolyl)]-pyridin-[2,3]pyrazin-2-one (BB-013)

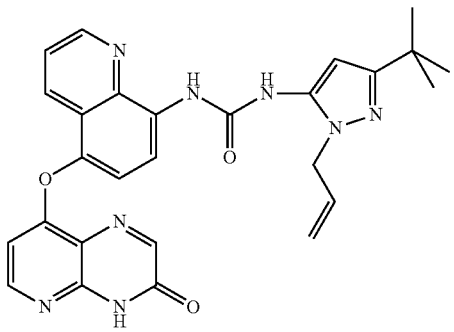 [SMILES: C=CCn1nc(C(C)(C)C)cc1NC(=O)Nc1ccc(Oc2ccnc3[nH]c(=O)cnc23)c2cccnc12]

3-tert-butyl-1-(allyl)-1H-pyrazole-5-carboxylic acid (135 mg, 0.655 mmol), dry triethylamine (0.091 mL, 0.655 mmol) and dry DMF (2.5 mL) were reacted with DPPA (0.141 mL, 0.655 mmol) and then to 4-(8-amino-quinazolyl-5-oxy)pyrido[2,3-b]pyrazin-3(4H)-one (100 mg, 0.328 mmol). After trituration with Et$_2$O a solid resulted (100 mg) which was purified using preparative HPLC on silica to give 18 mg (yield, 22%) of the title compound. $^1$H NMR (500 MHz, DMSO-d$_6$) δ 1.24 (s, 9H), 4.66 (d, 2H, J=4.8 Hz), 4.92 (d, 1H, J=17.1 Hz), 5.13 (d, 1H, J=10.3 Hz), 5.92-6.02 (m, 1H), 6.22 (s, 1H), 6.48 (d, 1H, J=5.7 Hz), 7.48 (d, 1H, J=8.6 Hz), 7.61-7.69 (m, 1H), 8.24-8.29 (m, 3H), 8.61 (d, 1H, J=8.6 Hz), 8.97-9.03 (m, 1H), 9.60 (s, 1H), 9.99 (s, 1H), 12.98 (s, 1H). LC-MS, t$_R$=2.89 min, m/z: 511.1 (M+H)$^+$, calcd for C$_{27}$H$_{26}$N$_8$O$_3$; HRMS: (M+H)$^+$ calcd for C$_{27}$H$_{26}$N$_6$O$_3$, 511.2201. Found: 511.2189.

Biological Methods
Biological Methods—DELFIA Kinase Assay

Compounds were assessed by a kinase assay performed according to the following protocol.

The following reagents were prepared:
DELFIA Kinase Buffer (DKB):

| Reagent | Stock Concentration | Volume per mL (μL) | Volume per 10 mL plate (μL) |
|---|---|---|---|
| 20 mM MOPS pH 7.2 | 0.2M | 100 | 1000 |
| 0.5M EGTA pH 8.0 | 0.5M | 10 | 100 |
| 10 mM MgCl$_2$ | 1M | 10 | 100 |
| 0.1% β-mercaptoethanol | — | 1 | 10 |
| 25 mM β-glycerophosphate | 0.5M | 50 | 500 |
| Water | 100% | 829 | 8290 |

MOPS = 3-[N-Morpholino] propanesulfonic acid (Sigma M3183).
EGTA = Ethylene glycol-bis(2-aminoethylether)-N,N,N',N'-tetraacetic acid (Sigma E3889).

DKB1 (DKB with B-RAF and MEK Protein):
Combine 4950 μL of DKB and 50 μL of 2.5 mg/ml GST-MEK stock (to give 1 mg of MEK per 40 μL). Then add 22.5 μL of B-RAF to give ~0.2 μL of B-RAF per 40 μL.
DKB2 (DKB with MEK Protein):

Combine 4950 µL of DKB and 50 µL of 2.5 mg/ml GST-MEK stock (to give 1 mg of MEK per 40 µL). Use 500 µL of this for the blow out (BO) and the empty vector (EV) control.
ATP:
100 mM stock, dilute to 500 µM to give 100 µM final concentration in assay.
Inhibitors (Test Compounds):
100 mM stock, dilute to 10, 3, 1, 0.3, 0.1, 0.03, 0.01, 0.003, 0.001, 0.0003, 0.0001 mM in DMSO in drug plate, resulting in concentration of 100, 30, 10, 3, 1, 0.3, 0.1, 0.03, 0.01, 0.003, 0.001 µM in the assay.
Primary Antibody:
Phospho-MEK½ CST #9121S diluted 1:1000 in DELFIA assay buffer (AB). Preincubate antibody in the AB for 30 minutes at room temperature prior to use.
Secondary Antibody:
Anti-rabbit-Eur labelled secondary Perkin Elmer #AD0105 diluted 1:1000 in DELFIA assay buffer (AB). Pre-incubate antibody in the AB for 30 minutes at room temperature prior to use. (Primary and secondary antibodies were incubated together.)
Tween:
0.1% Tween 20 in water.
Assay Buffer:
DELFIA assay buffer Perkin Elmer #4002-0010.
Enhancement Solution:
DELFIA enhancement solution Perkin Elmer #4001-0010.
Assay Plates:
96 well glutathione-coated black plate Perbio #15340.
Procedure:
1. Preblock wells with 5% milk in TBS for 1 hour.
2. Wash wells with 3× with 200 µL TBS.
3. Plate out 40 µL of DKB1 for all inhibitors (test compounds), DMSO control, and optionally other control compounds.
4. Plate out 40 µL of DKB2 for BO and EV wells.
5. Add inhibitors (test compounds) at 0.5 µL per well according to desired plate layout.
6. Add 0.5 µL DMSO to vehicle control wells.
7. Add 2 µL of B-RAF to BO and EV wells.
8. Pre-incubate with inhibitors (test compounds) for 10 minutes at room temperature with shaking.
9. Add 10 µL of 500 µM ATP stock, in DKB, to give 100 µM assay concentration.
10. Seal plates with TopSeal and incubate at room temperature with shaking for 45 minutes.
11. Wash plates 3× with 200 µL 0.1% Tween20/Water to terminate reaction.
12. Add 50 µL per well of antibody mix and incubate for 1 hour at room temperature with shaking.
13. Wash plates 3× with 200 µL 0.1% Tween20/Water.
14. Add 100 µL DELFIA enhancement solution per well, cover in foil, and incubate at room temperature for 30 minutes with shaking.
15. Read on Victor using Europium protocol.

Values for the blank (Empty Vector) are subtracted from all values. The DMSO controls are set as 100% activity and assay points (the response) are calculated as a percentage of the DMSO control. Data are plotted using Graphpad Prism software and a non-linear regression line is calculated using a variable slope sigmoidal dose-response equation (Y=Bottom+(Top−Bottom)/(1+10^((LogEC50−X)*HillSlope)) where X is the logarithm of concentration. Y is the response). The IC50 generated by this procedure is the concentration of the drug that produces a percentage control fluorescence value midway between the saturation, and zero-effect plateaus. Three independent assays are usually performed and the mean IC50 is reported.

Biological Methods—Cell Based Phosho-ERK Assay

Compounds were assessed using a cell-based assay which was performed according to the following protocol.
Day 0:
Plate out 16,000 cells/well in 99 µL medium in a 96-well plate.
Day 1:
1. Add 1 µL inhibitor to the cells (total 1 µL solution).
2. Incubate the cells with test compound for 6 hours at 37° C.
3. Aspirate off the solution from all of the wells.
4. Fixate the cells with 100 µL 4% formaldehyde/0.25% Triton X-100 PBS per well.
5. Incubate the plate for 1 hour at 4° C.
6. Aspirate off the fixing solution and add 300 µL TBS per well.
7. Leave the plate overnight at 4° C.
Day 2:
1. Wash the plate 2× with 200 µL PBS per well.
2. Block with 100 µL 5% dried milk in TBS.
3. Incubate the plate for 20 minutes at 37° C.
4. Wash the plate 2× with 0.1% tween/$H_2O$.
5. Add 50 µL of 3 µg/mL primary antibody pERK (Sigma M8159), diluted in 5% milk powder/TBS, to each well.
6. Incubate the plate for 2 hours at 37° C.
7. Wash the plate 3× with 0.1% tween/$H_2O$.
8. Add 50 µL of 0.45 µg/mL secondary Europium-labelled anti-mouse antibody (Perkin Elmer) to each well.
9. Incubate the plate for 1 hour at 37° C.
10. Wash the plate 3× with 0.1% tween/$H_2O$.
11. Add 100 µL enhancement solution (Perkin Elmer) to each well.
12. Leave the plate for approximately 10 minutes at room temperature before gently shaking the plate.
13. Read Europium Time Resolved Fluorescence in Victor2.
14. Wash the plate 2× with 0.1% tween/$H_2O$.
15. Measure the protein concentration with BCA (Sigma) by adding 200 µL of solution per well.
16. Incubate the plate for 30 minutes at 37° C.
17. Read absorbance levels at 570 nm in a plate reader.

Note that Europium counts are normalised for protein levels by dividing counts by absorbance.

Values for the blank (no cells) are subtracted from all values. The DMSO controls are set as 100% activity and assay points (the response) are calculated as a percentage of the DMSO control. Data are plotted using Graphpad Prism software and a non-linear regression line is calculated using a variable slope sigmoidal dose-response equation (Y=Bottom+(Top−Bottom)/(1+10^((LogEC50−X)*HillSlope)) where X is the logarithm of concentration. Y is the response). The IC50 generated by this procedure is the concentration of the drug that produces a percentage control fluorescence value midway between the saturation, and zero-effect plateaus. Three independent assays are usually performed and the mean IC50 is reported.

Biological Methods—SRB Cell Proliferation Assay (SRB $GI_{50}$)

Cultures of WM266.4 melanoma cells are routinely cultured in DMEM/10% foetal bovine serum, at 37° C., in 5% $CO_2$ water saturated atmosphere. Cultures are maintained in exponential growth phase by sub-culturing before having become confluent (3-5 day intervals). Single cell suspensions are prepared by harvesting an 80 cm² tissue culture flask with 5 mL commercial trypsin EDTA. After 5 minutes, the detached cells are mixed with 5 mL fully complemented culture medium and centrifugally pelleted (1000 rpm for 7 minutes). After aspirating the supernatant, the cell pellet is re-suspended in 10 mL fresh medium and the cells fully disaggregated by drawing the whole volume up/down 5 times through a 19-gauge needle. The concentration of the cells is determined using a haemocytometer (1/10 dilution). A suitable volume to give at least a 2-fold excess for the number of tests being conducted, typically 100-200 mL, is prepared by diluting the cell suspension to 10,000/mL, and 100 µL/well dispensed into 96 well plates using a programmable 8-channel peristaltic pump, giving 1000 cells/well, leaving column 12 blank. The plates are returned to the incubator for 24 hours to allow the cells to re-attach.

The compounds being tested are prepared at 20 mM in dimethylsulphoxide. Aliquots (200 µL) are diluted into 20 mL culture medium giving 200 µM, and 10 serial dilutions of 3× performed by transferring 5 mL to 10 mL. Aliquots (100 µL) of each dilution are added to the wells, using an 8-channel pipettor, thus performing a final further 2× dilution, and giving doses ranging from 100 µM to 0.005 µM. Column 11 receives plain culture medium only. Each compound is tested in quadruplicate, each replicate being the average of four wells, and two plates per compound.

After a further 6 days growth, the plates are emptied, and the cells are fixed in 10% trichloroacteic acid for 10 minutes on ice. After thorough rinsing in running tap water, the plates are dried, and stained by adding 50 µL of a solution of 0.1% sulphorhodamine-B in 1% acetic acid, for 10 minutes at room temperature. The stain is poured out and the plates thoroughly rinsed under a stream of 1% acetic acid, thus removing unbound stain, and dried. The bound stain is taken into solution by addition of 150 µL Tris buffer pH 8, followed by 10 minutes on a plate-shaker (approximately 500 rpm). The absorbance at 540 nm in each well (being proportional to the number of cells present) is determined using a plate reader.

After averaging the results in rows A-D and E-H, the blank value (row 12) is subtracted, and results expressed as percentage of the untreated value (row 11). The 10 values so derived (in quadruplicate) are plotted against the logarithm of the drug concentration, and analysed by non-linear regression to a four parameter logistic equation, setting constraints if suggested by inspection. The $GI_{50}$ generated by this procedure is the concentration of the drug that produces a percentage control $A_{540}$ midway between the saturation, and zero-effect plateaus.

Biological Methods—BRAF Cell Based IP Assay

Compounds were assessed using a cell-based assay which was performed according to the following protocol.

WM266.4 cells were seeded at $10^6$ cells per 10 cm dish in DMEM/10% FCS medium. The next day, cells were treated with a range of concentrations of the test compound for 6 hours and then lysed in NP40 buffer.

Lysates were incubated with 20 µL of anti-BRAF antibody (Santa-Cruz F-7) for 1 hour at 4° C. Protein G sepharose beads were washed in PBS three times and 20 µL of beads were added to the lysates and incubated at 4° C. for 2-3 hours. Beads were then collected by centrifugation and washed in 1M KCl buffer, 0.1M KCl buffer, and then salt-free buffer.

Beads were dried and incubated with MEK and ERK GST-fusion proteins in kinase buffer (MKK buffer) for 10 minutes at 30° C. The reaction was stopped with 20 µL of kill buffer. Beads were centrifuged and the supernatant (25 µL) was removed to a fresh tube.

The final reaction was started by the addition of 5 µL of each supernatant to 25 µL of A/MBP buffer for 10 minutes at 30° C. The reaction was terminated by spotting 20 µL onto P81 paper and immersed in 0.4% orthophosphoric acid.

The incorporation of radio-labelled ATP into the MBP substrate was determined by Cerenkov counting. Values for the blank (no BRAF) were subtracted from all values. The DMSO controls were set as 100% activity and assay points (the response) were calculated as a percentage of the DMSO control. Data were plotted using Graphpad Prism software and a non-linear regression line was calculated using a variable slope sigmoidal dose-response equation (Y=Bottom+ (Top−Bottom)/(1+10^((LogEC50−X)*HillSlope)) where X is the logarithm of concentration and Y is the response). The IC50 generated by this procedure is the concentration of the drug that produces a percentage value midway between the saturation, and zero effect plateaus.

| NP40 Buffer | | |
| --- | --- | --- |
| Final Conc. | Stock | Volume for 10 mL (mL) |
| 50 mM Tris pH 7.5 | 1M | 0.5 |
| 150 mM NaCl | 5M | 0.3 |
| 0.5% NP40 | 10% | 0.5 |
| 5 mM NaF | 0.5M | 0.1 |
| 0.2 mM $Na_3VO_4$ | 20 mM | 0.1 |
| Water | 100% | 8.5 |

* Add EDTA-free mini complete tablet before use

| KCl Wash Buffers | | | | |
| --- | --- | --- | --- | --- |
| | | Final Conc. | | |
| | | 1M KCl (mL) | 0.1M KCl (mL) | KCl-free (mL) |
| Components | Stock | Volume for 20 mL | | |
| 30 mM Tris pH 7.5 | 1M | 0.6 | 0.6 | 0.6 |
| 0.1 mM EDTA | 0.5M | 0.004 | 0.004 | 0.004 |
| 0.1% TX-100 | 10% | 0.2 | 0.2 | 0.2 |
| 0.2 mM $Na_3VO_4$ | 20 mM | 0.2 | 0.2 | 0.2 |
| 5 mM NaF | 0.5M | 0.2 | 0.2 | 0.2 |
| 10% glycerol | 50% | 4 | 4 | — |
| KCl | 2M | 10 | 1 | — |
| 0.3% β-ME | 100% | 0.060 | 0.060 | 0.060 |
| Water | 100% | 4.74 | 13.74 | 18.74 |

| MKK Buffer | | |
| --- | --- | --- |
| Final Conc. | Stock | Volume for 1 mL (mL) |
| 30 mM Tris pH 7.5 | 1M | 30 |
| 0.1 mM EDTA | 0.5M | 0.2 |
| 10 mM MgCL2 | 1M | 10 |
| 0.1% TX-100 | 10% | 10 |
| 5 mM NaF | 0.5M | 10 |
| 0.2 mM $Na_3VO_4$ | 20 mM | 10 |
| 800 mM ATP | 100 mM | 8 |
| 0.3% β-Me | 100% | 3 |
| 6.5 mg/mL GST-MEK | 6.5 mg/mL | 1 |
| 100 mg/mL GST-ERK | 20 mg/mL | 5 |
| Water | 100% | 913 |

| Kill Buffer | | |
|---|---|---|
| Final Conc. | Stock | Volume for 1 mL (mL) |
| 30 mM Tris pH 7.5 | 1M | 30 |
| 6 mM EDTA | 0.5M | 12 |
| 0.1% TX-100 | 10% | 10 |
| 5 mM NaF | 0.5M | 10 |
| 0.2 mM Na$_3$VO$_4$ | 20 mM | 10 |
| 0.3% b-Me | 100% | 3 |
| Water | 100% | 913 |

| A/MBP Buffer | | |
|---|---|---|
| Final Conc. | Stock | Volume for 1 mL (mL) |
| 50 mM Tris pH 7.5 | 1M | 50 |
| 0.1 mM EDTA | 0.5M | 0.2 |
| 10 mM MgCl$_2$ | 1M | 10 |
| 0.1% TX-100 | 10% | 10 |
| 5 mM NaF | 0.5M | 10 |
| 0.2 mM Na$_3$VO$_4$ | 20 mM | 10 |
| 100 µM ATP | 100 mM | 1 |
| 0.3% β-Me | 100% | 3 |
| 1 mg/mL MBP | 36.5 mg/mL | 30 |
| 160 mg/mL BSA | 20 mg/mL | 8 |
| 500 µM $^{32}$P-ATP | 100 mM | 5 |
| Water | 100% | 878 |

Biological Results

The following compounds were tested in the "DELFIA Kinase Assay" described above: AA-001 through AA-018 and BB-001 through BB-013.

The following compounds have an IC50 BRAF of less than or equal to 1.0 µM: AA-001, AA-002, AA-005, AA-007, AA-008, AA-009, AA-010, AA-012, AA-013, AA-014, AA-017, AA-018, BB-001, BB-003, BB-004, BB-005, BB-006, BB-007, BB-008, BB-009, BB-011, BB-012, BB-013.

One compound, compound AA-012, has an IC50 BRAF of 1.0 µM.

The following compounds were tested in the "Cell Based Phospho-ERK Assay" described above: AA-001 through AA-018 and BB-001 through BB-013.

The following compounds have an IC$_{50}$ pERK of less than or equal to 10 µM: AA-005, AA-006, AA-007, AA-008, AA-009, AA-010, AA-011, AA-012, AA-013, AA-014, AA-015, AA-016, AA-017, AA-018, BB-001, BB-002, BB-003, BB-004, BB-005, BB-006, BB-007, BB-008, BB-009, BB-010, BB-011, BB-012, BB-013.

One compound, compound AA-012, has an IC50 ppERK of 0.19 µM.

The following compounds were tested in the "SRB Cell Proliferation Assay" described above: AA-001 through AA-018 and BB-001 through BB-013.

The following compounds have a GI50 SRB of less than or equal to 10 µM: AA-001, AA-005, AA-006, AA-007, AA-008, AA-009, AA-010, AA-011, AA-012, AA-014, AA-015, AA-016, AA-017, AA-018, BB-001, BB-002, BB-003, BB-004, BB-005, BB-006, BB-007, BB-008, BB-009, BB-010, BB-011, BB-012, BB-013.

One compound, compound AA-012, has a GI50 SRB of 0.11 µM.

The following compounds were tested in the "BRAF Cell Based IP Assay" described above: AA-011, AA-012, BB-003, BB-007, BB-008.

The following compounds have an IC50 BRAF IP of less than or equal to 1.0 µM: AA-011, AA-012, BB-003, BB-007, BB-008.

One compound, compound AA-012, has an IC50 BRAF IP of 0.21 µM.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

The invention claimed is:

1. A compound selected from compounds of the following formula and pharmaceutically acceptable salts thereof:

(1)

wherein:
—R$^{Q1}$ is independently —H or —R$^{Q1R}$;

wherein:
—R$^{Q1R}$ is independently:
—R$^1$, —R$^{1X}$, —Cl, —OH, —OW, —OR$^{1X}$, —SH, —SR$^1$, —NH$_2$, —NHR$^1$, —NR$^1_2$, or —NR$^{1N4}$R$^{1NB}$;

wherein:
each —R$^1$ is independently:
saturated aliphatic C$_{1-6}$alkyl, and is unsubstituted or substituted with one or more groups selected from —OH, —OR$^{11}$, —NH$_2$, —NHR$^{11}$, or —NR$^{11}_2$;
saturated C$_{3-6}$cycloalkyl, and is unsubstituted or substituted with one or more groups selected from —OH, —OR$^{11}$, —NH$_2$, —NHR$^{11}$, and —NR$^{11}_2$; or
azetidinyl, pyrrolidinyl, or piperidinyl, and is unsubstituted or substituted with one or more groups selected from —R$^{11}$;

and wherein:
each —R$^{1X}$, if present, is independently saturated aliphatic C$_{1-4}$alkyl substituted with one or more groups selected from —F, —Cl, —Br, and —I;

and wherein:
—NR$^{1N4}$R$^{1NB}$ is independently azetidino, pyrrolidino, piperidino, piperizino, morpholino, azepino, or diazepino, and is optionally substituted with one or more groups selected from —R$^{11}$, —CF$_3$, —F, —OH, —OR$^{11}$, —NH$_2$, —NHR$^{11}$, and —NR$^{11}_2$;

wherein:
each —R$^{11}$ is independently saturated aliphatic C$_{1-4}$alkyl;

and wherein:
—R$^{Q2}$ is independently —H or —R$^{Q2R}$;

wherein:
—R$^{Q2R}$ is independently:
—R$^2$, —R$^{2X}$, —Cl, —OH, —OR$^2$, —OR$^{2X}$, —SH, —SR$^2$, —NH$_2$, —NHR$^2$, —NR$^2_2$, or —NR$^{2N4}$R$^{2NB}$;

wherein:
each —R² is independently:
saturated aliphatic $C_{1-6}$alkyl, and is unsubstituted or substituted with one or more groups selected from —OH, —OR²², NH₂, —NHR²², or NR²²₂;
saturated $C_{3-6}$cycloalkyl, and is unsubstituted or substituted with one or more groups selected from —OH, —OR²², —NH₂, —NHR²², and —NR²²₂; or
azetidinyl, pyrrolidinyl, or piperidinyl, and is unsubstituted or substituted with one or more groups selected from —R²²;
and wherein:
each —R²ˣ, if present, is independently saturated aliphatic $C_{1-4}$alkyl substituted with one or more groups selected from —F, —Cl, —Br, and —I;
and wherein:
—NR²ᴺᴬR²ᴺᴮ is independently azetidino, pyrrolidino, piperidino, piperizino, morpholino, azepino, or diazepino, and is optionally substituted with one or more groups selected from —R²², —CF₃, —F, —OH, —OR²², —NH₂, —NHR²², and —NR²²₂;
wherein:
each —R²² is independently saturated aliphatic $C_{1-4}$alkyl;
and wherein:
—X— is independently —O—;
-M- is independently selected from:

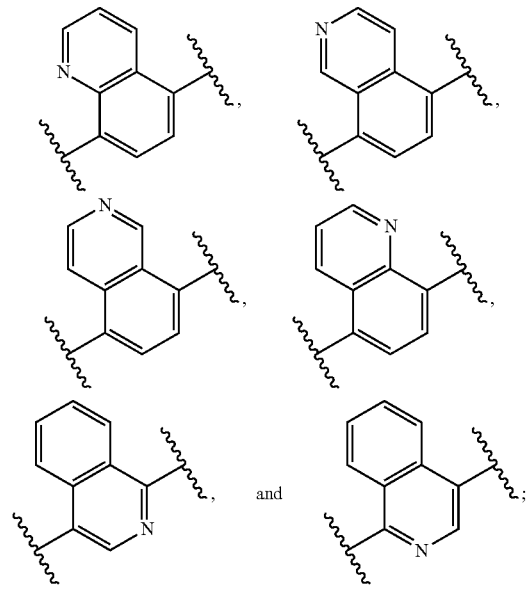

, and ;

J-L- is independently:
J-NR^{N3}—C(=Y)—NR^{N3}—;
wherein:
each —R^{N3} is independently —H or saturated aliphatic $C_{1-4}$alkyl; and
=Y is independently =O; and
-J is independently phenyl or $C_{5-6}$heteroaryl, and is optionally substituted with one or more substituents, —Rᴶ, wherein each —Rᴶ, if present, is independently selected from:
—R^{JA1},
—F, —Cl, —Br, —I,
—CF₃, —OCF₃, —SCF₃,
—OH, -L^{JA}-OH, —O-L^{JA}-OH, NH L^{JA} OH, —NR^{JA1}-L^{JA}-OH,
—OR^{JA1}, -L^{JA}-OR^{JA1}, —O-L^{JA}-OR^{JA1}, —NH-L^{JA}-OR^{JA1}, —NR^{JA1}-L^{JA}-OR^{JA1},
—SH, —SR^{JA1},
—CN,
—NO₂,
—NH₂, —NHR^{JA1}, —NR^{JA1}₂, —NR^{JA2}R^{JA3},
-L^{JA}-NH₂, -L^{JA}-NHR^{JA1}, -L^{JA}-NR^{JA1}₂, -L^{JA}-NR^{JA2}R^{JA3},
—O-L^{JA}-NH₂, —O-L^{JA}-NHR^{JA1}, —O-L^{JA}-NR^{JA1}₂, —O-L^{JA}-NR^{JA2}R^{JA3},
—NH-L^{JA}-NH₂, —NR^{JA1}-L^{JA}-NH₂, —NH-L^{JA}-NHR^{JA1}, —NR^{JA1}-L^{JA}-NHR^{JA1},
—NH-L^{JA}-NR^{JA1}₂, —NR^{JA1}-L^{JA}-NR^{JA1}₂,
—NH-L^{JA}-NR^{JA2}R^{JA3}, —NR^{JA1}-L^{JA}-NR^{JA2}R^{JA3},
—OC(=O)R^{JA1},
—C(=O)OH, —C(=O)OR^{JA1},
—C(=O)R^{JA1},
—C(=O)NH₂, —C(=O)NHR^{JA1}, —C(=O)NR^{JA1}₂, —C(=O)NR^{JA2}R^{JA3},
—NHC(=O)R^{JA1}, —NR^{JA1}(=O)R^{JA1},
—NHC(=O)OR^{JA1}, —NR^{JA1}(=O)OR^{JA1},
—OC(=O)NH₂, —OC(=O)NHR^{JA1}, —OC(=O)NR^{JA1}₂, —OC(=O)NR^{JA2}R^{JA3},
—NHC(=O)NH₂, —NHC(=O)NHR^{JA1},
—NHC(=O)NR^{JA1}₂, —NHC(=O)NR^{JA2}R^{JA3},
—NR^{JA1}(=O)NH₂, —NR^{JA1}(=O)NHR^{JA1},
—NR^{JA1}(=O)NR^{JA1}₂, —NR^{JA1}(=O)NR^{JA2}R^{JA3},
—NHS(=O)₂R^{JA1}, —NR^{JA1}S(=O)₂R^{JA1},
—S(=O)₂NH₂, —S(=O)₂NHR^{JA1}, —S(=O)₂NR^{JA1}₂, —S(=O)₂NR^{JA2}R^{JA3},
—S(=O)R^{JA1}, —S(=O)₂R^{JA1}, —OS(=O)₂R^{JA1},
—S(=O)₂OH, and —S(=O)₂OR^{JA1};
wherein:
each -L^{JA}- is independently saturated aliphatic $C_{1-5}$alkylene;
n each group —NR^{JA2}R^{JA3}, R^{JA2} and R^{JA3} taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
each —R^{JA1} is independently:
—R^{JB1}, —R^{JB2}, —R^{JB3}, —R^{JB4}, —R^{JB5}, —R^{JB6}, —R^{JB7}, —R^{JB8}, -L^{JB}-R^{JB4}, -L^{JB}-R^{JB5}, -L^{JB}-R^{JB6}, -L^{JB}-R^{JB7}, or -L^{JB}-R^{JB8};
each —R^{JB1} is independently saturated aliphatic $C_{1-6}$alkyl;
each —R^{JB2} is independently aliphatic $C_{2-6}$alkenyl;
each —R^{JB3} is independently aliphatic $C_{2-6}$alkynyl;
each —R^{JB4} is independently saturated $C_{3-6}$cycloalkyl;
each —R^{JB5} is independently $C_{3-6}$cycloalkenyl;
each —R^{JB6} is independently non-aromatic $C_{3-8}$heterocyclyl;
each —R^{JB7} is independently $C_{6-10}$carboaryl;
each —R^{JB8} is independently $C_{5-10}$heteroaryl;
each -L^{JB}- is independently saturated aliphatic $C_{1-3}$alkylene;
wherein:
each —R^{JB4}, —R^{JB5}, —R^{JB6}, —R^{JB7} and —R^{JB8} is optionally substituted with one or more substituents —R^{JC1} and/or one or more substituents —R^{JC2},
each —R^{JB1}, —R^{JB2}, —R^{JB3}, and -L^{JB}- is optionally substituted with one or more substituents —R^{JC2}, and wherein:
each —$R^{JC1}$ is independently saturated aliphatic $C_{1-4}$-alkyl, phenyl, or benzyl;
each —$R^{JC2}$ is independently:
—F, —Cl, —Br, —I,
—$CF_3$, —$OCF_3$, —$SCF_3$,
—OH, -$L^{JD}$-OH, —O-$L^{JD}$-OH,
—$OR^{JD1}$, -$L^{JD}$-$OR^{JD1}$, —O-$L^{JD}$-$OR^{JD1}$,
—SH, —$SR^{JD1}$,
—CN,
—$NO_2$,
—$NH_2$, —$NHR^{JD1}$, —$NR^{JD1}{}_2$, —$NR^{JD2}R^{JD3}$,
-$L^{JD}$-$NH_2$, -$L^{JD}$-$NHR^{JD1}$, -$L^{JD}$-$NR^{JD1}{}_2$, -$L^{JD}$-$NR^{JD2}R^{JD3}$,
—C(=O)OH, —C(=O)$OR^{JD1}$,
—C(=O)$NH_2$, —C(=O)$NHR^{JD1}$, —C(=O)$NR^{JD1}{}_2$, or —C(=O)$NR^{JD2}R^{JD3}$;
wherein:
each —$R^{JD1}$ is independently saturated aliphatic $C_{1-4}$alkyl, phenyl, or benzyl;
each -$L^{JD}$- is independently saturated aliphatic $C_{1-5}$alkylene; and
in each group —$NR^{JD2}R^{JD3}$, $R^{JD2}$ and $R^{JD3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

2. A compound according to claim 1, wherein:
—$R^{Q1}$ is independently —$R^{Q1R}$; —$R^{Q1R}$ is independently —OH; and
—$R^{Q1}$ is independently —H;
or (2):
—$R^{Q1}$ is independently —H;
—$R^{Q1}$ is independently —$R^{Q2R}$; and —$R^{Q2R}$ is independently —OH;
or (3):
—$R^{Q1}$ is independently —$R^{Q1R}$; —$R^{Q1R}$ is independently —OH;
—$R^{Q2}$ is independently —$R^{Q2R}$; and —$R^{Q2R}$ is independently -Me;
or (4):
—$R^{Q1}$ is independently —$R^{Q1R}$; —$R^{Q1R}$ is independently -Me;
—$R^{Q2}$ is independently —$R^{Q2R}$; and —$R^{Q2R}$ is independently —OH.

3. A compound according to claim 1, wherein -M- is independently:

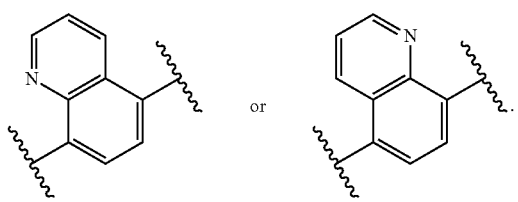 [SMILES: *c1ccc(*)c2ncccc12 ; *c1ccc(*)c2ncccc12]

4. A compound according to claim 2, wherein -M- is independently:

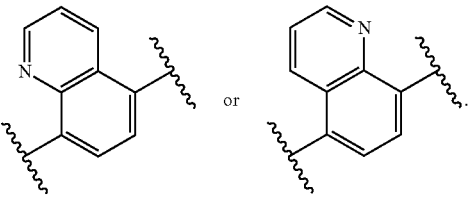 [SMILES: *c1ccc(*)c2ncccc12 ; *c1ccc(*)c2ncccc12]

5. A compound according to claim 3, wherein each —$R^{N3}$ is independently —H or -Me.

6. A compound according to claim 4, wherein the each —$R^{N3}$ is independently —H or -Me.

7. A compound according to claim 3, wherein the group J-L- is independently J-NH—C(=O)—NH—.

8. A compound according to claim 4, wherein the group J-L- is independently J-NH—C(=O)—NH—.

9. A compound according to claim 7, wherein -J is independently phenyl or pyrazolyl, and is optionally substituted with one or more substituents, —$R^J$, wherein each —$R^J$, if present, is independently selected from:
—$R^6$,
—F, —Cl, —Br, —I,
—$CF_3$, —$OCF_3$, —$SCF_3$,
—OH,
—$OR^6$,
—CN,
—$NH_2$, —$NHR^6$ $NR^6{}_2$, $NR^{6NA}R^{6NB}$,
—C(=O)$NH_2$, —C(=O)$NHR^6$, —C(=O)$NR^6{}_2$, —C(=O)$NR^{NA}R^{6NB}$,
—S(=O)$_2NH_2$, —S(=O)$_2NHR^6$, —S(=O)$_2NR^6{}_2$, and —S(=O)$_2NR^{6NA}R^{6NB}$;
wherein:
each —$R^6$ is independently:
saturated aliphatic $C_{1-6}$alkyl, and is unsubstituted or substituted with one or more groups selected from —OH, —$OR^{66}$, —$NH_2$, —$NHR^{66}$, —$NR^{66}{}_2$ or —$NR^{6NA}R^{6NB}$;
saturated $C_{3-6}$cycloalkyl, and is unsubstituted or substituted with one or more groups selected from —OH, —$OR^{66}$, —$NH_2$, —$NHR^{66}$, and —$NR^{66}{}_2$;
azetidinyl, pyrrolidinyl, or piperidinyl, and is unsubstituted or substituted with one or more groups selected from —$R^{66}$; or
phenyl or $C_{5-6}$heteroaryl, and is optionally substituted with one or more substituents independently selected from —F, —Cl, —Br, —I, —$R^{66}$, —OH, —$OR^{66}$, —$CF_3$, —$OCF_3$;
and wherein:
each —$NR^{6NA}R^{6NB}$ is independently azetidino, pyrrolidino, piperidino, piperizino, morpholino, azepino, or diazepino, and is optionally substituted with one or more groups selected from —$R^{66}$, —F, —OH, —$OR^{66}$, —$NH_2$, —$NHR^{66}$, and —$NR^{66}{}_2$;
wherein:
each —$R^{66}$ is independently saturated aliphatic $C_{1-4}$alkyl.

10. A compound according to claim 8, wherein -J is independently phenyl or pyrazolyl, and is optionally substituted with one or more substituents, —$R^J$, wherein each —$R^J$, if present, is independently selected from:
—$R^6$,
—F, —Cl, —Br, —I,
—$CF_3$, —$OCF_3$, —$SCF_3$,
—OH, —OR⁶,
—CN,
—NH₂, —NHR⁶, —NR⁶₂, —NR⁶ᴺᴬR⁶ᴺᴮ,
—C(=O)NH₂, —C(=O)NHR⁶, —C(=O)NR⁶₂, —C(=O)NR⁶ᴺᴬR⁶ᴺᴮ,
—S(=O)₂NH₂, —S(=O)₂NHR⁶, —S(=O)₂NR⁶₂, and —S(=O)₂NR⁶ᴺᴬR⁶ᴺᴮ;

wherein:
each —R⁶ is independently:
saturated aliphatic C₁₋₆alkyl, and is unsubstituted or substituted with one or more groups selected from —OH, —OR⁶⁶, —NH₂, —NHR⁶⁶, NR⁶⁶₂, or —NR⁶ᴺᴬR⁶ᴺᴮ;
saturated C₃₋₆cycloalkyl, and is unsubstituted or substituted with one or more groups selected from —OH, —OR⁶⁶, —NHR⁶⁶, and NR⁶⁶₂;
azetidinyl, pyrrolidinyl, or piperidinyl, and is unsubstituted or substituted with one or more groups selected from —R⁶⁶; or
phenyl or C₅₋₆heteroaryl, and is optionally substituted with one or more substituents independently selected from —F, —Cl, —Br, —I, —R⁶⁶, —OH, —OR⁶⁶, —CF₃, —OCF₃;

and wherein:
each —NR⁶ᴺᴬR⁶ᴺᴮ is independently azetidino, pyrrolidino, piperidino, piperizino, morpholino, azepino, or diazepino, and is optionally substituted with one or more groups selected from —R⁶⁶, —CF₃, —F, —OH, —OR⁶⁶, —NH₂, —NHR⁶⁶, and —NR⁶⁶₂;

wherein:
each —R⁶⁶ is independently saturated aliphatic C₁₋₄alkyl.

11. A compound according to claim 7, wherein -J is independently the following group:

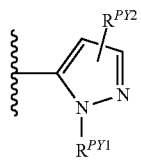

wherein:
—Rᴾʸ¹ is independently phenyl or C₅₋₆heteroaryl, and is optionally substituted with one or more substituents —Rᴾᶻ¹; or
—Rᴾʸ¹ is independently saturated aliphatic C₁₋₆alkyl, aliphatic C₂₋₆alkenyl, aliphatic C₂₋₆alkynyl, saturated C₃₋₇cycloalkyl, or saturated C₃₋₇cycloalkyl-saturated aliphatic C₁₋₆alkyl, and is optionally substituted with one or more substituents —Rᴾᶻ²;
each —Rᴾᶻ¹ is independently selected from —F, —Cl, —Br, —I, —R⁷ᴬ, —OH, —OR⁷ᴬ, and —S(=O)₂R⁷ᴬ;
each —R⁷ᴬ is independently saturated aliphatic C₁₋₆alkyl;
each —Rᴾᶻ² is independently selected from —F, —Cl, —Br, —I, —OH, —OR⁷ᴮ, —NH₂, —NHR⁷ᴮ, and —NR⁷ᴮ₂; and
each —R⁷ᴮ is independently saturated aliphatic C₁₋₆alkyl;
and wherein:
—Rᴾʸ² is independently —F, —Cl, —Br, —I, —R⁸, —OH, —OR⁸, —CF₃, —OCF₃, —SCF₃, or phenyl optionally substituted with one or more substituents —Rᴾᶻ³;

wherein:
each —R⁸ is independently saturated aliphatic C₁₋₆alkyl or saturated C₃₋₆cycloalkyl;
each —Rᴾᶻ³ is independently —F, —Cl, —Br, —I, —Rⱽ, —OH, —ORⱽ, —NH₂, —NHRⱽ, —NRⱽ₂, —NRⱽᴺᴬRⱽᴺᴮ, —CN, —S(=O)₂NH₂, —S(=O)₂NHRⱽ, —S(=O)₂NRⱽ₂, —S(=O)₂NRⱽᴺᴬRⱽᴺᴮ, or —C(=O)NRⱽᴺᴬRⱽᴺᴮ;

wherein:
each —Rⱽ is independently:
saturated aliphatic C₁₋₆alkyl, and is unsubstituted or substituted with one or more groups selected from —OH, —ORᵂ, —NH₂, —NHRᵂ, and —NRᵂ₂;
saturated C₃₋₆cycloalkyl, and is unsubstituted or substituted with one or more groups selected from —OH, —ORᵂ, —NH₂, —NHRᵂ, and —NRᵂ₂; or
azetidinyl, pyrrolidinyl, or piperidinyl, and is unsubstituted or substituted with one or more groups selected from —Rᵂ;
and wherein:
—NRⱽᴺᴬRⱽᴺᴮ is independently azetidino, pyrrolidino, piperidino, piperizino, morpholino, azepino, or diazepino, and is optionally substituted with one or more groups selected from —Rᵂ, —CF₃, —F, —OH, —ORᵂ, —NH₂, —NHRᵂ, and —NRᵂ₂;

wherein:
each —Rᵂ is independently saturated aliphatic C₁₋₄alkyl.

12. A compound according to claim 8, wherein -J is independently the following group:

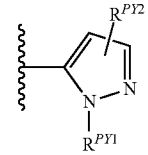

wherein:
—Rᴾʸ¹ is independently phenyl or C₅₋₆heteroaryl, and is optionally substituted with one or more substituents —Rᴾᶻ¹; or
—Rᴾʸ¹ is independently saturated aliphatic C₁₋₆alkyl, aliphatic C₂₋₆alkenyl, aliphatic C₂₋₆alkynyl, saturated C₃₋₇cycloalkyl, or saturated C₃₋₇cycloalkyl-saturated aliphatic C₁₋₆alkyl, and is optionally substituted with one or more substituents —Rᴾᶻ²;
each —Rᴾᶻ¹ is independently selected from —F, —Cl, —Br, —I, —R⁷ᴬ, —OH, —OR⁷ᴬ, and —S(=O)₂R⁷ᴬ;
each —R⁷ᴬ is independently saturated aliphatic C₁₋₆alkyl;
each —Rᴾᶻ² is independently selected from —F, —Cl, —Br, —I, —OH, —OR⁷ᴮ, —NH₂, —NHR⁷ᴮ, and —NR⁷ᴮ₂; and
each —R⁷ᴮ is independently saturated aliphatic C₁₋₆alkyl;
and wherein:
—Rᴾʸ² is independently —F, —Cl, —Br, —I, —R⁸, —OH, —OR⁸, —CF₃, —OCF₃, —SCF₃, or phenyl optionally substituted with one or more substituents —Rᴾᶻ³;

wherein:
each —R⁸ is independently saturated aliphatic C₁₋₆alkyl or saturated C₃₋₆cycloalkyl;

each —R$^{PZ3}$ is independently —F, —Cl, —Br, —I, —Rv, —OH, —ORv, —NH$_2$, —NHR$^V$, —NR$^V_2$, —NR$^{VNA}$R$^{VNB}$, —CN, —S(=O)$_2$NH$_2$, —S(=O)$_2$NHR$^V$, —S(=O)$_2$NR$^V_2$, —S(=O)$_2$NR$^{VNA}$R$^{VNB}$, or —C(=O)NR$^{VNA}$R$^{VNB}$;

wherein:
each —R$^V$ is independently:
saturated aliphatic C$_{1-6}$alkyl, and is unsubstituted or substituted with one or more groups selected from —OH, —OR$^W$, —NH$_2$, —NHR$^W$, and —NR$^W_2$;
saturated C$_{3-6}$cycloalkyl, and is unsubstituted or substituted with one or more groups selected from —OH, —OR$^W$, —NH$_2$, —NHR$^W$, and —NR$^W_2$; or
azetidinyl, pyrrolidinyl, or piperidinyl, and is unsubstituted or substituted with one or more groups selected from —R$^W$;

and wherein:
—NR$^{VNA}$R$^{VNB}$ is independently azetidino, pyrrolidino, piperidino, piperizino, morpholino, azepino, or diazepino, and is optionally substituted with one or more groups selected from —R$^W$, —CF$_3$, —F, —OH, —OR$^W$, —NH$_2$, —NHR$^W$, and —NR$^W_2$;

wherein:
each —R$^W$ is independently saturated aliphatic C$_{1-4}$alkyl.

13. A compound according to claim 7, wherein -J is independently:

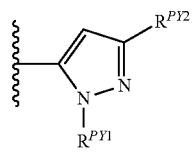

wherein:
—R$^{PY1}$ is independently phenyl, and is optionally substituted with one or more substituents —R$^{PZ1}$, wherein each —R$^{PZ1}$ is independently —F, —Cl, —Br, —I, —R$^{7A}$, —OH, or —OR$^{7A}$, wherein each —R$^{7A}$ is independently saturated aliphatic C$_{1-4}$alkyl; and
—R$^{PY2}$ is independently —R$^8$, wherein —R$^8$ is independently saturated aliphatic C$_{1-6}$alkyl.

14. A compound according to claim 8, wherein -J is independently:

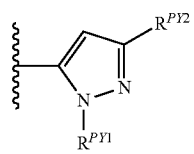

wherein:
—R$^{PY1}$ is independently phenyl, and is optionally substituted with one or more substituents —R$^{PZ1}$, wherein each —R$^{PZ1}$ is independently —F, —Cl, —Br, —I, —R$^{7A}$, —OH, or —OR$^{7A}$, wherein each —R$^{7A}$ is independently saturated aliphatic C$_{1-4}$alkyl; and
—R$^{PY2}$ is independently —R$^8$, wherein —R$^8$ is independently saturated aliphatic C$_{1-6}$alkyl.

15. A compound according to claim 7, wherein -J is independently

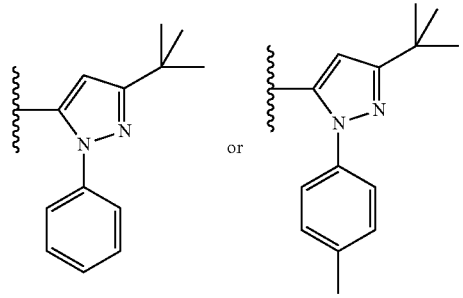

16. A compound according to claim 8, wherein -J is independently

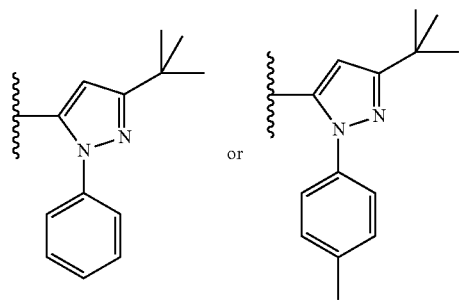

17. A compound according to claim 7, wherein -J is independently:

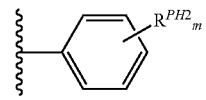

wherein:
m is independently 0, 1, 2, or 3;
each R$^{PH2}$ is independently —F, —Cl, —Br, —I, —R$^9$, —OH, —OR$^9$, —NH$_2$, —NHR$^9$, —NR$^9_2$, —NR$^{9NA}$R$^{9NB}$, —CF$_3$, —OCF$_3$, or —SCF$_3$;

wherein:
each —R$^9$ is independently:
saturated aliphatic C$_{1-6}$alkyl, and is unsubstituted or substituted with one or more groups selected from —OH, —OR$^{99}$, —NH$_2$, —NHR$^{99}$, —NR$^{99}_2$, and —NR$^{9NA}$R$^{9NB}$;
saturated C$_{3-6}$cycloalkyl, and is unsubstituted or substituted with one or more groups selected from —OH, —OR$^{99}$, —NH$_2$, —NHR$^{99}$, and —NR$^{99}_2$;
azetidinyl, pyrrolidinyl, or piperidinyl, and is unsubstituted or substituted with one or more groups selected from —R$^{99}$; or
phenyl or C$_{5-6}$heteroaryl, and is unsubstituted or substituted with one or more groups selected from —F, —Cl, —Br, —I, —R$^{99}$, —CF$_3$, —OH, —OR$^{99}$, —OCF$_3$, —NH$_2$, —NHR$^{99}$, —NR$^{99}_2$, and —NR$^{9NA}$R$^{9NB}$;

and wherein:
—NR$^{9NA}$R$^{9NB}$ is independently azetidino, pyrrolidino, piperidino, piperizino, morpholino, azepino, or diazepino, and is optionally substituted with one or more groups selected from —R$^{99}$, —CF$_3$, —F, —OH, —OR$^{99}$, —NH$_2$, —NHR$^{99}$, and —NR$^{99}{}_2$;

wherein:
each —R$^{99}$ is independently saturated aliphatic C$_{1-4}$alkyl.

18. A compound according to claim 8, wherein -J is independently:

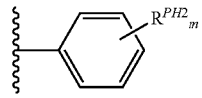

wherein:
m is independently 0, 1, 2, or 3;
each R$^{PH2}$ is independently —F, —Cl, —Br, —I, —R$^9$, —OH, —OR$^9$, —NH$_2$, —NHR$^9$, —NR$^9{}_2$, —NR$^{9NA}$R$^{9NB}$, —CF$_3$, —OCF$_3$, or —SCF$_3$;
wherein:
each —R$^9$ is independently:
saturated aliphatic C$_{1-6}$alkyl, and is unsubstituted or substituted with one or more groups selected from —OH, —OR$^{99}$, —NH$_2$, —NHR$^{99}$, —NR$^{99}{}_2$, and —NR$^{9NA}$R$^{9NB}$;
saturated C$_{3-6}$cycloalkyl, and is unsubstituted or substituted with one or more groups selected from —OH, —OR$^{99}$, —NH$_2$, —NHR$^{99}$, and —NR$^{99}{}_2$;
azetidinyl, pyrrolidinyl, or piperidinyl, and is unsubstituted or substituted with one or more groups selected from —R$^{99}$; or
phenyl or C$_{5-6}$heteroaryl, and is unsubstituted or substituted with one or more groups selected from —F, —Cl, —Br, —I, —R$^{99}$, —CF$_3$, —OH, —OR$^{99}$, —OCF$_3$, —NH$_2$, —NHR$^{99}$, —NR$^{99}{}_2$, and —NR$^{9NA}$R$^{9NB}$;
and wherein:
—NR$^{9NA}$R$^{9NB}$ is independently azetidino, pyrrolidino, piperidino, piperizino, morpholino, azepino, or diazepino, and is optionally substituted with one or more groups selected from —R$^{99}$, —CF$_3$, —F, —OH, —OR$^{99}$, —NH$_2$, —NHR$^{99}$, and —NR$^{99}{}_2$;
wherein:
each —R$^{99}$ is independently saturated aliphatic C$_{1-4}$alkyl.

19. A compound according to claim 17, wherein: m is independently 1 or 2; and each R$^{PH2}$ is independently —F, —Cl, -tBu, —CF$_3$, —OCF$_3$, or —SCF$_3$.

20. A compound according to claim 18, wherein: m is independently 1 or 2; and each R$^{PH2}$ is independently —F, —Cl, -tBu, —CF$_3$, —OCF$_3$, or —SCF$_3$.

21. A compound selected from compounds of the following formula and pharmaceutically acceptable salts thereof:

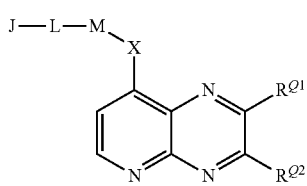

wherein (1):
—R$^{Q1}$ is independently —R$^{Q1R}$; —R$^{Q1R}$ is independently —OH; and
—R$^{Q2}$ is independently —H;
or (2):
—R$^{Q1}$ is independently —H;
—R$^{Q2}$ is independently —R$^{Q2R}$; and —R$^{Q2R}$ is independently —OH;
or (3):
—R$^{Q1}$ is independently —R$^{Q1R}$; —R$^{Q1R}$ is independently —OH;
—R$^{Q2}$ is independently —R$^{Q2R}$; and —R$^{Q2R}$ is independently -Me;
or (4):
—R$^{Q1}$ is independently —R$^{Q1R}$; —R$^{Q1R}$ is independently -Me;
—R$^{Q2}$ is independently —R$^{Q2R}$; and —R$^{Q2R}$ is independently —OH.

and wherein:
—X— is independently —O—;
-M- is independently:

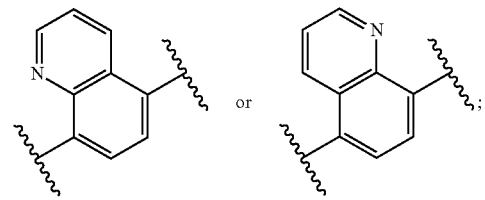 [SMILES: *c1ccc(*)c2ncccc12 ; *c1ccc(*)c2ncccc12]

the group J-L- is independently J-NH—C(=O)—NH—; and
-J is independently:

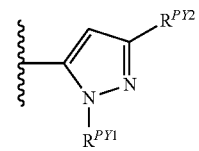

wherein:

—R$^{PY1}$ is independently phenyl, and is optionally substituted with one or more substituents —R$^{PZ1}$, wherein each —R$^{PZ1}$ is independently —F, —Cl, —Br, —I, —R$^{7A}$, —OH, or —OR$^{7A}$, wherein each —R$^{7A}$ is independently saturated aliphatic C$_{1-4}$alkyl; and —R$^{PY2}$ is independently —R$^8$, wherein —R$^8$ is independently saturated aliphatic C$_{1-6}$alkyl.

22. A compound selected from the following compounds, and pharmaceutically acceptable salts thereof:
(BB-001)
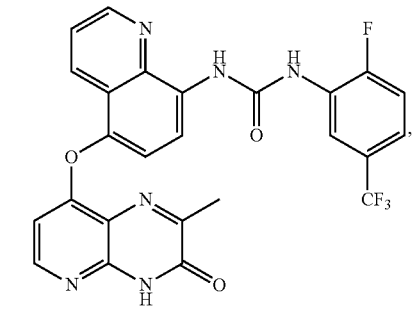
(BB-002)
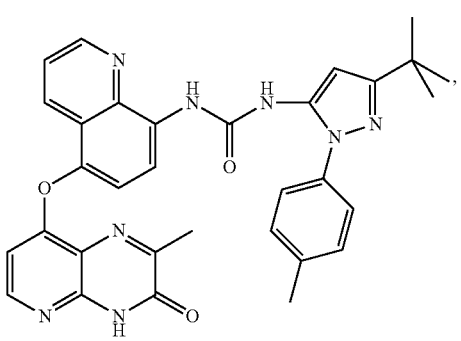
(BB-003)
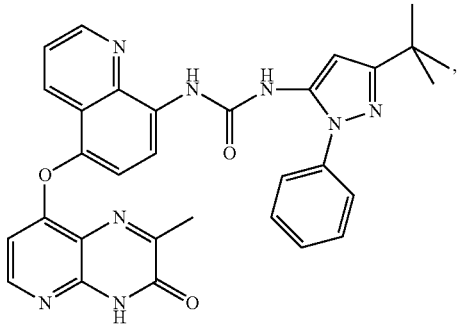
(BB-004)
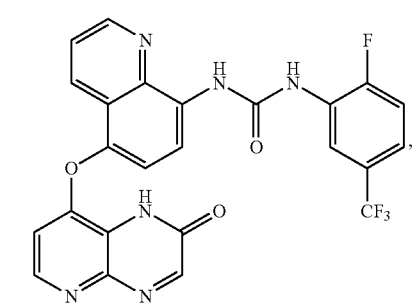
-continued
(BB-005)
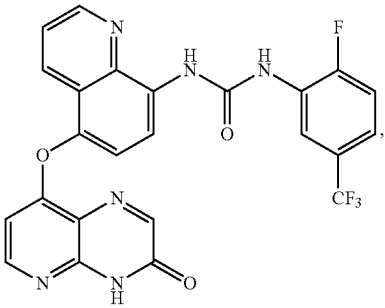
(BB-006)
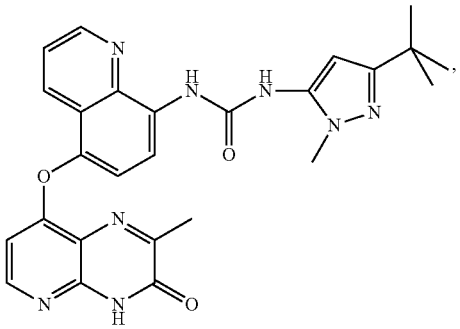
(BB-007)
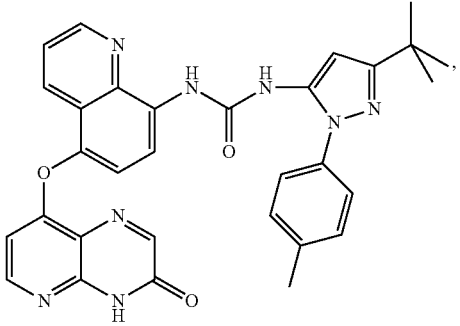
(BB-008)
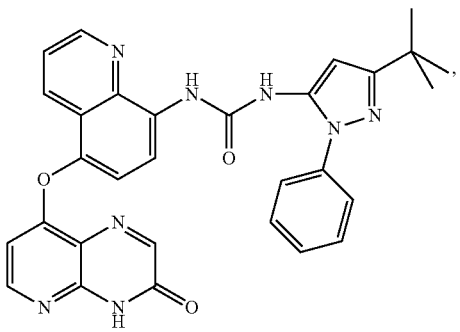
(BB-009)
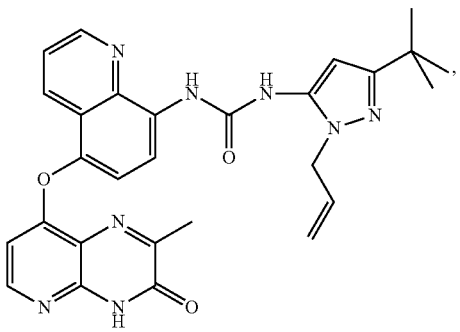

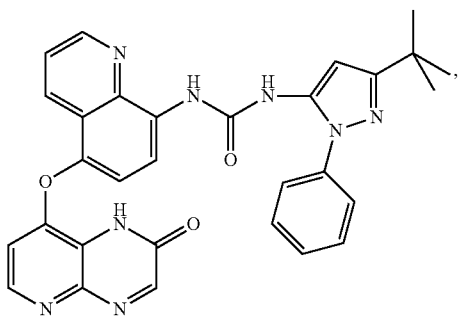
(BB-010)

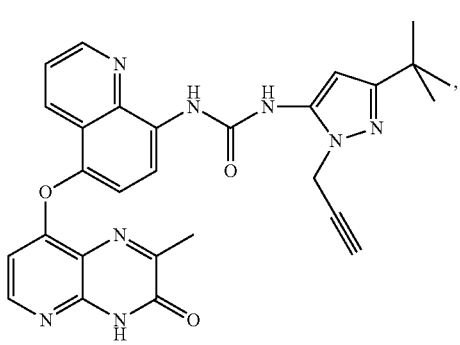
(BB-011)

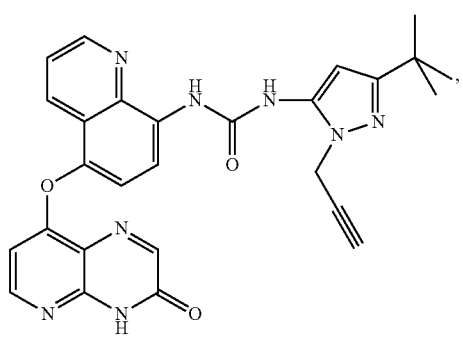
(BB-012), and

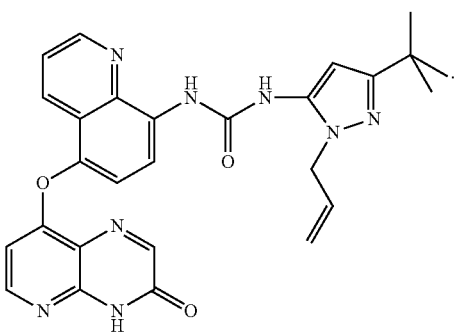
(BB-013)

23. A pharmaceutical composition comprising a compound according to claim 1, and a pharmaceutically acceptable carrier or diluent.

24. A pharmaceutical composition comprising a compound according to claim 2, and a pharmaceutically acceptable carrier or diluent.

25. A pharmaceutical composition comprising a compound according to claim 4, and a pharmaceutically acceptable carrier or diluent.

26. A pharmaceutical composition comprising a compound according to claim 8, and a pharmaceutically acceptable carrier or diluent.

27. A pharmaceutical composition comprising a compound according to claim 14, and a pharmaceutically acceptable carrier or diluent.

28. A pharmaceutical composition comprising a compound according to claim 16, and a pharmaceutically acceptable carrier or diluent.

29. A pharmaceutical composition comprising a compound according to claim 21, and a pharmaceutically acceptable carrier or diluent.

* * * * *